United States Patent [19]

Biller et al.

[11] Patent Number: 5,157,027

[45] Date of Patent: Oct. 20, 1992

[54] BISPHOSPHONATE SQUALENE SYNTHETASE INHIBITORS AND METHOD

[75] Inventors: Scott A. Biller, Ewing; David R. Magnin, Hamilton, both of N.J.

[73] Assignee: E. R. Squibb & Sons, Inc., Princeton, N.J.

[21] Appl. No.: 699,429

[22] Filed: May 13, 1991

[51] Int. Cl.$^5$ .................. A61K 31/66; C07F 9/38; C07F 9/40

[52] U.S. Cl. .................. 514/107; 514/105; 514/108; 549/220; 549/221; 549/222; 558/77; 558/83; 558/155; 558/161; 562/21

[58] Field of Search .............. 558/155, 161; 514/107, 514/108; 562/21

[56] References Cited

U.S. PATENT DOCUMENTS

| | | | |
|---|---|---|---|
| 3,299,123 | 1/1967 | Fitch et al. | 562/21 |
| 3,959,458 | 5/1976 | Agricola et al. | 424/52 |
| 4,067,971 | 1/1978 | Francis et al. | 514/108 |
| 4,113,861 | 9/1978 | Fleisch et al. | 514/102 |

Primary Examiner—Mary C. Lee
Assistant Examiner—Michael G. Ambrose
Attorney, Agent, or Firm—Burton Rodney

[57] ABSTRACT

Compounds which are inhibitors of cholesterol biosynthesis (by inhibiting de novo squalene biosynthesis), and thus are useful as hypocholesterolemic agents and antiatherosclerotic agents are provided which have the structure

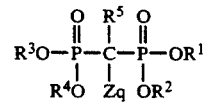

and analogs thereof, wherein $R^1$, $R^2$, $R^3$ and $R^4$ are the same or different and are H, lower alkyl, a metal ion or a prodrug ester;

$R^5$ is H, halogen or lower alkyl;

Zq is substituted alkenyl, substituted alkynyl, mixed alkenyl-alkynyl or substituted phenylalkyl or, phenylalkenyl or phenylalkynyl, or alkyl, including all stereoisomers thereof.

New methods for using such compounds to inhibit cholesterol biosynthesis are also provided.

24 Claims, No Drawings

BISPHOSPHONATE SQUALENE SYNTHETASE INHIBITORS AND METHOD

FIELD OF THE INVENTION

The present invention relates to new bisphosphonate compounds which are useful in inhibiting cholesterol biosynthesis by inhibiting de novo squalene production, to hypocholesterolemic and antiatherosclerotic compositions containing such compounds and to a method of using such compounds for inhibiting cholesterol biosynthesis and atherosclerosis.

BACKGROUND OF THE INVENTION

Squalene synthetase is a microsomal enzyme which catalyzes the reductive dimerization of two molecules of farnesyl pyrophosphate (FPP) in the presence of nicotinamide adenine dinucleotide phosphate (reduced form) (NADPH) to form squalene (Poulter, C. D.; Rilling, H. C., in "Biosynthesis of Isoprenoid Compounds", Vol. I, Chapter 8, pp. 413-441, J. Wiley and Sons, 1981 and references therein). This enzyme is the first committed step of the de novo cholesterol biosynthetic pathway. The selective inhibition of this step should allow the essential pathways to isopentenyl tRNA, ubiquinone, and dolichol to proceed unimpeded. Squalene synthetase, along with HMG-CoA reductase has been shown to be down-regulated by receptor mediated LDL uptake (Faust, J. R.; Goldstein, J. L.; Brown, M. S. *Proc. Nat. Acad. Sci. USA*, 1979, 76, 5018-5022), lending credence to the proposal that inhibiting squalene synthetase will lead to an up-regulation of LDL receptor levels, as has been demonstrated for HMG-CoA reductase, and thus ultimately should be useful for the treatment and prevention of hypercholesterolemia and atherosclerosis.

DESCRIPTION OF THE INVENTION

In accordance with the present invention, there is provided bisphosphonate compounds which inhibit cholesterol biosynthesis, and thus are useful as hypocholesterolemic and antiatherosclerotic agents and have the following structure

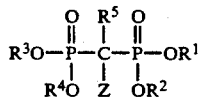
I.

wherein $R^1$, $R^2$, $R^3$ and $R^4$ are the same or different and are H, alkyl, a metal ion or a prodrug ester;

$R^5$ is H, halogen or lower alkyl;

Z is substituted alkenyl wherein the alkenyl group contains from 7 to 25 carbon atoms in the chain and from 1 to 4 double bonds; substituted alkynyl containing 1 to 4 triple bonds; mixed alkenyl-alkynyl containing 1 to 3 double bonds and 1 to 3 triple bonds and wherein alkenyl and/or alkynyl may be substituted or unsubstituted; or a substituted phenylalkyl group, substituted phenylakenyl group or substituted phenylalkynyl group of the structure

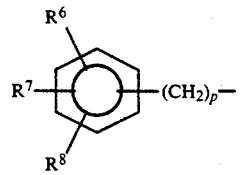

wherein $(CH_2)_p$ contains from 1 to 15 carbons, preferably 2 to 12 carbons, in the chain and may include 0, 1, 2 or 3 double bonds and/or 0, 1, 2 or 3 triple bonds in the normal chain, and/or may include 0, 1 or 2 substituents; and $R^6$, $R^7$ and $R^8$ are the same or different and are H, alkyl containing 1 to 40 carbons, preferably from 3 to 15 carbons, alkoxy containing 1 to 40 carbons, preferably from 3 to 15 carbons, alkenyl containing 2 to 40 carbons, preferably from 3 to 15 carbons, alkenyloxy containing 2 to 40 carbons, preferably from 3 to 15 carbons, alkynyl containing 2 to 40 carbons, preferably from 3 to 15 carbons, alkynyloxy containing 2 to 40 carbons, preferably from 3 to 15 carbons, aryloxy, hydroxy, halogen, nitro, amino, thiol, alkylthio, arylthio, alkylsulfinyl, arylsulfinyl, alkylsulfonyl, arylsulfonyl, carboxy, alkoxycarbonyl, aminocarbonyl, alkylcarbonyloxy, arylcarbonyloxy, arylcarbonylamino or alkylcarbonylamino, at least one of $R^6$, $R^7$ and being alkenyl, alkenyloxy, alkynyl or alkynyloxy; and wherein the total number of carbons in the substituted phenylalkyl group exceeds 10 carbons.

The terms "substituted alkenyl" and "substituted alkynyl" as employed herein with respect to Z refers to alkenyl or alkynyl substituted with 1 to 4 groups which may be alkyl, alkenyl, alkynyl, halogen, hydroxy, alkoxy, alkenyloxy, alkynyloxy, aryl and/or cycloalkyl.

The $(CH_2)p$ group may contain one or more alkyl, alkoxy, alkenyl, alkynyl, hydroxy and/or halogen substituents.

In a preferred embodiment, the formula I compounds of the invention have the structure

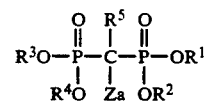
II wherein $R^1$, $R^2$, $R^3$, $R^4$ and $R^5$ are as defined above and Za is substituted alkenyl which includes from 1 to 4 double bonds and is substituted with from 1 to 4 alkyl groups.

In addition, in accordance with the present invention, compounds are provided having the structure

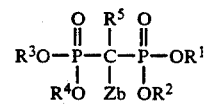
III wherein Zb is

-continued

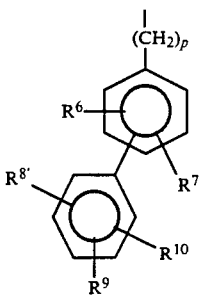

wherein $R^1$, $R^2$, $R^3$, $R^4$, $R^5$, $R^6$, $R^7$ and $(CH_2)_p$ are as defined hereinbefore, except that $R^6$ and $R^7$ may be any one of the groups included under the definition $R^6$ and $R^7$, set out hereinbefore, without limitation; $R^8$, $R^9$ and are the same or different and are as defined hereinbefore with respect to $R^6$ and $R^7$, without limitation.

Preferred are compounds of formula III wherein the $R^{8'}$, $R^9$, $R^{10}$-substituted phenyl is para to the $R^6$, $R^7$-phenylene. These compounds have been found to inhibit cholesterol biosynthesis when administered orally.

In another embodiment of the present invention, compounds are provided which have oral cholesterol biosynthesis inhibitory activity and have the structure

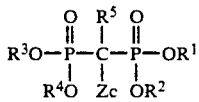   IV wherein $R^1$, $R^2$, $R^3$, $R^4$ and $R^5$ are as defined hereinbefore and Zc is alkyl wherein the alkyl group contains from 9 to 14 carbons in the normal chain and is substituted with 1, 2, 3 or 4 alkyl groups In still another embodiment of the invention, a compound is provided having the structure

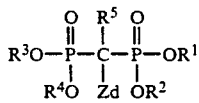   V wherein Zd is

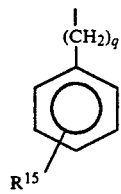

wherein $R^1$, $R^2$, $R^3$, $R^4$ and $R^5$ are as defined hereinbefore and $(CH_2)_q$ contains at least 2 carbons in the chain and may include 0, 1, 2 or 3 double bonds and/or 0, 1, 2 or 3 triple bonds in the normal chain, preferably 3 to 7 carbons in the normal chain, and may include one or more alkyl, alkenyl, alkynyl, alkoxy, hydroxy and/or halogen substituents; and $R^{15}$ is alkyl containing from 2 to 20 carbons, and preferably is in the para position, and the total number of carbons in Zd exceeds 10.

The term "prodrug esters" as employed herein includes, but is not limited to, the following groups: (1-alkanoyloxy)alkyl such as,

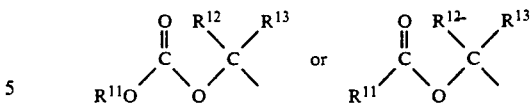

wherein $R^{11}$, $R^{12}$ and $R^{13}$ are H, alkyl, aryl or arylalkyl. Examples of such prodrug esters include $CH_3CO_2CH_2-$,

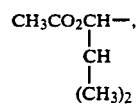

$t\text{-}C_4H_9CO\text{hd }2CH_2-$, or

Other examples of suitable prodrug esters include

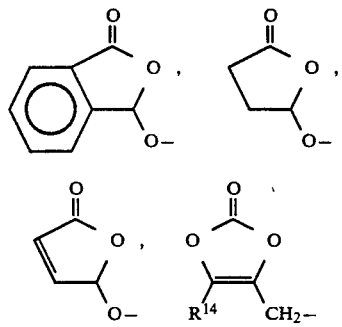

wherein $R^{14}$ is H, $CH_3$, $C_6H_5$; or $R^1$ and $R^2$, and/or $R^3$ and $R^4$ can be taken together as in

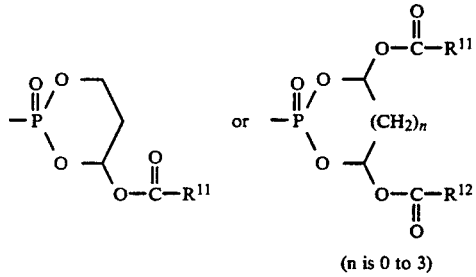

(n is 0 to 3)

Unless otherwise indicated, the term "lower alkyl" or "alkyl" as employed herein alone or as part of another group includes both straight and branched chain hydrocarbons, containing 1 to 40 carbons, preferably 1 to 20 carbons, in the normal chain, more preferably 1 to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, such as F, Br, Cl or I or $CF_3$, alkoxy, aryl, arylalkyl, alkenyl, cycloalkyl, amino, hydroxy, alkylamido, alkanoylamino, arylcarbonylamino, nitro, cyano, thiol and/or alkylthio.

Unless otherwise indicated, the term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 to 4 substituents such as halogen, alkyl, alkoxy, hydroxy, aryl, arylalkyl, cycloalkyl, alkylamido, alkanoylamino, arylcarbonylamino, amino, nitro, cyano, thiol and/or alkylthio.

Unless otherwise indicated, the term "aryl" or "Ar" as employed herein refers to monocyclic or bicyclic aromatic groups containing from 6 to 10 carbons in the ring portion, such as phenyl, naphthyl or phenyl or naphthyl substituted with 1 to 3 substituents such as alkyl, halogen (Cl, Br or F), alkoxy, hydroxy, amino, alkanoylamino, arylcarbonylamino, aryl, arylalkyl, cycloalkyl, alkylamido, nitro, cyano, thiol and/or alkylthio.

The terms "aralkyl", "aryl-alkyl" or "aryl-lower alkyl" as used herein alone or as part of another group refers to alkyl groups as discussed above having an aryl substituent, such as benzyl or phenethyl.

The terms "lower alkoxy", "alkoxy", "aryloxy" or "aralkoxy" as employed herein alone or as part of another group includes any of the above alkyl, aralkyl or aryl groups linked to an oxygen atom.

The terms "lower alkylthio", "alkylthio", "arylthio" or "aralkylthio" as employed herein alone or as part of another group includes any of the above alkyl, alkyl, aralkyl or aryl groups linked to a sulfur atom.

The terms "lower alkylamino", "alkylamino", "arylamino", "arylalkylamino" as employed herein alone or as part of another group includes any of the above alkyl, aryl or arylalkyl groups linked to a nitrogen atom.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 40 carbons, preferably 2 to 20 carbons in the normal chain, which include one double bond in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like, and which may be optionally substituted with 1 to 4 substituents, namely, halogen, alkyl, alkoxy, alkenyl, alkynyl, aryl, arylalkyl, cycloalkyl, amino, hydroxy, alkanoylamino, alkylamido, arylcarbonylamino, nitro, cyano, thiol and/or alkylthio.

Unless otherwise indicated, the term "lower alkynyl" or "alkynyl" as used herein by itself or as part of another group refers to straight or branched chain radicals of 2 to 40 carbons, preferably 2 to 20 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, alkyl, alkoxy, alkenyl, alkynyl, aryl, arylalkyl, cycloalkyl, amino, hydroxy, alkanoylamino, alkylamido, arylcarbonylamino, nitro, cyano, thiol and/or alkylthio.

Examples of suitable $(CH_2)_p$ and $(CH_2)_q$ groups include

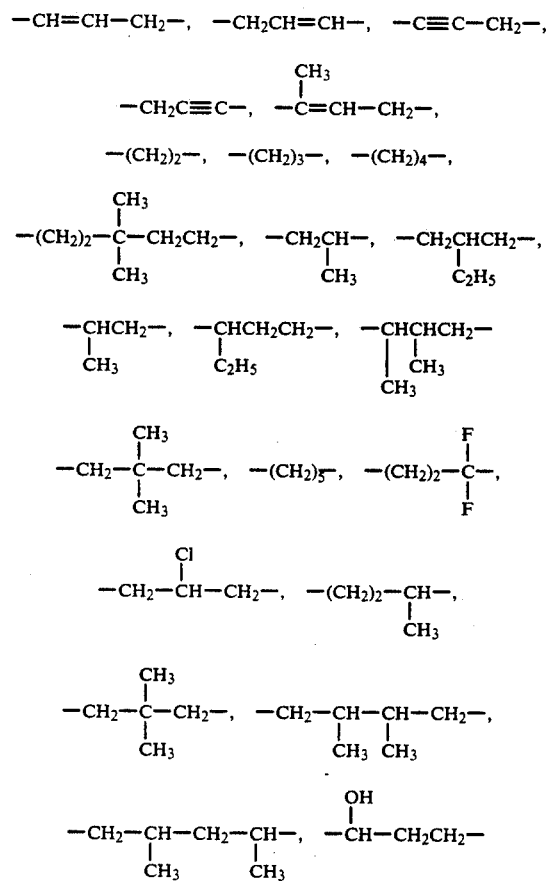

The term "halogen" or "halo" as used herein refers to chlorine, bromine, fluorine, and iodine as well as $CF_3$, with chlorine or fluorine being preferred.

The term "amino" as used herein refers to unsubstituted amino as well as monosubstituted amino or disubstituted amino wherein the substituents may be alkyl and/or aryl.

The term "metal ion" refers to alkali metal ions such as sodium, potassium or lithium and alkaline earth metal ions such as magnesium and calcium.

Preferred are those compounds of formula I wherein $R^1$, $R^2$, $R^3$ and $R^4$ are independently H, alkyl such as $CH_3$, $C_2H_5$, or the corresponding alkali metal salt, $R^5$ is H, and Z is substituted alkenyl, alkyl, substituted with 1, 2, 3 or 4 alkyl groups, substituted phenylalkyl or substituted biphenylalkyl.

Preferred Z, Za, Zb, Zc or Zd groups include the following wherein x is 1 to 15.

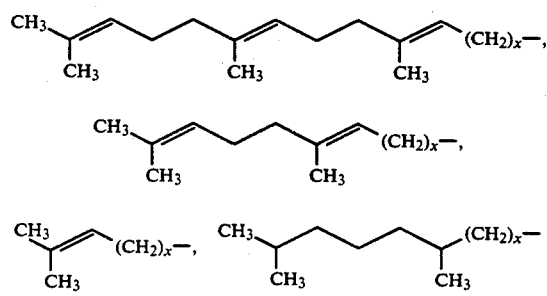

$$\underset{\substack{|\\ CH_3}}{CH_3}\!\!\!\diagdown\!\!\!\diagup\!\!\!\diagdown\!\!\!\diagup\!\!\!\underset{\substack{|\\ CH_3}}{}\!\!\!\diagdown\!\!\!\diagup\!\!\!\bigcirc\!\!\!-(CH_2)_x-,$$

$$\underset{\substack{|\\ CH_3}}{CH_3}\!\!\!\diagdown\!\!\!\diagup\!\!\!\diagdown\!\!\!\diagup\!\!\!\underset{\substack{|\\ CH_3}}{}\!\!\!\diagdown\!\!\!\diagup\!\!\!\bigcirc\!\!\!-(CH_2)_x-,$$

$$\underset{\substack{|\\ CH_3}}{CH_3}\!\!\!\diagdown\!\!\!\diagup\!\!\!\bigcirc\!\!\!-(CH_2)_x-,$$

$$\underset{\substack{|\\ CH_3}}{CH_3}\!\!\!\diagdown\!\!\!\diagup\!\!\!\diagdown\!\!\!\diagup\!\!\!\bigcirc\!\!\!-(CH_2)_x-,$$

alkyl (1-10)—◯—(CH$_2$)$_x$—,

◯—◯—(CH$_2$)$_x$—, $$\underset{\substack{|\\ CH_3}}{CH_3}\!\!\!\diagdown\!\!\!\diagup\!\!\!\bigcirc\!\!\!-(CH_2)_x-$$

The compounds of the invention may be prepared according to the following reaction sequences.

Scheme I

$$Zx-X + R^{3a}O-\underset{\substack{\|\\ R^{4a}O}}{\overset{O}{P}}-\underset{\substack{|\\ H}}{\overset{R^5}{C}}-\underset{\substack{\|\\ OR^{2a}}}{\overset{O}{P}}-OR^{1a} \xrightarrow{\text{Base Alkylation Reaction}}$$

Q        XI $$R^{3a}-\underset{\substack{\|\\ R^{4a}O}}{\overset{O}{P}}-\underset{\substack{|\\ Zx}}{\overset{R^5}{C}}-\underset{\substack{\|\\ OR^{2a}}}{\overset{O}{P}}-OR^{1a}$$

IA (X=Cl, Br, I, OSO$_2$CF$_3$ or Otosyl);
R$^{1a}$, R$^{2a}$, R$^{3a}$ and R$^{4a}$ are alkyl;
Zx=Z, Za, Zb, Zc, Zd or Zx'(CH$_2$)$_y$— (which may be the same as Z, Za, Zb, Zc or Zd).

Scheme II
(where in IA, R$^5$ is other than H, that is R$^{5a}$)

$$R^{5a}-X + R^{3a}O-\underset{\substack{\|\\ R^{4a}O}}{\overset{O}{P}}-\underset{\substack{|\\ Zx}}{\overset{H}{C}}-\underset{\substack{\|\\ OR^{2a}}}{\overset{O}{P}}-OR^{1a} \xrightarrow{\text{Base Alkylation Reaction}} IA$$

Q$^1$      IA$^1$ wherein
if R$^5$ in IA is alkyl, then R$^{5a}$ is alkyl and X is CL, Br, I or Otosyl;
if R$^5$ in IA is Cl, Br, or I, then R$^{5a}$ is Cl, Br or I and X is Cl, Br, I, OH or succinimido $$\left\{ -N\underset{\substack{}}{\overset{\substack{O\\ \|}}{\diagdown}}\underset{\substack{\|\\ O}}{\diagup} \right\} ;$$

if R$^5$ in IA is F, then R$^{5a}$X is XeF$_2$,

Alkyl (or H)
$$\underset{\substack{|\\ F^{\oplus}\ominus OSO_2CF_3}}{Alkyl (or H)\diagdown N\diagup Alkyl (or H)}$$

$$F-N\underset{\substack{|\\ alkyl}}{\overset{\substack{O\\ \|}}{-S-}}\!\!\!\diagdown\!\!\!\bigcirc\!\!\!-CH_3$$

or $$\underset{\substack{|\\ F}}{O_2S\diagdown\bigcirc\diagup SO_2\diagdown N\diagup}$$

Scheme III

$$Zx'-(CH_2)_{y+1}X \xrightarrow[\substack{\text{P(Oalkyl)}_3\\ A}]{\text{Arbuzov Reaction}} Zx'-(CH_2)_{y+1}-\underset{\substack{|\\ Oalkyl}}{\overset{\substack{O\\ \|}}{P}}-Oalkyl$$

QA                                XII y=0 to 15 and (CH$_2$)$_{y+1}$ can include 0, 1, 2 or 3 double bonds and/or 0, 1, 2 or 3 triple bonds in the normal chain and can contain alkyl, alkenyl, alkynyl, alkoxy, hydroxy and/or halogen substituents $$R^{3a}O-\underset{\substack{\|\\ R^{4a}O}}{\overset{O}{P}}-\underset{\substack{|\\ (CH_2)_y\\ |\\ Zx'}}{\overset{H}{C}}-\underset{\substack{\|\\ OR^{2a}}}{\overset{O}{P}}-OR^{1a} \xleftarrow[\substack{\text{1) sec-C}_4H_9Li\\ \text{2) HaloPO(Oalkyl)}_2\\ B}]{\text{Phosphorylation}} \begin{array}{c}XII\\ \downarrow\end{array}$$

IC where Zx'(CH$_2$)$_y$ is Zx and thus can be Z, Za, Zb, Zc or Zd.

Scheme IV

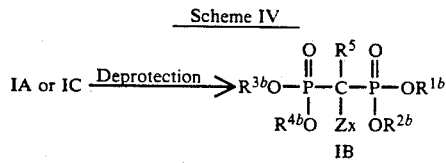

(wherein $R^{1b}$, $R^{2b}$, $R^{3b}$ and $R^{4b}$ and are metal ion, H or alkyl).

Referring to Scheme I, compounds of the invention IA may be prepared by alkylating the diphosphonate XI by reacting XI with compound Q in the presence of an appropriate base and an inert organic solvent under an inert atmosphere to form IA.

In carrying out the above reaction, the diphosphonate XI is employed in a molar ratio to compound Q of within the range of from about 5:1 to about 0.8:1, and preferably from about 3:1 to about 1.5:1. The reaction is carried out under an inert atmosphere, such as argon, initially preferably at a reduced temperature of within the range of from about −40° to about 110° C., and more preferably from about 0° to about 50° C., although the reaction may be completed at room temperature.

Examples of inert organic solvents suitable for use herein include, but are not limited to, dimethylformamide (DMF), tetrahydrofuran (THF), hexamethylphosphoramide (HMPA) or diethylether ($Et_2O$), or mixtures thereof.

Examples of bases suitable for use in carrying out the above reaction include, but are not limited to, alkali metal hydrides, such as sodium hydride (which is preferred), potassium hydride, lithium-, sodium- or potassium bis(trimethylsilyl)amide, lithium diisopropylamide or butyllithium.

Referring to Scheme II compounds of formula IA of the invention wherein $R^5$ is other than H may be prepared by reacting starting material $Q^1$ with bisphosphonate IA' (prepared as described in Schemes I or III) in the presence of a strong base such as any of those used in Scheme I, and an inert organic solvent such as used in Scheme I, to form IA where $R^5$ is other than H.

In carrying out the reaction of Scheme II, bisphosphonate IA' will be employed in a molar ratio to $Q^1$ of within the range of from about 2:1 to about 1:2, and preferably from about 1.5:1 to about 1:1.5 The reaction is carried out at a temperature of within the range of from about −40° to about 110° C., and preferably from about 0° to about 50° C.

Referring to Scheme III, compounds of the invention IB may be prepared by subjecting halide QA to an Arbuzov reaction by reacting QA with a trialkyl phosphite A $$P(Oalkyl)_3 \qquad A$$

to form monophosphonate XII which is then phosphorylated by reacting XII with a base such as sec-butyllithium, n-butyllithium, t-butyllithium, or lithium diisopropylamide, in an etherial solvent such as diethyl ether or THF, at a temperature within the range of from about −100° C. to about 0° C., followed by reaction with halophosphate B

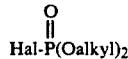

at a reduced temperature of within the range of from about −78° C. to about 25° C., to form the bisphosphonate IC upon workup.

In carrying out the Arbuzov reaction, the halide QA is employed in a molar ratio to the phosphite A of within the range of from about 1:2 to about 1:20, and preferably from about 1:3 to about 1:10. The reaction is carried out under an inert atmosphere, such as argon, at a temperature within the range of from about 50° to about 200° C., and preferably from about 100° to about 150° C.

The Arbuzov reaction is usually carried out neat, but can be carried out in an inert solvent such as benzene, toluene, xylene or THF.

The phosphorylation reaction of Scheme III will be carried out employing a molar ratio of monophosphonate XII to the halophosphate B within the range of from about 3:1 to about 1:3, and preferably from about 2:1 to about 1:2. The reaction will be carried out at a temperature of within the range of from about −78° C. to about 25° C.

As seen in Scheme IV, the diphosphonate tetraester of the invention (IA) may be fully deprotected by treatment with a deprotecting agent such as trimethylsilyl bromide or trimethylsilyl iodide, if necessary, in the presence of a proton scavenger such as 2,4,6-collidine, triethylamine or bis(trimethylsilyl)trifluoroacetamide, to provide the corresponding bisphosphonic acid where $R^{1b}$, $R^{2b}$, $R^{3b}$ and $R^{4b}$ are each H. The diphosphonate tetraester IA may also be partially deprotected by treatment with base or strong nucleophiles, such as sodium hydroxide, potassium hydroxide, thiourea, sodium iodide in acetone, sodium propanethiolate in HMPA or t-butylamine at reflux.

When a basic solution of the tetraacid (pH greater than 11) is chromatographed on CHP20P or SP207SS support, the trimetal salt will generally be obtained, although chromatographing less lipophilic tetraacid compounds will sometimes give the tetrametal salt.

The tetrametal salt may be obtained by adding an organic solvent such as acetone, THF or alcohol such as methanol, ethanol or isopropanol, to a basic aqueous solution (pH greater than 11) of the acid, resulting in the precipitation of the salt.

The starting materials Q, that is ZxX and QA, that is Zx'—$(CH_2)_{y+1}$X may be prepared from their corresponding alcohol XIV $$Zx-OH \qquad \qquad XIV$$

which may also be represented as XV $$Zx'-(CH_2)_{y+1}OH \qquad \qquad XV$$

employing conventional procedures as will be apparent to those skilled in the art. For example, where X is Cl, alcohol XIV or XV may be treated with N-chlorosuccinimide in the presence of dimethylsulfide or methanesulfonyl chloride, lithium chloride, DMF or collidine to form Q or QA.

Where X is Br, alcohol XIV or XV may be treated with phosphorus tribromide in the presence of ethyl ether to form Q or QA. In another method, XIV or XV may be treated with methylsulfonyl chloride in the presence of triethylamine followed by lithium bromide in the presence of THF to form Q or QA. Still another method for preparing bromide Q or QA involves treatment of XIV or XV with N-bromosuccinimide in the presence of triphenylphosphine.

Where X is iodide, iodides Q or QA may be prepared by treating XIV or XV with methylsulfonyl chloride and triethyl amine followed by sodium iodide in acetone or triphenylphosphine, imidazole and iodine in THF.

The alcohol starting material XV having the formula XVA $$Zx'-CH_2CH_2OH \qquad XVA$$

may be prepared according to the following reaction sequence (following the procedure of E. J. Leopold, *Organic Synthesis* 1985, 64, pp 164-173)

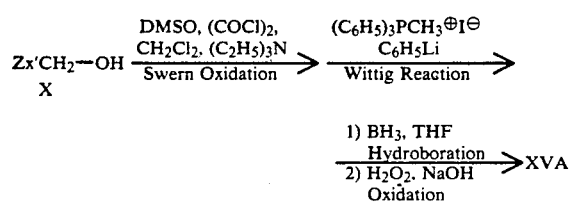

The alcohol starting material XV having the formula XVB $$Zx'-CH_2CH_2CH_2-OH \qquad XVB$$

may be prepared according to the following reaction sequence:

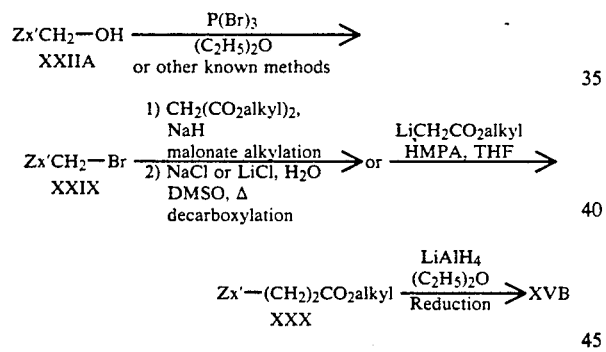

The alcohol starting material XV having the formula XVC $$Zx'-(CH_2)_{4 or 7}OH \qquad XVC$$

may be prepared according to the following reaction sequence

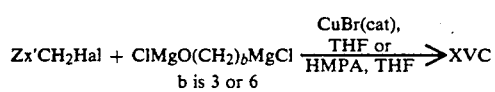

b is 3 or 6

The starting alcohol XV $$Zx'-(CH_2)_{y+1}OH \qquad XV$$

where y is greater than 2 may be prepared according to the following reaction sequence:

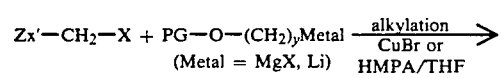

-continued

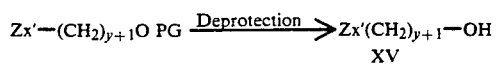

where PG is a protecting group such as

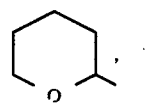

$t-C_4H_9(CH_3)_2Si-$, $t-C_4H_9(C_6H_5)_2Si-$.

The alcohols XIV and XV may then be employed to make longer chain alcohol starting material XIV or XV by utilizing any of the above homologation reactions in succession.

Alcohol starting material XV wherein Zx includes a linking double bond, that is $$Zx'-CH=CH-CH_2-OH \qquad XVD$$

may be prepared according to the following reaction sequence:

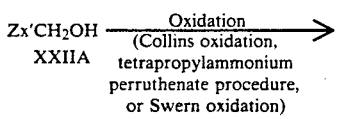

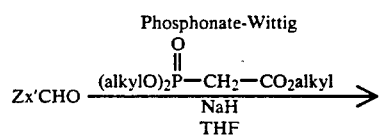

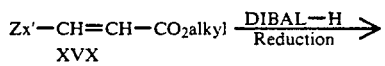

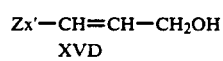

Where Zx' in XVX is an aryl such as phenyl directly bonded to the olefin moiety of XVX, then the preferred route for preparing XVX is as follows.

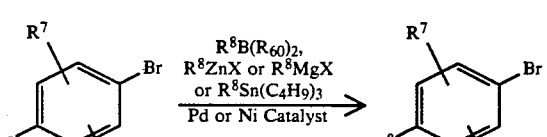

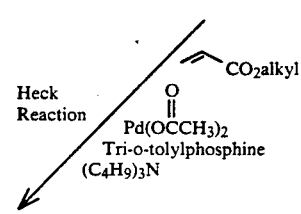

-continued

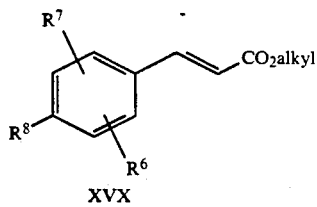
XVX where $(R_{60})_2 = $ (alkyl)$_2$, (OH)$_2$,

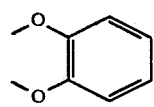

Alcohol starting material XV having the formula XVB, may be prepared according to the following reaction sequences

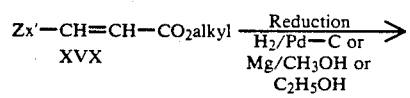

$$Zx'-CH_2CH_2CO_2alkyl$$
$$\downarrow LAH$$
$$Zx'-(CH_2)_3OH$$
XVB

Alcohol starting materials XV where Zx includes a —C≡C— group, that is $$Zx'-C\equiv C-CH_2OH \qquad XVE$$

may be prepared according to the following reaction sequence $$Zx'-CHO \xrightarrow{P(C_6H_5)_3}{CBr_4}$$

$$Zx'-CH=C-Br \xrightarrow[\text{(2) paraformaldehyde}]{\text{(1) n-C}_4\text{H}_9\text{Li}}$$
<br>
| Br $$Zx'-C\equiv C-CH_2OH$$
XVE Alcohol starting material of the structure XVF

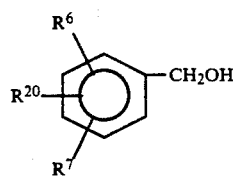
XVF where $R^{20}$ is $R^8$, $R^{15}$ or

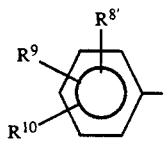

may be prepared according to the following reaction sequence

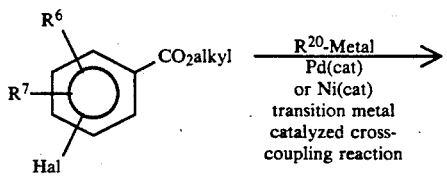

(Hal = Br, I or —OSO$_2$CF$_3$)

(where Metal is MgX, ZnX, Sn(butyl)$_3$, Sn(methyl)$_3$, B(OH)$_2$ or B(ethyl)$_2$)

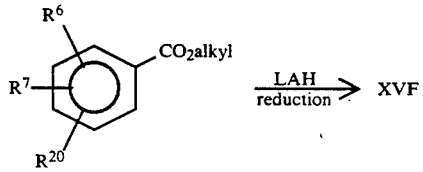

Alcohol starting material of the structure

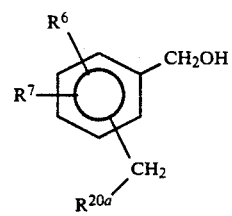
XVG (wherein $R^{20a}$ is alkyl or arylalkyl, or alkenylalkyl) may be prepared according to the following reaction sequence

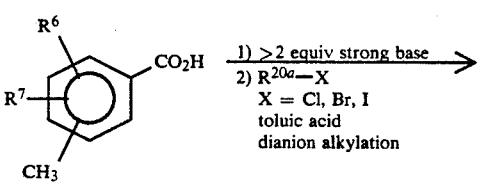

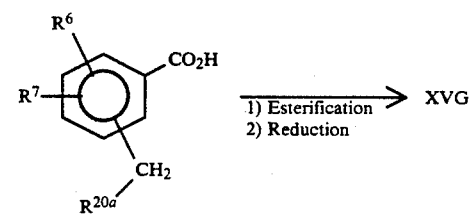

Alcohol starting material of the structure XVH

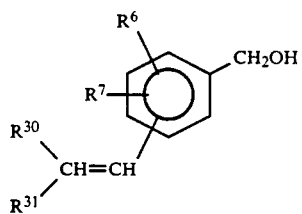

XVH ($R^{30}$ and $R^{31}$ are H, alkyl, aryl, alkenyl, alkynyl, halo(Cl,F,Br)) may be prepared according to the following reaction sequence:

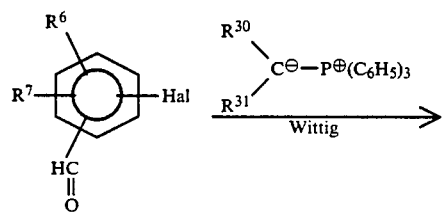

(Hal = Cl, I or Br)

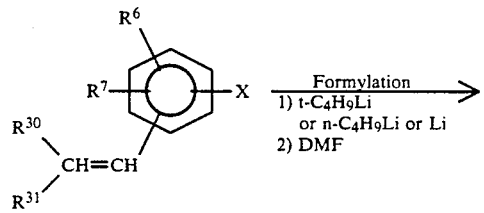

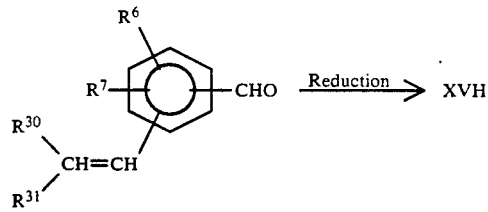

Each alcohol product (XIV or XV) can be used as a starting material for a subsequent homologation reaction as described above, to prepare a new alcohol of different chain length and substitution pattern. In the case where the homologation sequence starts with a halide, it can be prepared from the alcohol using one of many conventional methods, including those disclosed hereinbefore. In the case where the homologation starts with an aldehyde, it can be prepared from the alcohol using many conventional methods, including Collins oxidation, Swern oxidation, tetrapropylammonium perruthenate.

Examples of starting material XIV or XV that is ZxOH or Zx'CH₂OH suitable for use herein include the following which are either known in the literature or are simple derivatives of known compounds prepared by employing conventional procedures.

Each example of ZxOH or Zx'CH₂OH (XIV or XV) can be used as a starting material for a subsequent homologation reaction as described above, to prepare a new alcohol of different chain length and substitution pattern.

It will be appreciated that the compounds listed in the following table represent all possible stereoisomers.

Zx'—CH₂OH where Zx'CH₂ is as follows in A. through F.

A.
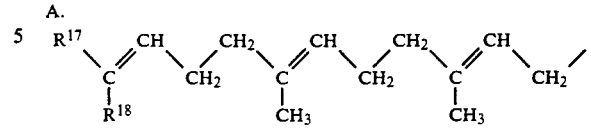

or

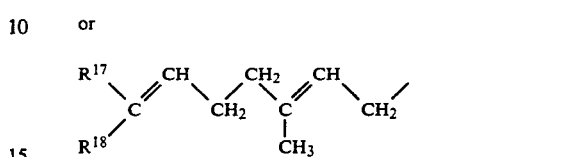

|    | $R^{17}$ | $R^{18}$ |
|----|----------|----------|
| 1. | C₂H₅ | CH₃ |
| 2. | CH₃ | C₂H₅ |
| 3. | n-C₃H₇ | CH₃ |
| 4. | CH₃ | n-C₄H₉ |
| 5. | t-C₄H₉ | CH₃ |
| 6. | —(CH₂)ₛ'— s' = 4 to 6 | |
| 7. | H | H |
| 8. | F | F |
| 9. | Cl | Cl |
| 10. | CH₂F | CH₃ |
| 11. | —CH=CH₂ | H |

B.
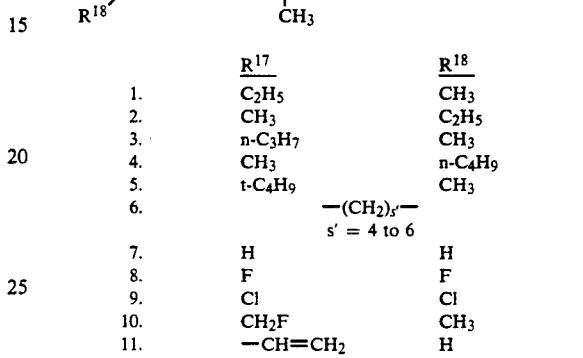

alkyl(CH₂)ₜ—

1. CH₃(CH₂)ₜ where t is 0 to 7

2. 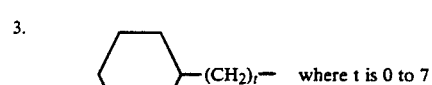 where t is 0 to 7

3.  where t is 0 to 7

4. 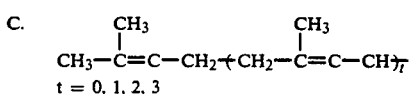 where t is 0 to 7

C. 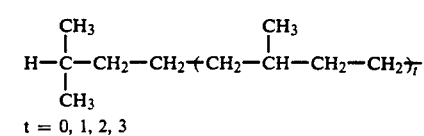

t = 0, 1, 2, 3

D. Zx'CH₂— is

-continued
Zx'—CH₂OH where Zx'CH₂ is as follows in A. through F.
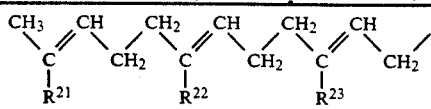
or
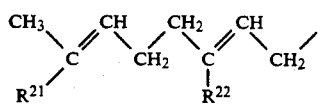
|    | R²¹   | R²²   | R²³   |
|----|-------|-------|-------|
| 1. | C₂H₅  | C₂H₅  | CH₃   |
| 2. | CH₃   | CH₃   | C₂H₅  |
| 3. | CH₃   | C₂H₅  | C₂H₅  |
| 4. | C₂H₅  | C₂H₅  | C₂H₅  |
| 5. | CH₃   | C₂H₅  | CH₃   |
| 6. | CH₃   | H     | CH₃   |
| 7. | CH₃   | CH₃   | H     |
| 8. | H     | H     | H     |
E. Zx'CH₂— is
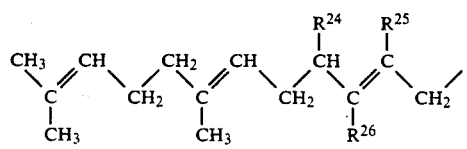
or
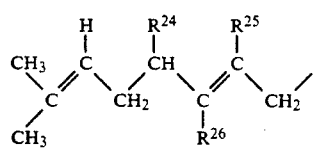
|     | R²⁴    | R²⁵   | R²⁶       |
|-----|--------|-------|-----------|
| 1.  | H      | I     | H         |
| 2.  | H      | H     | I         |
| 3.  | H      | CH₃   | CH₃       |
| 4.  | CH₃S   | CH₃   | H         |
| 5.  | F      | CH₃   | H         |
| 6.  | CH₃    | CH₃   | H         |
| 7.  | H      | CH₃   | CH₃       |
| 8.  | H      | CH₃   | Cl        |
| 9.  | H      | CF₃   | H         |
| 10. | H      | Cl    | H         |
| 11. | H      | CH₃   | (CH₃)₃Si  |
| 12. | H      | CH₃   | F         |
F. Other examples of Zx'CH₂— include the following
1. 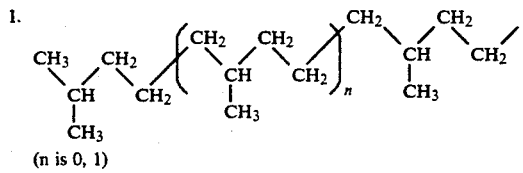
(n is 0, 1)
2. 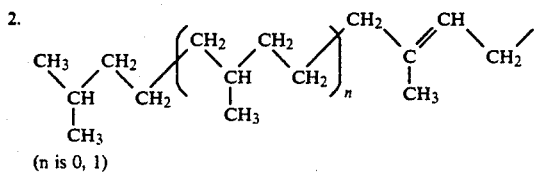
(n is 0, 1)
3. 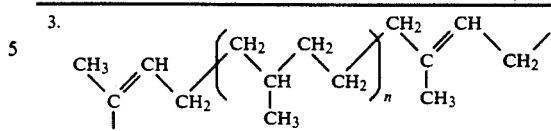
(n is 0, 1)
4. 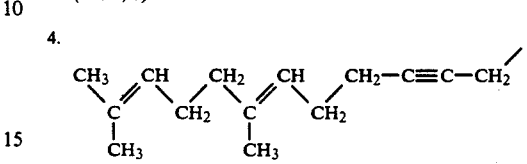
5. 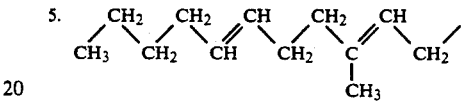
6. 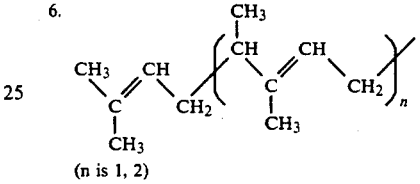
(n is 1, 2)
7. 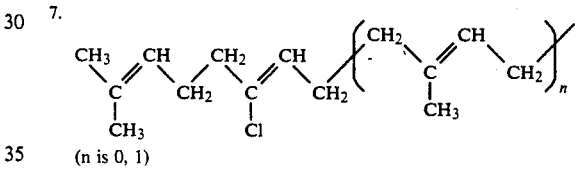
(n is 0, 1)
8. 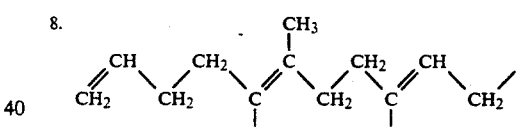
9. 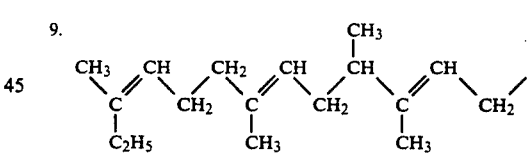
10. 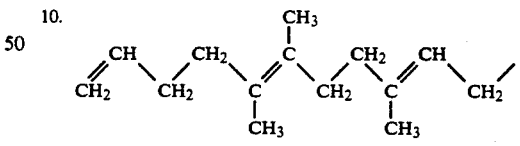
11. 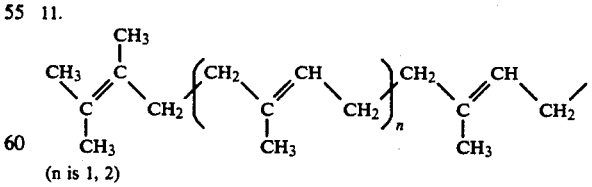
(n is 1, 2)
12. 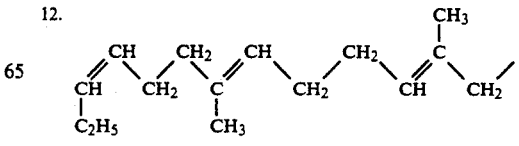

-continued

Zx'—CH2OH where Zx'CH2 is as follows in A. through F.

13. 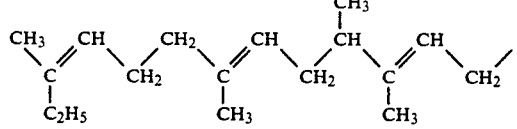

14. 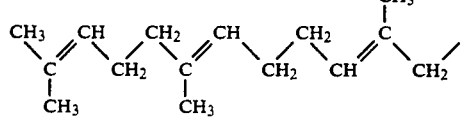

15. 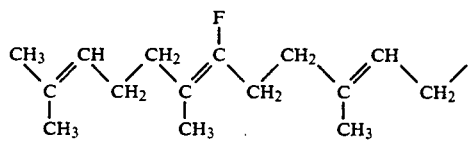

16. 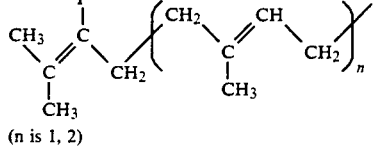

(n is 1, 2)

17. 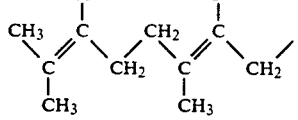

18. 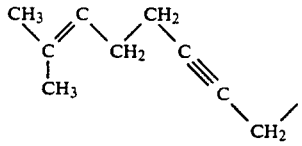

19. 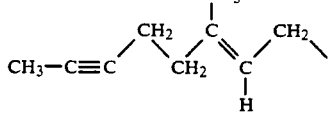

20. CH$_3$C≡C—(CH$_2$)$_n$—  (n = 4-12)
21. CH$_3$C≡C—(CH$_2$)$_n$—C≡C—CH$_2$—  (n = 2-10)

22. 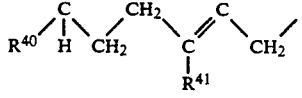

R$^{40}$ = H, alkyl, cycloalkyl, or aryl such as
methyl, ethyl, isopropyl, pentyl, phenyl and cyclopentyl
R$^{41}$ = alkyl such as methyl ethyl or halo such as Cl or F 23. 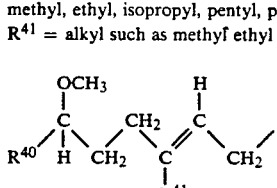

-continued

Zx'—CH2OH where Zx'CH2 is as follows in A. through F.

24. 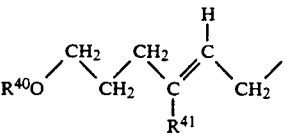

25. 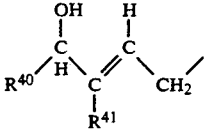

26. 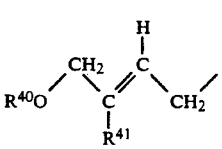

Additional compounds within the scope of the present invention are set out below.

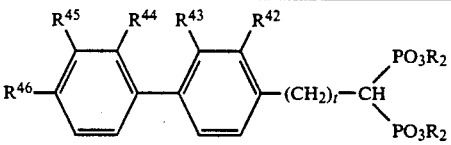

| | R$^{42}$ | R$^{43}$ | R$^{44}$ | R$^{45}$ | R$^{46}$ | t |
|---|---|---|---|---|---|---|
| 27) | H | H | H | H | CH$_3$ | 3 |
| 28) | H | H | H | H | CF$_3$ | 3 |
| 29) | H | H | H | H | NO$_2$ | 4 |
| 30) | H | H | H | H | NH$_2$ | 2 |
| 31) | CH$_3$ | H | H | H | CH$_3$ | 3 |
| 32) | H | H | CH$_3$ | H | H | 3 |
| 33) | H | CH$_3$ | CH$_3$ | H | H | 3 |
| 34) | CH$_3$O | H | H | H | H | 3 |
| 35) | H | H | H | H | CH$_3$O | 3 |
| 36) | H | H | H | H | Cl | 4 |
| 37) | CH$_3$ | H | H | H | NHCCH$_3$ (O) | 5 |
| 38) | F | H | CH$_3$ | H | H | 3 |
| 39) | CH$_3$ | H | H | H | OH | 3 |
| 40) | H | H | H | CH$_3$ | H | 3 |
| 41) | H | H | H | CF$_3$ | H | 3 |
| 42) | H | H | H | F | H | 3 |
| 43) | H | Cl | Cl | H | H | 3 |
| 44) | CH$_3$ | H | H | H | C$_4$H$_9$ | 3 |

R = H, metal ion or alkyl

45) 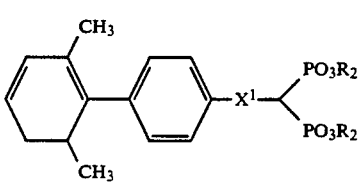

46) 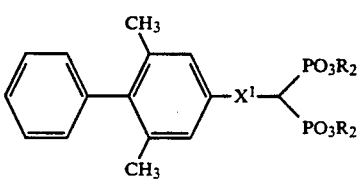

X$^1$ = —(CH$_2$)$_n$—, —CH=CH—CH$_2$—
n = 2, 5
R = H, metal ion or alkyl

-continued

47) 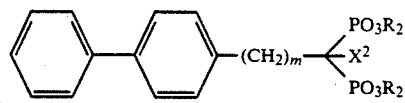

48) 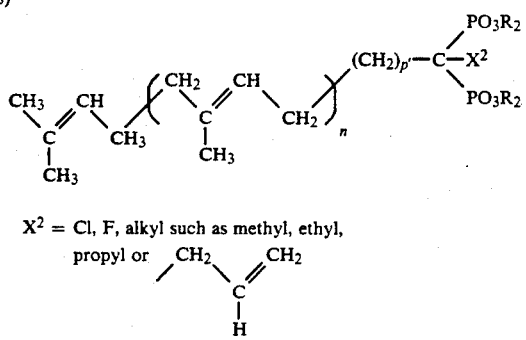

$X^2$ = Cl, F, alkyl such as methyl, ethyl, propyl or $$\begin{array}{c} CH_2 \\ \diagup \\ \end{array} \begin{array}{c} CH_2 \\ \diagdown \\ \end{array}$$
$$C$$
$$|$$
$$H$$

n = 0, 1, 2
$p^1$ = 0-8
m = 2-8
R = H, metal ion, or alkyl

The compounds of Formula I of the invention inhibit cholesterol biosynthesis by inhibition of de novo squalene production. These compounds inhibit the squalene synthetase enzyme and, in addition, some of the compounds of Formula I of the invention inhibit other enzymes in the pathway from isopentenyl diphosphate to squalene, that is, farnesyl diphosphate synthetase and isopentenyl diphosphate-dimethylallyl diphosphate isomerase.

Thus, the compounds of the invention are useful in treating atherosclerosis to inhibit progression of disease and in treating hyperlipidemia to inhibit development of atherosclerosis. In addition, the compounds of the invention may increase plasma high density lipoprotein cholesterol levels.

As bisphosphonates, the compounds of the invention may also be useful in inhibiting formation of gallstones, treating tumors, lowering blood pressure, lowering blood sugar, treating diabetes mellitus, treating inflammation, as a diuretic, as an inotropic agent, as an antiarthritic (antirheumatic) agent, in treating other diseases of calcium and phosphate metabolism including treatment of bone resorption, Paget's disease, osteoporosis, calcification of joints, implants and metastasis, as anti-tartar and anticalculus agents in toothpastes and mouthwashes, treating various stones and calculi, treating sickle cell anemia, treating hypoxia and ischemic tissue, and as an anti-ameobal agent, as well as for use in complexes with technetium-99m and radioiodinated derivatives for use as diagnostics.

The compounds of the invention may also be employed in combination with an antihyperlipoproteinemic agent such as probucol and/or with one or more serum cholesterol lowering agents such as Lopid (gemfibrozil), bile acid sequestrants such as cholestyramine, colestipol, polidexide (DEAE-Sephadex) as well as clofibrate, nicotinic acid and its derivatives, neomycin, p-aminosalicyclic acid, bezafibrate and the like and/or one or more HMG CoA reductase inhibitors such as lovastatin, pravastatin, velostatin or simvastatin.

The above compounds to be employed in combination with the squalene synthetase inhibitor of the invention will be used in amounts as indicated in the Physicians' Desk Reference (PDR).

The compounds of the invention may also be employed with sodium lauryl sulfate or other pharmaceutically acceptable detergents to enhance oral bioavailability of such compounds.

Inhibition of squalene synthetase may be measured by the following procedure.

Rat liver microsomal squalene synthetase activity is measured using farnesyl diphosphate as substrate and quantitating squalene synthesis using gas chromatographic analysis. The assay was developed by modifying conditions originally described by Agnew (Methods in Enzymology 110:357, 1985).

Preparation of Rat Liver Microsomes

Livers are dissected from 2 or 3 decapitated Sprague Dawley rats and are quickly transferred to ice cold buffer (potassium phosphate, 0.05M, (pH 7.4); $MgCl_2$, 0.004M; EDTA, 0.001M; and 2-mercaptoethanol 0.01M) and rinsed thoroughly. The livers are minced in cold buffer (2.0 ml/g) and homogenized using a Potter-Elvejhem homogenizer. The homogenate is centrifuged at 5,000 ×g, 10 minutes (4° C.), and the supernatant poured through 2 layers of cheese cloth. The supernatant is then centrifuged at 15,000 ×g for 15 minutes (4°). Again the supernatant is filtered through 2 layers of cheese cloth, and centrifuged a third time at 100,000 ×g for 1.0 hour at 4° C. Following centrifugation the microsomal pellet is resuspended in a volume of buffer equivalent to 1/5 the volume of the original homogenate, and homogenized in a ground glass homogenizer. Aliquotted microsomes are frozen at −80° C., and retain activity for at least two months.

Enzyme Assay

Reaction Mixtures are prepared in 50 ml round bottom pyrex glass tubes with tight-fitting, teflon-lined, screw caps. Tubes are cooled to 4° C., and the following components are added in sequence:

| | |
|---|---|
| 1. Potassium phosphate buffer (0.275 M, pH 7.4) | 0.36 ml |
| 2. KF (55 mM) | 0.36 ml |
| 3. NADPH (5.0 mM, freshly prepared) | 0.36 ml |
| 4. $H_2O$ (or $H_2O$ + test compound) | 0.16 ml |
| 5. $MgCl_2$ (27.5 mM) | 0.36 ml |
| 6. Microsomal Enzyme (0.48 mg microsomal protein in homogenization buffer) (15 μl prep.) 4/23/86 | 0.20 ml |
| | 1.8 ml |

This mixture is equilibrated under $N_2$ at 4° C. for 5-15 minutes. Reaction mixtures are then warmed to 30° C., and the enzyme reaction initiated by adding 0.2 ml of farnesyl pyrophosphate (219 μM) prepared in $H_2O$. Each tube is again overlayered with $N_2$, and incubated at 30° C. for 60 minutes. The reaction is stopped by the addition of 1.0 ml KOH (40%). Ethanol (95%) (spectral grade) (1.0 ml) is added to each tube. Docosane (5 nmoles in hexane) is added to each tube as an internal standard. The mixture is saponified at 65° C. for 30 minutes. The tubes are cooled to room temperature and extracted twice with 10.0 ml spectral grade hexane.

The upper organic phase fractions are pooled in glass 20.0 ml scintillation vials and reduced in volume to ≈1.0 ml under a stream of $N_2$. The sample is then transferred to acid-washed, conical bottom, glass (1.0 ml) microvials, and brought to dryness under $N_2$. The residue is resuspended in 50 μl hexane (spectral grade), and these samples are spun at 1000 rpm at room temperature for 10 minutes. Following centrifugation approximately 40 μl of supernatant is transferred to 100 μl acid-washed microvials with septa/crimp-top caps (compatible with the Hewlett-Packard GC auto injector).

Gas Chromatography

Two μL of each sample is injected onto a fused silica megabore DB-17 column (15M ×0.525 mm) (J&W Scientific) using a splitless mode of injection. Gas flow rates are listed below:

| Make up gas (helium) | 20 ml/min. |
| Air | 400 ml/min. |
| Hydrogen | 30 ml/min. |
| Carrier (helium) | 15 ml/min. |
| Septum purge vent | 5 ml/min. (Septum purge off 0.00 min., on at 0.5 min.) |

The injector temperature is 200° C., and the FID detector temperature is set at 270° C. Oven temperature is programmed through a two ramp sequence as follows:
Oven:
Initial temperature 180° C., initial time 10 minutes
Ramp one: 20° C./minute
Second temperature 250° C., second time 10 minutes
Ramp two: 20° C./minute
Third temperature 260° C., third time 10 minutes
(Equilibration time 1.0 minute)

Using this gas chromatographic system, docasane (internal standard) has a retention time of 3.6–3.7 minutes, and squalene has a retention time of 14.7–14.9 minutes. The amount of squalene in each reaction mixture is determined by obtaining the areas under the squalene and docasane peaks and using the following formula to calculate the amount of squalene (nmoles) in the total reaction mixture.

Squalene (nmoles/reaction mixture) =

$$5.0 \text{ (nmoles docasane} \times \text{internal standard)}$$

$$\frac{\text{Squalene Peak Area}}{\text{Docasane Peak Area}} \times RR^*$$

*RR = Response Ratio [Docasane/Squalene]
*RR = 0.56

Compounds Testing

Compounds are dissolved in $H_2O$ and added to reaction mixtures prior to addition of farnesyl pyrophosphate substrate. All reaction mixtures are run in duplicate, at several concentrations. Additionally, all compound $I_{50}$ values are derived from composite dose response data.

A further aspect of the present invention is a pharmaceutical composition consisting of at least one of the compounds of the invention, such as Formulae I, III, IV, V in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 200 and 2,000 mg per day, which can be administered in a single dose or in the form of individual doses from 1–4 times per day.

A typical capsule for oral administration contains active ingredient (250 mg), lactose (75 mg) and magnesium stearate (15 mg). The mixture is passed through a 60 mesh sieve and packed into a No. 1 gelatin capsule.

A typical injectible preparation is produced by asceptically placing 250 mg of sterile active ingredient into a vial, asceptically freeze-drying and sealing. For use, the contents of the vial are mixed with 2 ml of physiological saline, to produce an injectible preparation.

The following examples represent preferred embodiments of the present invention.

INTRODUCTION TO EXPERIMENTAL

All temperatures are reported in degrees Centigrade. $^1H$ and $^{13}C$ chemical shifts are reported as δ-values with respect to $Me_4Si$ (δ=0). $^{31}P$ spectra were measured on a JEOL FX90Q FT-NMR spectrometer, at 36.2 MHz, utilizing the $^1H$ decoupled mode. The $^{31}P$ data were obtained using 85% $H_3PO_4$ as an external reference (δ=0). Coupling constants J are reported in Hz. Chemical ionization mass spectra (CI-MS) were determined with a Finnigan TSQ-4600 instrument equipped with a direct exposure probe using the indicated reagent gases. Fast atom bombardment mass spectra (FAB-MS) were recorded on a VG Analytical ZAB-2F spectrometer. Ions were sputtered (8keV Xe) from a matrix containing dithiothreitol, dithioerythritol, DMSO, glycerol and water.

All reactions were carried out under an atmosphere of dry argon or nitrogen. The following reagents and solvents were distilled prior to use from the indicated drying agents, where applicable: $CH_2Cl_2$, 2,4,6-collidine, and diisopropylamine $(CaH_2)$; THF and diethyl ether (K, benzophenone); N,N-diethyltrimethylsilylamine and oxalyl chloride. Benzene was passed through neutral alumina (activity 1) and stored over 4A-molecular sieves. Lithium bromide was dried at 100° C. over $P_2O_5$. (E,E)-Farnesol was purchased from Aldrich Chemical Company.

TLC was performed on E. Merck Silica Gel 60 F-254 plates (0.25 mm) or E. Merck Cellulose F plates (0.1 mm). Flash chromatography was carried out using E. Merck Kieselgel 60 (230–400 mesh).

Reverse-phase chromatographic purification of salts or mixed ester salts was carried on CHP20P gel or SP207SS gel, highly porous, polystyrenedivinyl benzene copolymers available from Mitsubishi Chemical Industries. The indicated general procedure was followed: An FMI Model RP-SY pump was utilized for solvent delivery. A column of CHP20P or SP207SS (2.5 cm diameter, 12–22 cm height) was slurry packed and washed with water (500–1000 mL), and a basic, aqueous solution of the crude salt was applied to the top of the column. Typically, the column was eluted with water, followed by a gradient composed of increasing concentrations of acetonitrile or methanol in water. The gradient was created by placing the tip of a tightly stoppered separatory funnel containing 300–500 mL of the organic solvent, or an aqueous-organic mixture, just beneath the surface of a reservoir containing 300–500 mL of pure water. To start the gradient, the stopcock of the separatory funnel was opened, so that as the solvent was withdrawn by the pump from the reservoir, it was replaced with the solvent from the separatory funnel. HPLC-grade solvents were employed. Fractions were collected (10-15 mL each) at a flow rate of 5-10 mL per minute. Those fractions that contained pure product as judged by TLC or HPLC were pooled, the organic solvents were evaporated and the aqueous residue was lyophilized to dryness.

The following examples represent preferred embodiments of the present invention.

EXAMPLE 1

(E,E)-(6,10,14-Trimethyl-5,9,13-pentadecatrienylidene)bisphosphonic acid, trisodium salt

A. Bishomofarnesol (1) (E,E)-3,7,11-Trimethyl-2,6,10-dodecatrienyl bromide (farnesyl bromide)

A solution of 1.00 g (4.5 mmol) of (E,E)farnesol (Aldrich, further purified by flash chromatography) in 10 mL of distilled ether at 0° C. under argon in the dark was treated dropwise with a solution of 195 μL (2.05 mmol, 0.45 eq.) of PBr$_3$ in 2 mL of diethyl ether (ether). The resultant mixture was stirred at 0° C. for one hour, then quenched with water and separated. The organic phase was washed with 5 mL of H$_2$O, 5 mL of saturated NaHCO$_3$, and 5 mL of brine, dried over Na$_2$SO$_4$ and evaporated to give 1.26 g (98%) of crude bromide as a clear oil.

TLC Silica (2:8 ethyl acetate:hexane) R$_f$=0.69.

$^1$H NMR (CDCl$_3$, 270 MHz): δ5.52 (t,1H, J=8.5 Hz), 5.08 (m, 2H), 4.01 (d, 2H, J=8.5 Hz), 2.20-1.90 (m, 8H), 1.73 (s, 3H), 1.68 (s, 3H), 1.60 (s, 6H) ppm.

(2) (E,E)-5,9,13-Trimethyl-4,8,12-tetradecatrienoic acid, 1,1-dimethylethyl ester To a solution of 9.60 mL (68.5 mmol, 1.5 eq.) of diisopropylamine in 100 mL of tetrahydrofuran (THF) at −78° C. under argon was added 28.2 mL (45.0 mmol, 1.0 eq.) of 1.6 M n-butyllithium in hexanes over 20 minutes. After warming to 0° C. for 15 minutes, the solution was recooled to −78° C. and 6.05 mL (45 mmol, 1.0 eq.) of t-butyl acetate was added over 20 minutes. After an additional 15 minutes, 16.0 mL (92 mmol, 2.05 eq.) of hexamethylphosphoramide (HMPA) was added, followed by a solution of 12.53 g (45.0 mmol) of Part A(1) farnesyl bromide in 100 mL of THF over 20 minutes. The reaction was stirred at −78° C. for 2.5 hours, quenched with saturated NH$_4$Cl and allowed to warm to room temperature. After diluting with 400 mL of ethyl acetate, the mixture was washed with four 100 mL portions of water, and 200 mL of brine, dried over MgSO$_4$ and evaporated to provide 12.96 g of crude product as a yellow oil. Purification by flash chromatography on 1 kg of silica gel, eluted with 1:9 ethyl acetate:petroleum ether afforded 9.39 g (65%) of title compound as a pale yellow oil.

TLC Silica gel (2:98 ethyl acetate:hexane) R$_f$=0.16.

IR(neat) 2977, 2925, 2857, 1733, 1452, 1368, 1258, 1149 cm$^{-1}$. $^1$H NMR(CDCl$_3$, 270 MHz): δ5.10 (m,3H), 2.25 (m, 4H), 2.10-1.90 (m, 8H), 1.68 (s, 3H), 1.62 (s, 3H), 1.59 (s, 6H), 1.44 (s, 9H) ppm.

Mass Spec (CI-CH$_4$/N$_w$O) (+ions) m/e 165 (M+H-C$_4$H$_8$), 247, 183, 137, 68, 57. (−ions) m/e 319 (M−H), 279, 251, 100.

(3) Bishomofarnesol

To a stirred solution of 5.00 g (15.6 mmol) of Part (2) compound in 45 mL of dry diethyl ether at 0° C. under argon was added 592 mg (15.6 mmol, 1 mol - eq.) of lithium aluminum hydride, and the resulting suspension was stirred at room temperature for 20 hours. After cooling to 0° C., the reaction was quenched by treating with 5 mL of H$_2$O, 5 mL of 15% NaOH, and 15 mL of H$_2$O and stirring the suspension for ½ hour. After adding Na$_2$SO$_4$, the slurry was filtered through Celite, washing well with diethyl ether and evaporated to obtain 3.62 g of crude product. Purification by flash chromatography on 300 g of silica gel, eluted with 1:9 ethyl acetate:petroleum ether provided 3.516 g (90%) of bishomofarnesol as a colorless liquid.

TLC Silica gel (2:8 ethyl acetate (EtOAc):hexane) R$_f$=0.19.

IR(neat) 3330, 2964, 2926, 2873, 2958, 1448, 1384, 1107, 1059, 401 cm$^{-1}$.

$^1$H NMR(CDCl$_3$, 270 MHz): δ5.10 (m, 3H), 3.63 (t, 2H, J=6.5 Hz), 1.9-2.2 (m, 10H), 1.68 (s, 3H), 1.62 (2, 3H), 1.60 (s, 7H) ppm.

Mass Spec (CI-CH$_4$/N$_2$O, +ions) m/e 251 (M+H), 249 (M+H-H$_2$), 137, 123, 109, 69.

A$^1$. Bishomofarnesol (alternative preparation)

(1) (E,E)-(3,7,11-Trimethyl-2,6,10-undecadienyl)-propanedicarboxylic acid, diethyl ester To a suspension of 1.62 g (40.5 mmol, 3 eq.) of a 60% suspension of sodium hydride in mineral oil (washed three times with pentane) in 150 mL of tetrahydrofuran at room temperature under argon was slowly added 6.15 mL (40.5 mmol, 3 eq.) of diethyl malonate. The resulting solution was stirred for 0.5 hours, then treated with a solution of 3.83 g (13.5 mmol) of farnesyl bromide in 10 mL of tetrahydrofuran. After stirring for 6 hours, the reaction was quenched with saturated NH$_4$Cl and diluted with 300 mL of diethyl ether. The organic layer was washed with two 100 mL portions of water and 100 mL of brine, dried over MgSO$_4$ and evaporated and the bulk of the diethyl malonate removed by spinning under high vacuum to afford 4.29 g (87%) of crude title product.

TLC Silica gel (ethyl acetate:hexane 1:9) R$_f$=0.37. (TLC shows slight amount of diethyl malonate and a second by-product.)

(2) (E,E)-5,9,13-Trimethyl-4,8,12-tetradecatrienoic acid, ethyl ester

A mixture of 4.103 g (11.2 mmol) of Part A$^1$(1) diester, 200 μL (11.2 mmol, 1 eq.) of water, and 950 mg (22.4 mmol, 2 eq.) of lithium chloride in 20 mL of dimethyl sulfoxide was heated at reflux (~190° C.) for four hours. After cooling, the reaction mixture was diluted with 180 mL of a 1:1 mixture of diethyl ether: petroleum ether and washed with five 50 mL portions of water and 50 mL of brine, dried over MgSO$_4$ and evaporated to yield 3.623 g of crude product as a yellow-orange oil. Kugelrohr distillation at 180° C. (meter setting) and 0.025 mm allowed the collection of 2.100 g of a pale yellow oil, which was, however, still contaminated (by TLC). The distillation, therefore, is unnecessary and *should not* be performed. Flash chromatography on 180 g of silica gel, eluted with 3:97 ethyl acetate: petroleum ether provided 1.844 g (56%) of desired title product as a pale yellow oil.

TLC Silica gel (ethyl acetate:hexanes 5:95) R$_f$=0.27.

$^1$H-NMR (CDCl$_3$, 270 MHz): δ5.08 (br, 3H), 4.12 (q, 2H, J=6.7 Hz), 2.31 (m, 4H), 2.10-1.90 (m, 8H), 1.67 (s, 3H), 1.62 (s, 3H), 1.59 (s, 6H), 1.25 (t, 3H, J=6.7 Hz), ppm.

(3) Bishomofarnesol

A solution of 7.05 g (24 mmol) of Part A[1] (2) monoester in 65 mL of dry diethyl ether at 0° C. under argon was treated in portions with 915 mg (24 mmol) of lithium aluminum hydride and stirred at room temperature for three hours. After cooling to 0° C., the reaction was quenched with 7 mL of water, 7 mL of 15% NaOH, then stirred for 15 minutes. Additional 21 mL of water was added, and the reaction was stirred 0.5 hours, then dried with $Na_2SO_4$. The mixture was filtered through Celite, washing well with diethyl ether, and evaporated to give 5.665 g of a colorless oil. Purification by flash chromatography on silica gel eluted with 15:85 ethyl acetate:petroleum ether provided 5.23 g (87%) of title compound as a colorless oil.

TLC Silica gel (2:8 ethyl acetate:hexanes) $R_f=0.21$.

IR(neat) 3330, 2964, 2926, 2873, 2858, 1448, 1384, 1107, 1059, 401 $cm^{-1}$. $^1H$-NMR ($CDCl_3$, 270 MHz): δ5.10 (m, 3H), 3.63 (t, 2H, J=6.5 Hz), 1.9–2.2 (m, 1OH), 1.68 (s, 3H), 1.62 (s, 3H), 1.60 (s, 6H), ppm.

Mass Spec ($CI-CH_4/N_2O$, +ions) m/e 251 (M+H), 249 (M+H-$H_2$), 137, 123, 109, 69.

B. (E,E)-5,9,13-Trimethyl-4,8,12-tetradecatrien-1-ol, methanesulfonate ester To a stirred solution of 2.02 g (8.07 mmol) of bishomofarnesol (prepared as described in Example 1, Part A) in 20 mL of dichloromethane at 0° C. was added 2.2 mL (16.1 mmol) of triethylamine followed by 0.69 mL (8.90 mmol) of methanesulfonyl chloride, dropwise over 15 minutes. After stirring for 1.5 hours at 0° C., the reaction was diluted with dichloromethane, washed with 20 mL each of 10% HCl, saturated $NaHCO_3$ and brine, dried ($MgSO_4$) and evaporated to give 2.71 g (100%) of the crude title mesylate as a colorless oil.

TLC Silica gel ($CH_2Cl_2$) $R_f=0.46$.

$^1H$ NMR ($CDCl_3$, 270 MHz): δ5.09 (t, 3H, J=6.5 Hz), 4.21 (t, 2H, J=7.0 Hz), 2.99 (s, 3H), 2.20–1.90 (m, 1OH), 1.78 (quint, 2H, J=7.0 Hz), 1.65 (s, 3H), 1.61 (s, 3H), 1.60 (s, 6H).

C. (E,E)-14-Iodo-2,6,10-trimethyl-2,6,10-tetradecatriene

The crude Example 1, Part B, mesylate prepared from 441.1 mg (1.76 mmol) of the corresponding alcohol according to the procedure of Example 1, Part B, was dissolved in 5 mL of acetone and treated with 530 mg (3.52 mmol) of sodium iodide. The reaction was allowed to stir for 16 hours at room temperature followed by 5 hours at reflux. The suspension was diluted with hexane and stirred with dilute aqueous sodium bisulfite to discharge to yellow color. The organic layer was washed with water and brine, dried ($MgSO_4$), and evaporated to provide 577 mg of crude product. Flash chromatography on 35 g of silica gel eluted with hexane gave 550.9 mg (87%) of title iodide as a colorless liquid.

TLC Silica gel (hexane) $R_f=0.31$.

$^1H$ NMR ($CDCl_3$, 270 MHz): δ5.09 (m, 3H), 3.16 (t, 2H, J=7.0 Hz), 2.20–1.90 (m, 12H), 1.85 (quint., 2H, J=6.5 Hz), 1.67 (s, 3H), 1.63 (s, 3H), 1.59 (s, 6H) ppm.

Mass Spec ($CI-CH_4/N_2O$+ions) m/e 361, 359 (M+H), 137.

D. (E,E)-(6,10,14-Trimethyl-5,9,13-pentadecatrienylidene)bisphosphonic acid, tetraethyl ester A suspension of 2.40 g (100.0 mmol) of NaH in 100 mL of dry dimethylformamide (DMF) at 0° C. under argon was treated with 28.8 g (100.0 mmol) of tetraethyl methylenediphosphonate in 25 mL of DMF over 0.8 hours to give a yellow solution. The reaction was allowed to warm to room temperature and stir for 0.5 hours when 12.0 g (33.0 mmol) of Part C iodide was added in one portion. The reaction mixture was stirred for 6 hours at room temperature when 85 mL of DMF were removed by vacuum distillation (bath temperature 50° C., pressure ~1 mm Hg). The reaction was quenched with 7.0 mL (112.0 mmol) of glacial acetic acid and the resulting slurry diluted with water (100 mL) and extracted with ethyl acetate (200 mL). The organic layer was washed with brine, dried over $Na_2SO_4$ and concentrated to provide a thick oil. The combined aqueous fractions were reextracted with two portions of ethyl acetate. The combined organic layers were washed twice with brine, dried ($Na_2SO_4$) and evaporated to provide a crude yellow oil. The combined oils were purified by flash chromatograph on 1500 g of silica gel packed and loaded with ethyl acetate, eluted with 700 mL of ethyl acetate, then 2.5 1 of 1:7 ethanol/ethyl acetate to provide 13.5 g (78%) of title compound in the form of a pale yellow oil.

TLC Silica gel (1:9 ethanol:ethyl acetate) $R_f=0.53$.

$^1H$ NMR ($CDCl_3$, 270 MHz): δ5.15 (m, 3H), 4.12 (quint., 8H, J=7.0 Hz), 2.30 (tt, 1H, J=24.2, 6.0 Hz), 2.10–1.80 (m, 12H), 1.70 (s, 3H), 1.65 (m, 2H), 1.60 (s, 9H), 1.45 (t, 12H, J=7.0 Hz) ppm.

E. (E,E)-(6,10,14-Trimethyl-5,9,13-pentadecatrienylidene)bisphosphonic acid, trisodium salt To a stirred solution of 2.0 g (3.84 mmol) of Example 1, Part D compound, in 20 mL of dichloromethane at 0° C. was added 1.40 g (11.5 mmol, 3 eq.) of 2,4,6-collidine followed by 2.93 g (19.2 mmol) of bromotrimethylsilane. The reaction was allowed to stir at room temperature for 12 hours when the solvent was evaporated and the semisolid residue pumped (~1 mm pressure) for 0.5 hour. The residual material was dissolved by adding 40 mL (20.0 mmol) of 0.5 N NaOH solution and the solution freeze dried. The crude white lyophilate was purified by MPLC on a column of CHP20P gel (0.5 L of gel) eluting with water (1.0L) followed by 20% acetonitrile in water (1.5 L). Approximately 75 mL fractions were collected. The pure fractions were combined and the acetonitrile was removed under reduced pressure. The remaining aqueous solution (~125 mL volume) was eluted through 100 mL of Chelex resin (Na form), filtered through a 0.2 μm nylon filter and lyophilized to provide 1.36 g (75%) of title compound as a white lyophilate.

IR (KBr) 3432, 2965, 2924, 2858, 1635, 1449, 1097, 881 $cm^{-1}$.

$^1H$ NMR ($D_2O$, 400 MHz): δ 5.25 (t, 1H, J=7.0 Hz), 5.15 (m, 2H), 2.15–1.90 (m, 1OH), 1.70 (m, 3H), 1.63 (s, 3H), 1.58 (s, 3H), 1.53 (s, 6H), 1.50 (m, 2H) ppm.

Mass Spec. (FAB) m/e 519 (M+2Na-H), 497 (M+Na), 475 (M+H), 453 (M-Na+2H).

Anal. Calc'd for C +2.00 $H_2O$: C, 42.37; H, 6.91; P, 12.14 Found: C, 42.24; H, 6.96; P, 12.52

EXAMPLE 2

(E,E)-(6,10,14-Trimethyl-5,9,13-pentadeca-trienylidene)bisphosphonic acid, diethyl ester, dipotassium salt To a stirred solution of 0.30 g (0.57 mmol) of Example 1, Part D compound in 3mL of ethanol was added 3.60 mL (3.60 mmol) of 1M KOH solution. The reaction was refluxed exhaustively over a period of 48 hours. The remaining ethanol was removed under reduced pressure and the aqueous fraction was diluted with 5 mL of water and lyophilized.

The crude solids were purified by MPLC on a column of CHP20P gel (2.5 cm diameter × 10 cm height) eluted with water (150 mL) followed by a gradient created by the gradual addition of 400 mL of acetonitrile to a reservoir of 350 mL of water. Approximately 12 mL fractions were collected. The acetonitrile was removed under reduced pressure and the aqueous solution lyophilized to provide 0.195 g (63%) of title compound as white lyophilate.

TLC Silica gel (7:2:1 n-propanol: conc. ammonia: water) $R_f=0.30$.

IR (KBr) 3364, 3276, 2975, 2931, 1674, 1446, 1385, 1203, 1087, 1053, 941 cm$^{-1}$.

$^1$H NMR (D20: CD30D 1:1, 270 MHz, 50° C.): δ5.26 (t, 1 H, J=6.5 Hz), 5.20 (t, 2H, J=5.9 Hz), 4.00 (m, 4 H), 2.10–1.80 (m, 13H), 1.75 (s, 3H), 1.70 (m, 2H), 1.69 (s, 3H), 1.57 (s, 6H), 1.33 (t, 6H, J=7.0 Hz) ppm.

Mass Spec (FAB) m/e 579 (M+K), 541 (M+H), 503 (M-K+2H).

Anal. Calc'd for $C_{22}H_{40}O_6K_2P_2 + 1.25\ H_2O$: C, 46.92; H, 7.61; P, 11.00 Found: C, 46.95; H, 7.90; P, 11.19.

EXAMPLE 3

(E)-(10,14-Dimethyl-9,13-pentadecadienylidene)bisphosphonic acid, trisodium salt

A. Dichloro[μ-[1-hexanolato(2- C$^6$:O$^1$]]dimagnesium

To a stirred solution of 11.00 g (80.0 mmol) of 6-chloro-1-propanol (Aldrich) in 20 mL of THF at −20° C. was added 27.0 mL (81.0 mmol) of 3.0 M methylmagnesium chloride in THF dropwise over 25 minutes. After 0.5 hours at −20° C., the reaction was allowed to warm to room temperature and 2.88 g (118.0 mmol) of magnesium turnings were added and the reaction was heated to reflux. The reaction was initiated by adding a few crystals of iodine at the start of reflux and after 1 hour of heating. After 2 hours at reflux the reaction was cooled to room temperature providing the Grignard solution. The molarity of the reaction mixture was determined by titration: 5.20 mL (2.60 mmol) of a 0.5 M solution of 2-propanol in benzene was slowly added to a blood red solution of 2-2'-biquinoline (indicator) in benzene and 2.0 mL of the freshly prepared Grignard solution The endpoint color was light green and the molarity was determined to be 1.3M.

B. (E)-9,13-Dimethyl-8,12-tetradecadien-1-ol

A solution of 21.5 mL (28.0 mmol) of 1.3M Part A Grignard reagent in THF and 5.0 mL of HMPA at 0° C. was treated dropwise with 1.21 g (7.0 mmol) of geranyl chloride in 7 mL of THF over 7 minutes. After the addition the reaction was allowed to warm to room temperature and stir for 2 hours, at which point the reaction was diluted with ether and quenched with 50 mL (50.0 mmol) of 1M HCl solution. The organic layer was washed two times with NH4Cl solution, dried over MgSO4 and evaporated to provide a crude oil. Flash chromatography was performed on 125 g of silica gel packed, loaded and eluted with 1:4 ethyl acetate/hexanes to provide 1.10 (66%) of title alcohol as an amber oil.

TLC Silica gel (1:9 ethyl acetate:hexane) $R_f=0.20$.

IR (CCl4 solution) 3636, 2928, 2854, 1450, 1377, 1055 cm$^{-1}$.

$^1$H NMR (CDC13, 270 MHz): δ5.40 (q, 2H, J=7.0 Hz), 3.69 (t, 2H, J=7.0 Hz), 2.25–1.85 (m, 8H), 1.75 (s, 3H), 1.70 (s, 6H), 1.65 (m, 2H), 1.39 (s, 7H) ppm.

MS (Ci, NH3, +ions) 256 (M+NH4).

C. (E)-9,13-Dimethyl-8,12-tetradecadien1-yl iodide

To a stirred solution of 1.10 g (4.62 mmol) of Part B alcohol and 1.40 mL (10.00 mmol) of triethylamine in 10 mL of methylene chloride at 0° C. was added 0.37 mL (4.80 mmol) of methanesulfonyl chloride dropwise over 15 minutes. After 1 hour at 0° C. the reaction was diluted with ether and washed with aqueous solutions of NH4Cl, NaHCO3, and brine. The organic layer was dried (MgSO4) and concentrated under reduced pressure to provide 1.42 g (~4.5 mmol) of the crude mesylate. The residual oil was dissolved in 25 mL of acetone and treated with 3.00 g (20.0 mmol) of NaI. The resulting suspension was heated to reflux for 4 hours and diluted with ether, washed with brine, dried over MgSO4, and concentrated to provide a yellow oil. Flash chromatography was performed on 100 g of silica gel packed, loaded and eluted with hexanes to provide 1.10 g (68% overall yield) of title iodide in the form of a colorless oil.

TLC Silica gel (hexanes) $R_f=0.45$.

IR (CC14 solution) 2962, 2928, 2854, 1450, 1375 cm$^{-1}$.

$^1$H NMR (CDC13, 270 MHz): δ5.41 (q, 2H, J=7.0 Hz), 3.47 (t, 2H, J=7.0 Hz), 2.40–2.20 (m, 6H), 2.11 (quint, 2H, J=7.0 Hz), 1.97 (s, 3H), 1.89 (s, 6H), 1.60 (m, 8H) ppm.

MS (CI, NH3, +ions) 366 (M+NH4), 348 (M).

D. (E)-(10,14-Dimethyl-9,13-pentadecadienyldene)bisphosphonic acid, tetraethyl ester To a suspension of 151 mg (6.32 mmol) of NaH in 3 mL of dry DMF and 10 mL of dry THF at 0° C. under argon was added 1.82 g (6.32 mmol) of tetraethyl methylenediphosphonate over 10 minutes to give a yellow solution. The reaction was allowed to warm to room temperature and stir for 0.5 hours when 1.10 g (3.16 mmol) of Part C iodide was added in one portion. The reaction mixture was stirred for 18 hours when it was quenched with saturated aqueous NH4Cl solution and diluted with ethyl acetate. The organic fraction was washed with brine, dried over Na2SO4 and evaporated to provide a crude yellow oil. Flash chromatography was performed on 100 g of silica gel packed and loaded with ethyl acetate and eluted with 400 mL of ethyl acetate followed by 1:9 ethanol/ethyl acetate collecting in 40 mL fractions. The solvent was removed under reduced pressure to provide 1.03 g (64%) of title compound in the form of a pale yellow oil.

TLC Silica gel (1:9 ethanol/ethyl acetate) $R_f=0.37$.

IR (CCl4 solution) 2980, 2928, 2854, 1442, 1250, 1030, 967 cm$^{-1}$.

$^1$H NMR (CD30D, 270 MHz): δ5.15 (q, 2H, J=7.0 Hz), 4.19 (quint. d, 8H, J=7.0, 2.3 Hz), 2.47 (tt, 1 H, J=24.0, 5.9 Hz), 2.10-1.80 (m, 8H), 1.66 (s, 3H), 1.59 (s+m, 8H), 1.34 (t, 12H, J=7.0 Hz), 1.31 (m, 8H) ppm.

MS (CI, NH$_4$, +ions) 526 (M+NH$_4$), 509 (M+H).

E.
(E)-(10,14-Dimethyl-9,13-pentadecadienylidene)bisphosphonic acid, trisodium salt To a stirred solution of 1.00 g (1.96 mmol) of Part D compound in 10 mL of dichloromethane at room temperature was added 1.06 mL (8.00 mmol) of 2,4,6-collidine followed by 1.32 mL (10.00 mmol) of bromotrimethylsilane. The reaction was allowed to stir at room temperature for 13 hours when the solvent was evaporated and the semisolid residue pumped (~1 mm pressure) for 0.5 hours. The residue was dissolved by adding 20 mL of 0.5 N NaOH solution (10.0 mmol), diluted with 15 mL of water and freeze dried. The crude white solids were purified by MPLC on a column of CHP20P (2.5 cm diam. ×25 cm height) eluting with water (150 mL) followed by a gradient created by the gradual addition of 400 mL acetonitrile to a reservoir of 350 mL of water. Approximately 15 mL fractions were collected. The acetonitrile was removed under reduced pressure and the aqueous solution was lyophilized to provide 0.72 g (77%) of title compound.

IR (KBr) 3448, 2965, 2924, 2854, 1635, 1454, 1116, 866 cm$^{-1}$.

$^1$H NMR (D$_2$O, 400 MHz): δ5.18 (t, 1 H, J=8.0 Hz), 5.12 (t, 1 H, J=7.0 Hz), 2.05 (m, 2H), 1.96 (m, 4H), 1.65 (m, 3H), 1.62 (s, 3H), 1.54 (s, 6H), 1.45 (s broad, 2H), 1.25 (s broad, 8H) ppm.

Mass Spec. (FAB, +ions) m/e 485 (M+Na), 463 (M+H), 441 (M-Na+2H), 445 (M-H$_2$O+H).

Anal. Calc'd for C$_{17}$H$_{31}$O$_6$Na$_3$P$_2$+1.50. H$_2$O: C, 41.73; H, 7.00; P, 12.66 Found: C, 41.72; H, 6.94; P, 12.75.

EXAMPLE 4
(E,E)-(7,11,15-Trimethyl-6,10,14-hexadecatrienylidene)bisphosphonic acid, trisodium salt A. (E,E)-6,10,14-Trimethyl-5,9,13-pentadecatrien-1-yl iodide (1) (E,E)-1-Chloro-3,7,11-trimethyl-2,6,10-dodecatriene (Note: all temperatures indicated are for the contents of the reaction flask). To a stirred solution of 299 mg (2.24 mmol) of N-chlorosuccinimide in 15 mL of dichloromethane at −30° C. under argon was added 0.18 mL (2.45 mmol) of distilled dimethyl sulfide over 5 minutes. After 10 minutes at −30° C., the reaction was allowed to warm to 0° C. for 10 minutes, followed by cooling to −40° C. A solution of 441.4 mg (1.99 mmol) of 3,7,11-trimethyl-2,6,10-tridecatrien-1-ol in 5 mL of dichloromethane was added dropwise over 10 minutes. The reaction was allowed to warm gradually to 0° C. over 1 hour, and then maintained for 1 hour. After quenching with cold water, the mixture was extracted with hexane and the hexane extract was washed with cold water and cold brine, dried (MgSO$_4$) and evaporated to afford 483 mg of a crude product. Rapid flash chromatography on 20 g of silica gel eluted with 3:97 ethyl acetate:petroleum ether provided 406.5 mg (85%) of a colorless liquid. $^{13}$C NMR indicated that this material contained a trace (3%) impurity.

TLC: Silica gel (2:98 ethyl acetate:hexane) R$_f$=0.56.

$^1$H NMR (CDC13, 270 MHz): δ5.44 (t, 1 H, J=7.9 Hz), 5.09 (t, 2H, J=5.8 Hz), 4.07 (d, 2H, J=7.9 Hz), 2.20-1.90 (m, 8H), 1.72 (s, 3H), 1.68 (s, 3H), 1.60 (s, 6H) ppm.

(2) Dichloro[mu-[1-propanolato(2-)C$^3$:O$^1$]]dimagnesium

A modification of the procedure of G. Cahiez et al was employed (Tetrahedron Letters, 1978, 3013-4): To a stirred solution of 28.55 g (301.9 mmol) of 3-chloro-1-propanol in 300 mL of THF under argon at −20° C. was added 101 mL (303 mmol) of 3M methylmagnesium chloride in THF over 20 minutes. After 30 minutes at −20° C., the reaction was allowed to warm to room temperature, 11.0 g (452.8 mmol) of magnesium turnings were added and the reaction was heated to reflux. At the start of reflux, 0.60 mL (6.94 mmol) of 1,2-dibromoethane were added, and after 1 hour at reflux another 0.60 mL was added. After refluxing for a total of 2 hours, the reaction was allowed to cool to room temperature.

(3) (E,E)-6,10,14-Trimethyl-5,9,13-pentadecatrien-1-ol

A solution of 37.5 mL (20.3 mmol, 5.1 eq.) of a 0.54M solution of Grignard reagent (Part 2) in tetrahydrofuran and 9 mL of hexamethylphosphoramide at room temperature under argon was treated over 10 minutes with a solution of 955.5 mg (3.97 mmol) of (E,E)-farnesyl chloride (Part (1)) in 5 mL of tetrahydrofuran. After one hour, the reaction mixture was diluted with a mixture of 1:1 diethyl ether:hexane and quenched with 1M HCl. The organic phase was washed with three 25 mL portions of saturated NaHCO$_3$, three 25 mL portions of H$_2$O, and 25 mL of brine, dried over MgSO$_4$ and evaporated to obtain 995.0 mg of crude product. Purification required two chromatographies. The first was run on 70 g of silica gel, eluting with 1:99 ethyl acetate:CH$_2$Cl$_2$ to provide 484.3 mg of impure material and 307.7 mg of pure title compound. The second chromatography, of the impure fractions, on 50 g of silica gel eluted with 0.75:99.25 ethyl acetate: CH$_2$Cl$_2$ gave 117.2 mg of slightly impure material and 302.8 mg of pure title compound. Combination of pure material from both columns gave a yield of 610.5 mg (58%) of pure desired title isomer.

TLC: Silica gel (10:90 ethyl ether:CH ) R$_f$=0.38.

IR (CCl$_4$) 3639, 3450, 2964, 2930, 2858, 1449, 1382, 1058, 1028, 776, 750 cm$^{-1}$.

$^1$H NMR (CDC13, 270 MHz): δ5.10 (m, 3H), 3.62 (t, 2H, J=6.5 Hz), 2.00 (m, 10H), 1.69 (s, 3H), 1.61 (s, 9H), 1.70-1.20 (m, 5H), ppm.

Mass Spec (CI-CH$_4$/N$_2$O, +ions) m/e 282 (M+NH$_4$), 265 (M+H), 263 (M+H-H$_2$).

(4) (E,E)-6,10,14-Trimethyl-5,9,13-pentadecatrien-1-yl iodide

To a stirred solution of 363.8 mg (1.38 mmol) of Part (3) alcohol in 6 mL of dichloromethane at 0° C. was added 0.39 mL (2.76 mmol) of triethylamine followed by the dropwise addition of 0.14 mL (2.76 mmol) of methanesulfonyl chloride over 5 minutes. After stirring for 1 hour at 0° C., the mixture was diluted with ether and the organic phase was washed with 10% HCl, water, saturated NaHCO$_3$ and brine, dried (MgSO$_4$) and evaporated to give 458.8 mg of the mesylate as a colorless oil.

The crude mesylate was dissolved in 10 mL of acetone, treated with 414 mg (2.76 mmol) of sodium iodide and heated to 40° C. under argon for 17 hours. The mixture was diluted with hexane, washed with water, 4% sodium thiosulfate, water and brine, dried (MgSO$_4$), evaporated to provide a colorless oil. Flash chromatography on 30 g of silica gel eluted with hexane gave 466.6 mg (90%) of the pure title iodide as a colorless oil.

TLC: Silica gel (Hexane) $R_f=0.32$.

IR (CCl$_4$) 2965, 2927, 2854, 1449, 1381, 1222, 809 cm$^{-1}$.

$^1$H NMR (CDCl, 270 MHz): δ5.10 (m, 3H), 3.18 (t, 2H, J=7 Hz), 2.00 (m, 10H), 1.82 (quint, 2H, J=7 Hz), 1.68 (s, 3H), 1.60 (s, 9H), 1.44 (m, 2H) ppm. Mass Spec (CI-CH$_4$/N$_2$O, +ions) m/e 392 (M+NH$_4$), 375 (M+H).

B.
(E,E)-(7,11,15-Trimethyl-6,10,14-hexadecatrienylidene)bisphosphonic acid, tetraethyl ester To a solution of 140 mg (5.83 mmol) of NaH in 3 mL of dry DMF and 7 mL of dry THF at 0° C. under argon was treated with 1.64 g (6.40 mmol) of tetraethyl methylenediphosphonate over 10 minutes to give a yellow solution. The reaction was allowed to warm to room temperature and stir for 0.5 hours when 0.70 g (1.87 mmol) of Part A iodide was added in one portion. The reaction mixture was stirred for 18 hours when it was quenched with saturated aqueous NH$_4$Cl solution and diluted with ethyl acetate. The organic fraction was washed with water, brine and dried over Na$_2$SO$_4$ and evaporated to provide a crude yellow oil. Flash chromatography was performed on 100 g of silica gel packed and loaded with ethyl acetate. Elution with 200 mL of ethyl acetate followed by 1:9 ethanol/ethyl acetate collecting in 40 mL fractions provided 0.74 g (74%) of title compound in the form of a pale yellow oil.

TLC Silica gel (1:9 ethanol:ethyl acetate) $R_f=0.56$.

$^1$H NMR (CDCl 270 MHz): δ 5.15 (m, 3H), 4.12 (quint., 8H, J=7.0 Hz), 2.30 (tt, 1H, J=24.2, 6.0 Hz), 2.15–1.80 (m, 12H), 1.67 (s, 3H), 1.59 (s, 9H), 1.57 (m, 2H), 1.39 (t, 12H, J=6.0 Hz) ppm.

Mass Spec (CI-NH$_3$) 535 (M+H), 552 (M+NH$_4$).

C.
(E,E)-(7,11,15-Trimethyl-6,10,14-hexadecatrienylidene)bisphosphonic acid, trisodium salt To a stirred solution of 0.74 g (1.38 mmol) of Part B compound in 10 mL of dichloromethane at room temperature was added 0.71 mL (5.36 mmol) of 2,4,6-collidine followed by 0.97 mL (6.99 mmol) of bromotrimethylsilane. The reaction was allowed to stir at room temperature for 6 hours when the solvent was evaporated and the semisolid residue pumped (~1 mm pressure) for 0.5 hours. The residue was dissolved by adding 11 mL of 0.5 N NaOH solution (5.5 mmol), diluted with 15 mL of water and freeze dried. The crude white solids were purified by MPLC on a column of CHP20P (2.5 cm diam.×15 cm height) eluting with water (150 mL) followed by a gradient created by the gradual addition of 400 mL acetonitrile to a reservoir of 350 mL of water. Approximately 15 mL fractions were collected. The acetonitrile was removed under reduced pressure and the aqueous solution was lyophilized to provide 0.47 g (70%) of title compound as a white lyophilate. The white solids were further purified by MPLC on a column of CHP20P gel eluting with water, followed by 20% acetonitrile in water. The pure fractions were combined and freeze dried to yield 0.18 g (30%) of title compound as a white lyophilate.

IR (KBr): 3426, 2965, 2925, 2856, 1634, 1449, 1100, 880 cm$^{-1}$. $^1$H NMR (D$_2$O, 400 MHz): δ5.25 (t, 1H, J=6.4 Hz), 5.15 (q, 2H, J=5.5 Hz), 2.15–1.90 (m, 10H), 1.70 (m, 3H), 1.63 (s, 3H), 1.57 (s, 3H), 1.56 (s, 6H), 1.50 (m, 2H), 1.30 (m, 2H) ppm.

Mass Spec (FAB) m/e 511 (M+Na), 489 (M+H), 467 (M-Na+2H), 445 (M-2Na+3H).

Anal. Calc'd for C$_{19}$H$_{33}$O$_6$Na$_3$P$_2$+1.0 H$_2$O: C, 45.07; H, 6.97; P, 12.23 Found: C, 45.15; H, 6.81; P, 12.06.

EXAMPLE 5
(E)-(6,10-Dimethyl-5,9-undecadienylidene)bisphosphonic acid, tetrasodium salt

A. (E)-8-Chloro-2,6-dimethyl-2,6-octadiene

To a stirred solution of 30.0 g (0.194 mol) of (E)-3,7-dimethyl-2,6-octadien-1-ol and 28.27 mL (0.213 mol) of 2,4,6-collidine under argon at room temperature was added dropwise 8.23 g (0.194 mol) of lithium chloride in 100 mL of DMF. The mixture was cooled to 0° C and treated with 16.56 mL (0.213 mmol) of methanesulfonyl chloride dropwise over 10 minutes. The reaction was stirred at 0° C. for 1.5 hours (solid present), then was poured into 500 mL of ice/water. The aqueous solution was washed three times with 200 mL portions of hexane, the organic layers were combined and washed with 5% KHSO$_4$, water, NaHCO$_3$, brine, dried (MgSO$_4$) and evaporated to provide 29.95 g of a pale yellow oil. Rapid flash chromatography was performed on 400 g of silica gel, eluting with 3:9 EtOAc/hexane. Pure product fractions were combined and evaporated to provide 25.20 g (75%) of title compound as a pale yellow oil.

TLC Silica gel (8:1 hexane/EtOAc) $R_f=0.68$.

$^1$H-NMR (CDCl, 270 MHz): δ5.44 (m, 1 H), 5.08 (m, 1 H), 4.09 (d, 2H, J=8.2 Hz), 2.08 (m, 4H), 1.73 (s, 3H), 1.68 (s, 3H), 1.60 (s, 3H) ppm.

B. (E)-(3,7-Dimethyl-2,6-octadienyl)propanedioic acid, diethyl ester

To a stirred solution of 14.68 g (0.611 mol) of NaH (100%) in 400 mL of THF at 0° C. under argon was added dropwise 92.76 mL (0.611 mol) of diethyl malonate in 100 mL of THF over 0.5 hours. This solution was stirred for 0.5 hours at 0° C., at which time 35.20 g (0.204 mol) of Part A chloride in 50 mL of THF was added dropwise over 15 minutes. The reaction gradually warmed to room temperature, stirred for 18 hours then was quenched with 250 mL of saturated NH$_4$Cl and diluted with 250 mL of ether. The organic layer was washed with water, brine, dried (MgSO$_4$) and evaporated to remove solvent and provide 100 g of an oil. The excess diethyl malonate was removed by distillation at 75° C. (1.5 mm) to provide 65 g of title compound also containing some dialkylated product and diethyl malonate.

TLC Silica gel (1:1 Hexane/Ethyl acetate) $R_f=0.37$.

IR (CCl4) 2982, 2926, 2854, 1751, 1734, 1446, 1369, 1332, 1269, 1236, 1209, 1149, 1111, 1095, 1035, 860 cm$^{-1}$.

$^1$H NMR (CDCl$_3$, 270 MHz): δ5.07 (q, 2H, J=7.1 Hz), 4.18 (q, 2H, J=7.0 Hz), 3.33 (t, 1H, J=7.6 Hz), 2.60 (t, 2H, J=7.3 Hz), 2.04–1.98 (m, 9H), 1.68 (s, 3H), 1.64 (s, 3H), 1.59 (s, 3H), 1.26 (t, 6H, J=7.0 Hz) ppm.

MS (CI-NH$_3$, +ions) m/e 314 (M+NH4), 297 (M+H).

C. (E)-5,9-Dimethyl-4,8-decadienoic acid, ethyl ester

To a solution of 65 g of the crude Part B diester described above, 5.40 mL (0.30 mol) of water and 25.0 g (0.60 mol) of lithium chloride in 250 mL of DMSO was heated to 190° C. and stirred for 9 hours. The reaction was treated with a 1:1 solution of hexane/ether and then washed with water and brine. The organic layer was dried (MgSO$_4$) and evaporated to provide 34.6 g of title compound in the form of a yellow oil. No further purification was performed; the sample was carried on to the next step.

TLC Silica gel (95:5 Hexane/Ethyl acetate) R$_f$=0.30.

$^1$H NMR (CDCl3, 270 MHz): δ 5.00 (m, 2H), 4.04 (q, 2H, J=7.0 Hz), 2.23 (m, 4H), 1.99-1.87 (m, 4H), 1.59 (s, 3H), 1.54 (s, 3H), 1.51 (s, 3H), 1.17 (t, 3H, J=7.0 Hz) ppm.

MS (CI-NH$_3$, +ions) m/e 242 (M+NH$_4$), 225 (M+H).

D. (E)-5,9-Dimethyl-4,8-decadien-1-ol

To a stirred solution of 5.84 g (0.154 mol) of lithium aluminum hydride in 700 mL of ether at 0° C. under argon was added dropwise 34.50 g of crude Part C ester over 20 minutes. The mixture was stirred for 1.5 hours at which time it was quenched by the following: 5.8 mL (0.324 mol) of water, 5.8 mL of 15% NaOH in water and then 17.5 mL (0.973 mol) of water. The granular solution was stirred and dried (MgSO$_4$) for 0.5 hours at which time the mixture was filtered through a celite cake and washed with ether followed by dichloromethane. The filtrate was evaporated to provide 28.16 g of an oil that was distilled using a shortpath apparatus (bp 95°-96° C., 0.3 mm) to provide 20.5 g (55% overall from Part A chloride) of title alcohol as a colorless oil.

TLC Silica gel (Dichloromethane) R$_f$=0.11.

IR (CCl4) 3620, 3340, 2966, 2924, 2877, 2856, 2729, 1670, 1446, 1377, 1350, 1278, 1199, 1155, 1107, 1057, 985, 829, 814, 792 cm$^{-1}$.

$^1$H NMR (CDCl$_3$, 270 MHz): δ 5.10 (m, 2H), 3.62 (t, 2H, J=6.5 Hz), 2.11-1.94 (m, 7H), 1.67-1.58 (m, 2H), 1.67 (s, 3H), 1.61 (s, 3H) ppm.

MS (CI-NH$_3$, +ions) m/e 200 (M+NH$_4$), 183 (M+H).

E. (E)-5,9-Dimethyl-4,8-decadien-1-ol, methanesulfonate ester

To a stirred solution of 12.0 g (65.93 mmol) of Part D alcohol in 200 mL of dichloromethane at 0° C. under argon was added 11.95 mL (85.71 mmol) of triethylamine and 6.12 mL (79.11 mmol) of methanesulfonyl chloride. The reaction was stirred for 1 hour then was diluted with ether and washed with 5% KHSO$_4$, saturated NaHCO$_3$ and brine. The organic layer was dried (MgSO$_4$) and evaporated to provide 16.91 g (98%) of title methanesulfonate as a pale yellow oil.

TLC Silica gel (Dichloromethane) R$_f$=0.53.

IR (CCl4) 2963, 2927, 2922, 2882, 2875, 2856, 1455, 1450, 1381, 1363, 1347, 1178, 1007, 969, 957, 929, 793, 785, 758 cm$^{-1}$.

$^1$H NMR (CDCl3, 270 MHz): δ 5.09 (m, 2H), 4.21 (t, 2H, J=6.5 Hz), 2.98 (s, 3H), 2.13-1.99 (m, 6H), 1.79 (quint., 2H, J=6.7 Hz), 1.68 (s, 3H), 1.61 (s, 3H), 1.60 (s, 3H) ppm.

MS (CI-NH$_3$, +ions) m/e 278 (M+NH$_4$).

F. (E)-(E)-5,9-Dimethyl-4,8-decadien-1-yl iodide

To a stirred solution of 16.91 g (65.04 mmol) of Part E methanesulfonate in 500 mL of acetone at room temperature under argon was added 39.00 g (260.16 mmol) of sodium iodide. The reaction mixture was refluxed for 3.5 hours, then diluted with 400 mL of a 1:1 mixture of water/hexane. The organic layer was washed with saturated sodium sulfite, dried (MgSO$_4$) and evaporated to provide 17.57 g of a pale yellow oil. The oil residue was filtered through 400 g of silica gel eluting with hexane. The pure product fractions were combined and evaporated to provide 16.86 g (89%) of title iodide as a colorless oil.

TLC Silica gel (Hexane) R$_f$=0.37.

IR (CCl4) 2962, 2924, 2852, 1444, 1375, 1342, 1261, 1226, 1201, 1163, 1107, 983, 873, 835, 819, 761, 742 cm$^{-1}$.

$^1$H NMR (CDCl3, 270 MHz): δ5.07 (t, 2H, J=7.0 Hz), 3.18 (t, 2H, J=7.0 Hz), 3.14-1.96 (m, 6H), 1.86 (quint., 2H, J=7.0 Hz), 1.68 (s, 3H), 1.63 (s, 3H), 1.60 (s, 3H) ppm.

MS (CI-NH$_3$, +ions) m/e 310 (M+NH$_4$).

G. (E)-(6,10-Dimethyl-5,9-undecadienylidene)bisphosphonic acid, tetraethyl ester To a stirred solution of 3.21 g (133.56 mmol) of sodium hydride (100%) in 100 mL of DMF at 0° C. under argon was added dropwise 33.21 mL (133.56 mmol) of tetraethyl methylenediphosphonate. The mixture was stirred for 0.5 hours then was treated with 13.00 g (44.52 mmol) of Part F iodide in 5 mL of DMF. The reaction was stirred for 1 hour at 0° C. then at room temperature for 18 hours, at which time the reaction was quenched with saturated NH$_4$Cl and diluted with ether. The organic layer was washed with water, brine, dried (MgSO$_4$) and evaporated to provide 18.09 g of a yellow oil. Flash chromatography was performed on 1000 g of silica gel eluting with EtOAc (1000 mL), 49.5:49.5:1 acetone/EtOAc/methanol (1000 mL), followed by 47.5:47.5:5 acetone/EtOAc/methanol (2000 mL). Approximately 40 mL fractions were collected. Product fractions were collected and purified further on 600 g of silica eluting with 97:3 CH$_2$Cl$_2$/methanol (1000 mL) followed by 95:5 CH$_2$Cl$_2$/methanol. Pure product fractions were combined and evaporated to provide 12.62 g (63%) of title tetraethyl ester as a pale yellow oil.

TLC Silica gel (5:95 Methanol/Dichloromethane) R$_f$=0.28.

IR (CCl4) 2981, 2930, 2915, 2868, 1444, 1392, 1252, 1164, 1098, 1046, 1028, 968, 786, 763 cm$^{-1}$.

$^1$H NMR (CDCl3, 270 MHz): δ5.10 (q, 2H, J=7.0 Hz), 4.18 (m, 8H), 2.28 (tt, 1H, J=5.6, 24.0 Hz), 2.07-1.60 (m, 10H), 1.68 (s, 3H), 1.60 (s, 6H), 1.34 (t, 12H, J=7.3 Hz) ppm.

MS (CI-NH$_3$, +ions) m/e 470 (M+NH$_4$), 453 (M+H).

H. (E)-(6,10-Dimethyl-5,9-undecadienyl)bisphosphonic acid, tetrasodium salt

To a stirred solution of 5.0 g (11.06 mmol) of Part G tetraethyl ester in 100 mL of dichloromethane at room temperature under argon was added 4.38 mL (33.18 mmol) of 2,4,6-collidine followed by 8.76 mL (66.36 mmol) of bromotrimethylsilane and the reaction stirred at room temperature for 24 hours. The solvent was evaporated and pumped on under high vacuum for 2 hours. The remainder was treated with 49.77 mL (49.77 mmol) of 1 M NaOH, diluted with H$_2$O and lyophilized. The crude lyophilate was precipitated by dissolving the sample in 30 mL of water, warming to 50° C., treating the solution with 20 mL of acetone and placing the mixture in an ice bath. The solution was decanted from the gelatinous solid and the solid was treated with 40 mL of 3:1 acetone/water and allowed to stir for 10 minutes. This washing procedure was performed three times, followed by a wash with 40 mL of 4:1 acetone/water, at which point the solid was filterable. In each of the washes, the solid was broken up and "mashed" with a spatula in order to aid the washing and solidification. The solids were filtered, washed with 40 mL of 4:1 acetone/water and 40 mL of acetone, and the fine solid was pumped on by high vacuum for 18 hours to provide 3.71 g (79%) of title product as a white solid.

IR (KBr) 3432, 2924, 1639, 1450, 1096, 950 cm$^{-1}$.

$^1$H NMR (400 MHz, D$_2$O): δ5.25 (t, 1H, J=7.0 Hz), 5.15 (t, 1H, J=6.2 Hz), 2.10-1.95 (m, 6H), 1.45-1.65 (m, 6H), 1.60 (s, 3H), 1.55 (s, 3H), 1.53 (s, 3H) ppm.

Anal. Calc'd for $C_{13}H_{22}P_2O_6Na_4 \cdot 2.25$ mol H$_2$O: C, 33.31; H, 5.70; P, 13.22 Found: C, 33.43; H, 6.07; P, 13.47.

MS (FAB, +ions) m/e 451 (M+Na), 429 (M+H), 407 (M-Na+2H), 389 (M-Na+2H-H$_2$O).

EXAMPLE 6

(E,E)-(5,9,13-Trimethyl-4,8,12-tetradecatrienylidene)-bisphosphonic acid, trisodium salt

A. (E,E)-4,8,12-Trimethyl-3,7,11-tridecatrien-1-ol (1) (E,E)-3,7,11-Trimethyl-2,6,10-dodecatrienaldehyde [(E,E)-Farnesal]

A solution of oxalyl chloride (4.68 g, 0.037 mol) in dry CH$_2$Cl$_2$ under argon atmosphere was cooled to −65° C. A solution of 5.33 mL of dimethyl sulfoxide (DMSO) (0.68 mol) in CH$_2$Cl$_2$ (17 mL) was added rapidly, dropwise, to the cooled oxalyl chloride solution. After stirring for 7 minutes at −65° C., a 10 mL CH$_2$Cl$_2$ solution of (E,E)-farnesol (7.0 g, 0.032 mol) was added over 10 minutes to the reaction solution at −65° C.: a precipitate formed upon the addition of approximately half of the farnesol solution. After the addition of the farnesol solution was completed, the reaction was stirred at −65° C. for 25 minutes, and then 22.4 mL (0.16 mol) of triethylamine was added over 10 minutes. After stirring for an additional 15 minutes at −65° C., the reaction was warmed to room temperature, and then diluted with water (~200 mL). The resulting aqueous layer was extracted several times with CH$_2$Cl$_2$. The combined organic layers were washed once with saturated aqueous NaCl solution, once with 1% HCl, once with 5% Na$_2$CO$_3$ solution and once with saturated aqueous NaCl solution. The resulting organic layer was dried over MgSO$_4$ to give 7.05 g (100%) of a clear oil after filtration and solvent removal.

TLC Silica gel (20% ethyl acetate/hexane) R$_f$=0.34.

$^1$H NMR (CDCl$_3$, 270 MHz): δ9.98 (d, 1H, J=7 Hz), 5.88 (broad d, 1H, J=7 Hz), 5.08 (m, 2H), 2.22 (m, 4H), 2.17 (s, 3H), 2.02 (m, 4H), 1.66 (s, 3H), 1.60 (s, 6H) ppm.

$^{13}$C-NMR (CDCl$_3$) (67.8 MHz) δ191.0, 163.6, 136.5, 131.3, 127.4, 124.0, 122.4, 40.5, 39.6, 26.6, 25.6, 17.6, 17.5, 15.9 ppm.

(2) 4,8,12-Trimethyl-1,3,7,11-tridecatetraene

A suspension of methyltriphenylphosphonium iodide (8.07 g, 0.02 mole) in 61 mL of dry tetrahydrofuran (THF), under argon atmosphere was cooled to 0° C. To this suspension at 0° C. was added 9 mL (18 mmol) of phenyllithium (2.0M in diethyl ether/hexane 30:70) over 10 minutes. After the addition was complete, the reaction mixture containing excess phosphonium salt was warmed to room temperature and stirred for 40 minutes. The reaction mixture was then recooled to 0° C., and a 10 mL THF solution of the Part (1) aldehyde (4.0 g, 0.018 mol) was added over 12 minutes. After stirring for 10 minutes at 0° C., the reaction was warmed to room temperature. The reaction was quenched with CH$_3$OH after 2 hours at room temperature. The THF was removed from the reaction mixture to give a slurry which was triturated with petroleum ether, and subsequently, filtered through a Celite pad in a sintered glass funnel. The solids were then boiled in petroleum ether and refiltered as above. The resulting yellow oil was passed through 50 g of Florisil (100–200 mesh) eluted with ~400 mL of petroleum ether providing the title tetraene (3.36 g, 86%) as a clear oil after solvent removal.

TLC Silica gel (20% ethyl acetate/hexane) R$_f$=0.68.

$^1$H NMR (CDCl$_3$, 270 MHz): δ6.56 (ddd, 1H, J=17, 12, 6 Hz), 5.85 (d, 1H, J=12 Hz), 5.10 (m, 2H), 5.02 (m, 2H), 2.05 (m, 8H), 1.75 (s, 3H), 1.67 (s, 3H), 1.60 (s, 6H) ppm.

$^{13}$C-NMR (CDCl$_3$, 67.8 MHz): δ139.3, 135.3, 133.4, 131.2, 125.5, 124.3, 123.9, 114.5, 39.9, 39.7, 26.8, 26.4, 25.6, 17.7, 16.6, 15.9 ppm.

(3) (E,E)-4,8,12-Trimethyl-3,7,11-tridecatrien-1-ol

Neat 2-methyl-2-butene (2.25 g, 0.032 mol) was added to a 1.0M BH$_3$-THF solution (16.9 ml) at −50° C. and under argon. After the addition was complete, the reaction was stirred for 2 hours at 0° C. The resulting disiamylborane solution was transferred via cannula over 1 hour to a flask containing a 17 mL THF solution of Part A(2) tetraene (3.36 g, 0.015 mol) under argon atmosphere and cooled to 0° C. After the transfer was complete, the reaction was allowed to gradually warm to room temperature, and then it was stirred overnight at room temperature. The reaction mixture was cooled to 0° C., and 5.1 mL of 3N NaOH was added rapidly. After stirring for 10 minutes, the reaction mixture was cooled in an ice-salt bath and 5.1 mL of 30% H$_2$O$_2$ was added dropwise. Subsequently, the reaction was warmed to room temperature and stirred for 4 hours after which it was diluted with H$_2$O, and the resulting aqueous layer was extracted several times with ethyl ether. The combined organic layers were dried over MgSO$_4$. Purification by flash chromatography eluting with 20% ethyl acetate/hexane provided the title alcohol (2.62 g, 74%) as a clear oil.

TLC Silica gel (20% ethyl acetate/hexane) R$_f$=0.23.

IR (Film) 3340 (br), 2965, 2920, 1665, 1440, 1380, 1100, 1050 cm$^{-1}$.

$^1$H NMR (CDCl$_3$, 270 MHz): δ 5.10 (m, 3H), 3.61 (t, 2H, J=6 Hz), 2.29 (q, 2H, J=6 Hz), 2.03 (m, 8H), 1.67 (s, 3H), 1.65 (s, 3H), 1.60 (s, 6H) ppm.

$^{13}$C NMR (CDCl$_3$, 67.8 MHz): δ 138.8, 135.2, 131.2, 124.3, 123.9, 119.9, 62.4, 39.8, 39.7, 31.5, 26.7, 26.5, 25.6, 17.6, 16.1, 15.9 ppm.

B. (E,E)-4,8,12-Trimethyl-3,7,11-tridecatrien-1-ol, methanesulfonate ester

To a stirred solution of 2.0 g (8.5 mmol) of Part A compound in 25 mL of C at 0° C. under argon was added 1.5 mL (11.0 mmol) of triethylamine, a few crystals of 4-dimethylaminopyridine (catalyst), followed by 789 μL (10.2 mmol) of methanesulfonyl chloride dropwise. The mixture was stirred at 0° C. for 1 hour and then was diluted with 150 mL of ethyl ether. The organic layer was washed with KHSO$_4$, NaHCO$_3$, brine and dried over MgSO$_4$. The solvent was evaporated to provide 2.67 g (100%) of title compound as a yellow oil.

TLC: Silica gel (CH ) R$_f$=0.49.

$^1$H NMR (CDCl$_3$, 270 MHz): δ5.10 (m, 3H), 3.59 (t, 2H, J=6.7 Hz), 2.30-1.70 (m, 11 H), 1.67 (s, 3H), 1.64 (s, 3H), 1.60 (s, 6H) ppm.

C. (E,E)-4,8,12-Trimethyl-3,7,11-tridecatrien-1-yl iodide

To a stirred solution of 2.0 g (8.5 mmol) of Part B compound in 90 mL of acetone at room temperature under argon was added 2.55 g (17.0 mmol) of NaI. The mixture was refluxed at 80° C. for 4 hours, cooled to room temperature and diluted with 200 mL of 1:1 hexane:water. The organic layer was dried over MgSO4 and evaporated under reduced pressure to provide 2.5 g of title compound as a pale yellow oil. Flash chromatography was performed on 30 g of silica gel (60–200 mesh), packed, loaded and eluted with hexane. The pure product fractions were combined and evaporated to provide 1.97 g (69%) of title compound as a pale oil.

TLC: Silica gel (Hexane) $R_f=0.35$.

IR (CCl4) 2964, 2922, 2852, 1662, 1442, 1381, 1354, 1329, 1292, 1244, 1207, 1165, 1107, 983, 916, 887, 837, 815, 796, 742 cm$^{-1}$.

$^1$H NMR (270 MHz, CDCl3): δ5.10 (m, 3H), 3.10 (t, 2H, J=6.5 Hz), 2.55 (q, 2H, J=7.3 Hz), 2.10–1.00 (m, 8H), 1.68 (s, 3H), 1.61 (s, 3H), 1.60 (s, 6H) ppm.

MS (CI-NH3+ions) m/e 364 (M+NH4), 347 (M+H).

D.
(E,E)-(5,9,13-Trimethyl-4,8,12-tetradecatrienylidene)-bisphosphonic acid, tetraethyl ester To a stirred suspension of 209 mg (8.70 mmol) of NaH in 16.5 mL of DMF:THF (1:4.5) at 0° C. under argon was added dropwise 2.16 mL (8.70 mmol) of tetraethyl methylenediphosphonate. The mixture was stirred for 0.5 hours at 0° C., at which time 1 g (2.90 mmol) of Part C compound (neat) was added dropwise. The reaction was stirred at 0° C. for 2 hours and warmed to room temperature. After 18 hours the mixture was diluted with ether and quenched with aqueous NH4Cl. The organic layer was washed with H2O, brine, dried over MgSO4 and the solvent evaporated to provide 953 mg of a pale yellow oil. Flash chromatography was performed on 50 g of silica gel, packed, loaded and eluted with EtOAc (1 liter) and then with 1 liter of 3:97 EtOH/CH2Cl2. The pure product fractions were combined and evaporated to provide 460 mg (33%) of title compound as a pale yellow oil.

TLC Silica gel (5:95 CH3OH/CH2Cl2) $R_f=0.20$.

IR (CC14) 2978, 2928, 2912, 1442, 1390, 1251, 1163, 1097, 1026, 966, 852, 790, 763, 746 cm$^{-1}$.

$^{31}$H NMR (270 MHz, CDCl3) 5.10 (m, 3H), 4.20 (m, 8H), 2.40–2.20 (m, 3H), 2.10–1.80 (m, 10H), 1.68 (s, 3H), 1.63 (s, 3H), 1.60 (s, 6H), 1.30 (t, 12H, J=7.0 Hz) ppm.

MS (CI-NH3, +ions): m/e 507 (M+H).

E.
(E,E)-(5,9,13-Trimethyl-4,8,12-tetradecatrienylidene)-bisphosphonic acid, trisodium salt To a stirred solution of 460 mg (0.91 mmol) of Part D compound in 10 mL of CH2Cl2 at room temperature under argon was added 601 μL (4.55 mmol) of 2,4,6-collidine and 721 μL (5.46 mmol) of bromotrimethylsilane. The mixture was stirred at room temperature for 18 hours, at which time the solvent was evaporated and the residue pumped on at high vacuum for 20 minutes. The remainder was dissolved in 6.55 mL (6.55 mmol) of 1N NaOH and lyophilized. The crude material was purified by MPLC on a column of CHP20P (2.5 cm diameter ×13 cm height) eluted with water (fractions 1 to 14) followed by a gradient created by the gradual addition of 400 mL of CH3CN:H2O (75:25) to a reservoir of 400 mL of H2O, collecting approximately 15 mL fractions. Pure product fractions (#28-32) were combined and evaporated to remove CH3CN, then lyophilized to provide 343 mg (82%) of title compound as a white lyophilate.

IR (KBr) 3439, 3300, 3281, 3267, 3244, 3234, 3209, 3192, 3175, 3142, 3072, 2966, 2920, 2856, 1635, 1448, 1383, 1352, 1329, 1114, 864, 819, 771, 692, 536, cm$^{-1}$.

$^1$H NMR (400 MHz, D2O): δ5.25 (t, 1H, J=6.2 Hz), 5.17, 5.13 (two t, 1H each, J=6.6 Hz), 2.17 (m, 2H), 2.06, 1.97 (two m, 4H each), 1.75 (m, 3H), 1.62 (s, 3H), 1.60 (s, 3H), 1.56 (s, 6H) ppm.

MS (FAB, +ions) m/e 483 (M+Na), 461 (M+H), 439 (M-Na+2H), 417 (M-2Na+3H).

Anal. Calc'd for C17H29O6P2Na3·1.89 H2O): Effective MW=494.2. C, 41.30; H, 6.68; P, 12.53 Found: C, 41.32; H, 6.62; P, 12.76.

EXAMPLE 7

(E,E)-(9,13,17-Trimethyl-8,12,16-octadecatrienylidene)bisphosphonic acid, trisodium salt A.
(E,E)-(6,10,14-Trimethyl-5,9,13-pentadecatrienyl)-propanedioic acid, diethyl ester To a stirred solution of 192 mg (8.01 mmol) of NaH in 20 mL of THF at 0° C. under argon was added 1.21 mL (8.01 mmol) of diethyl malonate dropwise. The mixture was stirred at 0° C. for 0.5 hours at which time was treated with 1:0 g (2.67 mmol) of Example 4, Part A iodide in 2 mL of THF. After 1 hour at 0° C. the reaction was heated to 40° C. for 2 hours, then cooled to room temperature and stirred for 18 hours. The mixture was quenched with NH4Cl and diluted with ether. The organic layer was washed with H2O, brine, dried over MgSO4 and the solvent evaporated to provide 950 mg of a pale yellow oil. Flash chromatography was performed on 50 g of silica gel, packed, loaded and eluted with (95:5) hexane/ether. The pure product fractions were combined and evaporated to provide 580 mg (54%) of title compound as a pale yellow oil.

TLC Silica (10:90 EtOAc/Hexane) $R_f=0.41$.

$^1$H NMR (270 MHz, CDCl3) 5.10 (t, 3H, J=6.7 Hz), 4.20 (q, 4H, J=7.0), 3.30 (5, 1H, J=7.6 Hz), 2.10–1.80 (m, 12H), 1.68 (s, 3H), 1.50 (s, 9H), 1.30 (m, 4H), 1.25 (t, 6H, J=7.0 Hz), ppm.

B. (E,E)-8,12,16-Trimethyl-7,11,15-heptadecatrienoic acid, ethyl ester

To a stirred solution of 580 mg (1.43 mmol) of Part A compound and 26 μL (1.43 mmol) of H2O in 2.5 mL of DMSO was added 121 mg (2.86 mmol) of lithium chloride. The mixture was heated to 190° C. for 4 hours and diluted with a solution of ether: hexane (1:1). The organic layer was washed with H2O, brine, dried over MgSO4, and the solvent evaporated to provide 340 mg (96%) of title compound as a yellow oil.

TLC Silica (95:5 hexane/EtOAC) Rf=0.46.

$^1$H NMR (270 MHz, CDC13): δ5.05 (t, 3H, J=5.2 Hz), 4.10 (q, 2H, J=7.0), 2.20 (t, 2H, J=7.6), 1.95 (m, 10H), 1.60 (s, 3H), 1.50 (s, 9H), 1.55 (m, 2H), 1.25 (m, 4H), 1.20 (t, 3H, J=7.0 Hz).

C. (E,E)-8,12,16-Trimethyl-7,11,15-heptadecatrien-1-ol

To a stirred solution of 340 mg (1.02 mmol) of Part B compound in 6 mL of THF at 0° C. under argon was added 39 mg (1.02 mmol) of lithium aluminum hydride (exothermic). The mixture was stirred for 1.5 hours at 0° C. and was quenched slowly with the aid of a dropping funnel by the addition of: 600 μL of H$_2$O in 6 mL THF; 1.5 mL (15% NaOH) in 6 THF; 600 μL of H$_2$O. The mixture was filtered through celite and washed with ethyl acetate (EtOAc). The organics were dried over MgSO$_4$ and the solvent evaporated. The crude oil was purified on 15 g of silica gel by flash chromatography, packed, loaded and eluted with hexane:EtOAc (85:15). Pure product fractions were combined and evaporated to provide 220 mg (74%) of title compound as a pale yellow oil.

TLC Silica gel (5:95 EtOAc/hexane) R$_f$=0.10.

$^1$H NMR (270 MHz, CDCl$_3$): δ5.10 (m, 3H), 3.60 (t, 2H, J=6.4 Hz), 2.00 (m, 11H), 1.67 (s, 3H), 1.60 (s, 9H), 1.55 (m, 2H), 1.30 (m, 6H).

D.
(E,E)-8.,12,16-Trimethyl-7,11,15-heptadecatrien-1-ol, methanesulfonate ester To a stirred solution of 220 mg (0.75 mmol) of Part C compound in 5 mL of CH$_2$Cl$_2$ at 0° C. under argon was added 137 μL (0.98 mmol) of triethylamine, a few crystals of dimethylaminopyridine (as a catalyst) and 70 μL (0.90 mmol) of methanesulfonyl chloride. The mixture was stirred at 0° C. for 1 hour, then was diluted with ether and washed with KHSO$_4$, NaHCO$_3$ and brine. The organic layer was dried over MgSO$_4$ and the solvent evaporated to provide 220 mg (79%) of title compound as a pale yellow oil.

TLC Silica gel (CH ) R$_f$=0.48.

E. (E,E)-8,12,16-Trimethyl-7,11,15-heptadecatrien-1-yl iodide

To a stirred solution of 220 mg (0.595 mmol) of Part D compound in 20 mL of acetone at room temperature under argon was added 563 mg (3.76 mmol) of NaI. The mixture refluxed for 4 hours then was diluted with hexane:water (1:1). The organic layer was dried over MgSO$_4$ and the solvent evaporated to provide a pale yellow crude oil. Flash chromatography was performed on 20 g of silica gel, packed, loaded and eluted with hexane. Pure product fractions were combined and evaporated to provide 230 mg (96%) of title compound as a pale yellow oil.

TLC Silica gel (Hexane:EtOAc 80:20) R$_f$=0.91.

$^1$NMR (270 MHz, CDCl$_3$): δ5.10 (m, 3H), 3.15 (t, 2H, J=7.0 Hz), 2.00 (m, 10H), 1.80 (quint., 2H, J=7.0 Hz), 1.68 (s, 3H), 1.60 (s, 9H), 1.35 (m, 6H), ppm.

F.
(E,E)-(9,13,17-Trimethyl-8,12,16-octadecatrienylidene)bisphosphonic acid, tetraethyl ester To a stirred solution of 41 mg (1.71 mmol) of NaH in 5.5 mL of 1:4.5 DMF/THF at 0° C. under argon was added dropwise 425 μL (1.17 mmol) of tetraethyl methylenediphosphonate. The mixture was stirred at 0° C. for 0.5 hour at which time 230 mg (0.57 mmole) of Part E compound in 1 mL THF was added dropwise. The mixture was stirred at 0° C. for 1 hour, at room temperature for 18 hours, when it was diluted with ether and quenched with NH$_4$Cl. The organic layer was washed with H$_2$O, brine, dried over MgSO$_4$ and the solvent evaporated to provide a crude yellow oil. Flash chromatography was performed on 25 g of silica gel, packed, loaded and eluted with EtOAc (250 mL), 3:97 EtOH/CH$_2$Cl$_2$ (500 mL), and 5δEtOH:CH$_2$Cl$_2$ (500 mL). Pure product fractions were combined and evaporated to provide 165 mg (52%) of title compound as a pale yellow oil.

TLC Silica gel (5:95 CH$_3$OH/CH ) Rf=0.29.

$^1$H NMR (270 MHz, CDCl$_3$): δ5.05 (m, 3H), 4.10 (m, H), 2.20 (tt, 1H, J=6.1, 18.1 Hz), 1.90 (m, 14H), 1.60 (s, 3H), 1.53 (s, 9H), 1.60-1.50 (m, 2H), 1.26 (t, 12H, J=7.0 Hz), 1.30 (m, 4H) ppm.

G.
(E,E)-9,13,17-Trimethyl-8,12,16-octadecatrienylidene)-bisphosphonic acid, trisodium salt To a stirred solution of 160 mg (0.285 mmol) of Part F compound in 10 mL of CH$_2$Cl$_2$ at room temperature under argon was added 188 μL (1.43 mmol) of 2,4,6,-collidine and 226 μL (1.71 mmol) of bromotrimethylsilane. The mixture was stirred at room temperature for 18 hours, then the solution was evaporated and pumped at high vacuum for 0.5 hours. THe remainder was dissolved in 2.05 mL (2.05 mmol) of 1 N NaOH, diluted in 10 mL H$_2$O and lyophilized. The crude material was purified by MPLC on a column of CHP20P gel (2.5 cm diameter × 8cm height) eluted with H$_2$O (fractions 1 to 10 (15 mL)), followed by a gradient created by the gradual addition of 300 mL of 67:33 CH$_3$CN/H$_2$O to a reservoir of 300 mL of H$_2$O. Pure product fractions were combined, the acetonitrile was removed under reduced pressure and the aqueous solution lyophilized to provide 93 mg (63%) of title compound as a white lyophilate.

MS (FAB, +ions) m/e 539 (M+Na), 517 (M+H), 495 (M-Na+2H).

IR (KBr) 3437, 2924, 2852, 1695, 1633, 1448, 1383, 1338, 1149, 1095, 972, 875, 850, 704, 605, cm$^{-1}$.

$^1$H NMR (400 MHz, D$_2$O): δ5.19 (t, 1H, J=6.1 Hz), 5.13 (m, 2H), 2.10-1.80 (two m, 10H), 1.70 (m, 3H), 1.60 (s, 3H), 1.50 (s, 9H), 1.45 (m, 2H), 1.30 (m, 6H).

Analysis Calc'd for C$_{21}$H$_{32}$O$_6$P$_2$Na$_3$·1.75 mol H$_2$O (Effective MW=547.9) C, 46.03; H, 7.45; P, 11.31 Found: C, 46.16; H, 7.45; P, 11.07.

EXAMPLE 8
(E,E)-(6,10,14-Trimethyl-5,9,13-pentadecatrienylidene)bisphosphonic acid, tripotassium salt To a stirred solution of 2.0 g (3.84 mmol) of Example 1, Part D compound in 20 mL of dichloromethane at 0° C. was added 1.40 g (11.5 mmol, 3 eq.) of 2,4,6-collidine followed by 2.93 g (19.2 mmol) of bromotrimethylsilane. The reaction was allowed to stir at room temperature for 12 hours when the solvent was evaporated and the semisolid residue pumped (∼1 mm pressure) for 0.5 hours. The residual material was dissolved by adding 40 mL (20.0 mmol) of 0.5 N KOH solution and the solution freeze dried. The crude white lyophilate was purified by MPLC on a column of CHP20P gel (0.5 L of gel) eluting with water (1.0 L) followed by 20% acetonitrile in water (1.5 L). Approximately 75 mL fractions were collected. The pure fractions were combined and the acetonitrile was removed under reduced pressure. The remaining aqueous solution (∼125 mL volume) was eluted through 100 mL of Chelex resin (K form, 100-200 mesh), filtered through a 0.2 μm nylon filter and lyophilized to provide 0.74 g (38%) of title compound as a white lyophilate.

IR (KBr) 3427, 2966, 2924, 2861, 1699, 1662, 1448, 1398, 1258, 1113, 874 cm$^{-1}$.

43

$^1$H NMR (D$_2$O, 400 MHz): δ5.26 (t, 1H, J=7.0 Hz), 5.14 (m, 2H), 2.15–1.90 (m, 10H), 1.70 (m, 3H), 1.63 (s, 3H), 1.59 (s, 3H), 1.56 (s, 6H), 1.51 (m, H) ppm.

Mass Spec. (FAB) m/e 599 (M+2K-H), 561 (M+K), 523 (M+H), 485 (M-K+2H).

Anal. Calc'd for C$_{18}$H$_{31}$O$_6$K$_3$P$_2$+2.50 H$_2$O C, 38.08; H, 6.39; P, 10.91 Found: C, 37.91; H, 6.17; P, 11.16.

EXAMPLE 9

(E,E)-(4,8,12-Trimethyl-3,7,11-tridecatrienylidene)bisphosphonic acid, trisodium salt

20 A.

(E,E)-(4,8,12-Trimethyl-3,7,11-tridecatrienylidene)bisphosphonic acid, tetraethyl ester To a stirred mixture of 380 mg (15.80 mmol) of NaH in 10 mL of DMF at 0° C. under argon was added dropwise 3.90 mL (15.80 mmol) of tetraethyl methylenediphosphonate. The reaction was stirred for 0.5 hours, then was treated with 1.50 g (5.26 mmol) of Example 1, Part A(1) bromide. The reaction was stirred at 0° C. for 1 hour, at which time it was diluted with ether and quenched with NH$_4$Cl. The organic layer was washed with water, brine, dried (MgSO$_4$) and evaporated to provide 3.96 g of a pale yellow oil. Flash chromatography was performed on 200 g of silica gel eluted with ethyl acetate (500 mL) then with a 49.5:49.5:1 mixture of acetone/ethyl acetate/methanol. Pure product fractions were combined and evaporated to provide 1.5 g (62%) of title ester as a pale yellow oil.

IR (CCl$_4$) 2979, 2927, 2916, 2866, 1443, 1390, 1250, 1162, 1135, 1097, 1026, 967, 826, 799 cm$^{-1}$.

$^1$H NMR (270 MHz, CDCl$_3$): δ5.32 (t, 1H, J=6.7 Hz), 5.10 (m, 2H), 4.17 (quint., 8H, J=6.5 Hz), 2.64 (tt, 2H, J=6.8, 17.0 Hz), 2.31 (tt, 1H, J=6.2, 24.1 Hz), 2.15–1.90 (m, 8H), 1.68 (s, 3H, H$_{12}$), 1.65 (s, 3H), 1.60 (s, 6H), 1.34 (t, 12H, J=7.0 Hz) ppm.

MS (Cl-NH$_3$, +ions) m/e 493 (M+H).

B.

(E,E)-(4,8,12-Trimethyl-3,7,11-tridecatrienylidene)bisphosphonic acid, trisodium salt To a stirred solution of 1.50 g (3.00 mmol) of Part A ester in 20 mL of dichloromethane at room temperature under argon was added 793 μL (6.00 mmol) of 2,4,6-collidine followed by 2.00 mL (15.00 mmol) of bromotrimethylsilane. The reaction was stirred for 18 hours at room temperature, when the solvent was evaporated and the residue pumped at high vacuum for 1 hour. The remainder was dissolved in 26 mL (13.00 mmol) of 0.5 M NaOH and lyophilized. The crude lyophilate was purified by MPLC on a column of CHP20P (2.5 cm diameter ×28 cm height) eluted with water (fractions 1 to 10) followed by a gradient created by the gradual addition of 75:25 acetonitrile/water (400 mL) to a reservoir of 400 mL water. Approximately 15 mL fractions were collected. Pure product fractions were combined and evaporated to remove acetonitrile and lyophilized to provide 1.18 g (88%) of title product as a white lyophilate.

IR (KBr) 2966, 2919, 2856, 1635, 1448, 1165, 1130, 1100, 973 cm$^{-1}$.

$^1$H NMR (400 MHz, D$_2$O): δ5.45 (t, 1H, J=6.6 Hz), 5.19 (t, 1H, J=6.2 Hz), 5.14 (t, 1H, J=6.9 Hz), 2.44 (sept, 2H, J=7.5 Hz), 2.05, 1.97 (two m, 8H), 1.74 (tt, 1H, J=7.0, 21.3 Hz), 1.63 (s, 3H), 1.62 (s, 3H), 1.56 (s, 6H) ppm.

44

MS (FAB, +ions) m/e 491 (M+2Na-H), 469 (M+Na), 477 (M+H).

Anal. Calc'd for C$_{16}$H$_{27}$P$_2$O$_6$Na$_3$·1.25 mmol H$_2$O; Effective MW =468.50. C, 40.99; H, 6.34; P, 13.21. Found: C, 40.99; H, 6.64; P, 13.40.

EXAMPLE 10

(E)-(4,8-Dimethyl-3,7-nonadienylidene)bisphosphonic acid, trisodium salt

A.

(E)-(4,8-Dimethyl-3,7-nonadienylidene)bisphosphonic acid, tetraethyl ester

To a stirred solution of 417 mg (17.37 mmol) of NaH in 10 mL of THF at 0° C. under argon was added dropwise 4.32 mL (17.37 mmol) of tetraethyl methylenediphosphonate in 2 mL of THF. The mixture was stirred for 0.5 hours at 0° C., at which time 1.00 g (5.79 mmol) of (E)-3,7-dimethyl-2,6-octadien-1-yl chloride (Example 5, Part A) in 2 mL THF was added dropwise. The reaction was stirred at 0° C. for 1 hour, at room temperature for 18 hours, then diluted with ether and quenched with saturated NH$_4$Cl. The organic layer was washed with water, brine, dried (MgSO$_4$) and evaporated to provide 1.92 g of a pale yellow oil. Flash chromatography was performed on 150 g of silica gel, eluted with ethyl acetate (800 mL), followed by a 49.5:49.5:1 mixture of acetone/ethyl acetate/methanol. Pure product fractions were combined and evaporated to provide 1.12 g (46%) of title ester as a pale yellow oil.

TLC Silica gel (49.5:49.5:1 acetone/ethyl acetate/methanol) R$_f$=0.35.

IR (CCl$_4$) 2980, 2930, 1442, 1249, 1026, 970 cm$^{-1}$.

$^1$H NMR (270 MHz, CDCl$_3$): δ5.31 (t, 1H, J=7.0 Hz), 5.08 (m, 1H), 4.17 (quint., 8H, J=7.1 Hz), 2.65 (tt, 2H, J=6.7, 17.3 Hz), 2.30 (tt, 1H, J=6.1, 23.5 Hz), 2.03 (m, 4H), 1.67 (s, 3H), 1.64 (s, 3H), 1.59 (s, 3H), 1.34, 1.33 (two t, 12 H, J=7.1 Hz) ppm.

MS (CI-NH$_3$, +ions) m/e 425 (M+H).

B.

(E)-(4,8-Dimethyl-3,7-nonadienylidene)bisphosphonic acid, trisodium salt

To a stirred solution of 790 mg (1.86 mmol) of Part A ester in 20 mL of CH$_2$Cl$_2$ at 0° C. under argon was added 988 μL (3.72 mmol) of bis(trimethylsilyl)trifluoroacetamide followed by 1.23 mL (9.30 mmol) of bromotrimethylsilane. The reaction was stirred at 0° C. for 0.5 hours and room temperature for 18 hours, when the solvent was evaporated and the residue was pumped at high vacuum for 2 hours. The remainder was dissolved in 6.70 mL (13.40 mmol) of 2 M NH$_4$OH and purified by MPLC on a column of CF11 cellulose (5 cm diameter ×15 cm height) eluted with 2:3:1 isopropanol/acetonitrile/0.1M ammonium hydroxide (1.5 liter) followed by 500 mL of 2:1:1 isopropanol/acetonitrile/0.1M ammonium hydroxide. Approximately 30 mL fractions were collected. Product fractions were combined and the organic solvents were removed to provide an aqueous solution.

The concentrated sample was treated with 2 mL (11.16 mmol) of triethylamine, and evaporated. This procedure was performed two more times. The oily residue was dissolved in 20 mL of water and passed through a column of AG 50W-X8 resin (sodium form, 40 mL) eluting with water. The eluent was lyophilized and the residue was further purified by MPLC on a column of CHP20P gel (5.0 cm diameter ×25 cm height) eluting with water. Approximately 15 mL fractions were collected. Pure product fractions were combined and lyophilized to provide 400 mg (57%) of title product as a white lyophilate.

IR (KBr) 2968, 2922, 1637, 1151, 1118, 881, 540 cm$^{-1}$.

$^1$H NMR (400 MHz, D20): δ5.40 (t, 1H, J=7.0 Hz), 5.18 (t, 1H, J=7.2 Hz), 2.45 (tt, 2H, J=7.0, 15.6 Hz), 2.08, 1.98 (two m, 4H), 1.80 (tt, 1H, J=7.0, 21.4 Hz), 1.63 (s, 3H), 1.60 (s, 3H), 1.57 (s, 3H) ppm.

MS (FAB, +ions) m/e 423 (M-H+2Na), 401 (M+Na), 379 (M+H), 357 (M-Na-2H).

Anal. Calc'd for $C_{11}H_{19}P_2O_6Na_3 \cdot 0.25$ mol $H_2O$: Effective MW =382.6 C, 34.52; H, 5.14; P, 16.18. Found: C, 34.45; H, 5.40; P, 16.09.

EXAMPLE 11

(E)-[4-[4-(2,6-Dimethyl-1,5-heptadienyl)phenyl]-butylidene]bisphosphonic acid, tripotassium salt

A.

(E)-4-(2,6-Dimethyl-1,5-heptadienyl)benzenemethanol (1) 6-Methyl-5-hepten-1-yne

A modification of the published procedure was employed P. A. Jacobi, *Tetrahedron* 1987, 43, 5475–5488.

To a suspension of 12.48 g (128.8 mmol) of 95% lithium acetylide-ethylenediamine complex in 64 mL of freshly distilled dimethyl sulfoxide under argon between 5°-10° C. was added 20 g (122.6 mmol) of 5-bromo-2-methyl-2-pentene dropwise over 30 minutes with vigorous stirring. After the addition was complete, the mixture was allowed to warm to room temperature gradually over 1 hour and then stirred at room temperature for 1 hour. The reaction was cooled to about 15° C. and quenched by the slow addition of 25 mL of water. The reaction mixture was then distilled under reduced pressure using a short path distillation head and cooling the condenser with a 50:50 mixture of water:ethylene glycol from a circulating cold bath at −20° C. The product was collected at a boiling point range of 28°-37° C., pressure 90 mm Hg with an oil bath temperature of 60°-62° C. The distillation was run under these parameters for 1 hour and then the pressure was carefully lowered to 60 mm Hg and the distillation was continued for 1.5 hours to provide 9.28 g of a clear, colorless liquid. This material was fractionally distilled at 1 atmosphere to provide 4.01 g (30%) of 2-methyl-2,3-pentadiene (bp 85°-90° C.), followed by 4.43 g (33%) of the desired title (1) eneyne (bp 120-125° C) as a colorless liquid.

$^1$H-NMR (CDCl, 270 MHz): δ5.17 (m, 1H), 2.19 (m, 4H), 1.93 (t, 1H, J=2.3 Hz), 1.70 (s, 3H), 1.62 (s, 3H) ppm.

(2) (E)-1-Iodo-2,6-dimethyl-1,5-heptadiene

The following procedure of Negishi was used for the reaction: E. Negishi, *J. Am. Chem. Soc.* 1985, 107, 6639–6647.

To a stirred solution of 4.13 g (13.86 mmol) of 98% zirconocene dichloride in 35 mL of dichloromethane under argon at room temperature was added 13.9 mL (27.72 mmol) of 2.0M trimethyl aluminum in hexanes. The mixture was allowed to stir at room temperature for 0.5 hours resulting in a lemon-yellow solution to which 1.5 g (13.86 mmol) of Part (1) compound was added neat and the reaction was allowed to stir at room temperature for 24 hours. The yellow solution was cooled to −30° C. and 4.22 g (16.6 mmol) of iodine in 15 mL of THF was added dropwise over 10 minutes. Upon addition of the iodine, the solution color turned orange-brown for a few minutes and then turned orange-yellow with precipitated solids. The mixture was allowed to warm to 0° C. and stir for 0.5 hours when it was quenched with methanol and diluted with ether. The organic layer was washed with aqueous $Na_2S_2O_3$, dried over $MgSO_4$ and filtered. The solvent was removed by distillation using a fractionating column (bp 38°-40° C./1 atmosphere) to provide a dark yellow oil as the pot residue. The remaining port residue was further purified by bulb-to-bulb distillation (115° C./2 mm) to provide 2.32 g (67%) of title iodide as a pale yellow oil.

$^1$H-NMR (CDCl, 270 MHz): δ5.87 (s, 1H), 5.05 (m, 1H), 2.15 (m, 4H), 1.84 (s, 3H), 1.68 (s, 3H), 1.60 (s, 3H) ppm.

(3) (E)-4-(2,6-Dimethyl-1,5-heptadienyl)benzoic acid, methyl ester

To 10 mL of THF under argon at −78° C. was added 6.1 mL (10.3 mmol), of 1.7M t-butyllithium in pentane resulting in a yellow solution, to which 1.075 g (4.29 mmol), of Part (2) iodide in 10 mL of THF was added dropwise over 5 minutes. After the addition, the reaction was allowed to stir at −78° C. for 0.5 hours and then warm to 0° C. for 0.5 hours. zinc chloride (702 mg, 5.16 mmol, fuse-dried under vacuum three times) in 7 mL of THF was added via cannula to give a very pale yellow solution, which was allowed to stir at 0° C. for 1 hour.

A 100 mL flask was charged with 248 mg (5 mol %) of tetrakis(triphenylphosphine) palladium and 804 mg (3.07 mmol) of methyl 4-iodobenzoate in an argon filled glove bag. A volume of 10 mL of THF was added and the suspension was cooled to 0° C. when the zinc intermediate prepared above was added via cannula. The mixture was allowed to warm to room temperature and stir for 1.5 hours when it was diluted with ether and quenched by the addition of 1 N HCl solution. The organic layer was washed with water, saturated $NaHCO_3$, brine, dried over $MgSO_4$ and evaporated to provide 1.29 g of an orange-yellow oily solid. Flash chromatography was performed on 130 g of silica gel packed and loaded with 5:1 hexane/toluene and eluted with 3:1 hexane/toluene collecting 30 mL fractions. Fractions 84 to 106 were combined and evaporated to provide 602 mg (76%) of title esters as a clear, colorless oil.

TLC Silica gel (9:1 hexane/EtOAc) $R_f$=0.47.

IR (CC14) 2968, 2914, 1724, 1606, 1435, 1309, 1277, 1192, 1178 cm$^{-1}$.

$^1$H-NMR (CDC13, 270 MHz): δ7.97 (d, 2H, J=8.2 Hz), 7.28 (d, 2H, J=8.2 Hz), 6.28 (s, 1H), 5.15 (m, 1H), 3.89 (s, 3H), 2.20 (m, 4H), 1.87 (d, 3H, J=1.2 Hz), 1.70 (s, 3H), 1.63 (s, 3H) ppm.

MS (CI-NH$_3$, +ions) m/e 276 (M+NH$_4$), 259 (M+H).

(4) (E)-4-(2,6-Dimethyl-1,5-heptadienyl)benzenemethanol

To 133 mg (3.49 mmol) of lithium aluminum hydride under argon at 0° C. suspended in 10 mL of dry ether was added 602 mg (2.32 mmol) of Part (3) ester in 15 mL of dry ether dropwise over 5 minutes. The reaction was allowed to stir at 0° C. for 0.5 hours when it was quenched by the addition of 0.14 mL of water, 0.14 mL of 15% NaOH solution and then with 0.42 mL of water. After stirring for 0.5 hours, $Na_2SO_4$ was added and the slurry was allowed to stir for 1 hour before filtering through a pad of Celite washing copiously with ether. Evaporation provided 519 mg (97%) of a pale yellow oil. The crude material was combined with 324 mg of crude product from a previous reduction on 371 mg (1.44 mmol) of Part (3) ester to provide 843 mg of crude product. Flash chromatography was performed on 85 g of silica gel packed and loaded with 15:1 hexane/EtOAc and eluted with 9:1 hexane/EtOAc collecting 30 mL fractions. Fractions 34 to 85 were combined and evaporated to provide 802 mg (93%) of title alcohol as a clear, colorless oil.

TLC Silica gel (12:1 dichloromethane/EtOAc) $R_f=0.36$.

IR (CCl$_4$) 3617, 3400, 2967, 2928, 2874, 2858, 1718, 1449, 1414, 1377, 1032, 1013, 795 cm$^{-1}$.

$^1$H-NMR (CDCl$_3$, 270 MHz): δ7.27 (d, 2H, J=8.2 Hz), 7.20 (d, 2H, J=8.2 Hz), 6.25 (s, 1H), 5.16 (m, 1H), 4.60 (s, 2H), 2.18 (m, 4H), 1.85 (d, 3H, J=1.2 Hz), 1.70 (s, 3H), 1.63 (s, 3H) ppm.

MS (CI-NH$_3$, +ions) m/e 478 (2M+NH$_4$), 460 (2M), 248 (M+NH$_4$), 230 (M), 213 (M+H-H$_2$O).

Analysis Calc'd for C$_{16}$H$_{22}$O (M.W.=230.36): C, 83.43; H, 9.63 Found: C, 83.18; H, 9.73.

B.

(E)-1-(Bromomethyl)-4-(2,6-dimethyl-1,5-heptadienyl)-benzene

To a stirred solution of 1 g (4.34 mmol) of Part A alcohol in 50 mL of dichloromethane under argon at −30° C. was added 1.36 g (5.21 mmol) of triphenylphosphine followed by 850 mg (4.77 mmol) of N-bromosuccinimide and the reaction was allowed to stir at −30° C. for 1 hour when it was concentrated to about 5 mL. Flash chromatography was performed on 125 g of silica gel packed, loaded and eluted with 1% EtOAc/pentane collecting 10 mL fractions. Fractions 14 to 40 were combined and evaporated to provide 863 mg (69%) of title compound in the form of a clear colorless oil.

TLC Silica gel (9:1 Pentane/EtOAc) $R_f=0.59$.

IR (CCl$_4$) 2969, 2930, 2857, 1711, 1608, 1510, 1450, 1377, 1229, 1202, 775 cm$^{-1}$.

$^1$NMR (CDCl$_3$, 270 MHz) δ7.32 (d, 2H, J=8.2 Hz), 7.19 (d, 2H, J=8.2 Hz), 6.23 (s, 1H), 5.15 (m, 1H), 4.49 (s, 2H), 2.19 (m, 4H), 1.85 (s, 3H), 1.70 (s, 3H), 1.63 (s, 3H), ppm.

C.

(E)-4-(2,6-Dimethyl-1,5-heptadienyl)benzenepropanoic acid, 1,1-dimethylethyl ester To a stirred solution of 0.62 mL (4.44 mmol) of freshly distilled diisopropylamine in 4 mL of THF under argon at −78° C. was added 1.85 mL (2.96 mmol) of 1.6 M n-butyllithium in hexanes to give a pale yellow solution. The solution was allowed to warm to 0° C. for 15 minutes and then cooled again to −78° C. when 0.40 mL (2.96 mmol) of t-butyl acetate was added neat. After an additional 15 minutes, 1.05 mL (6.07 mmol) of HMPA followed by 853 mg (2.96 mmol) of Part B bromide in 5 mL of dry THF was added dropwise over 5 minutes. The reaction was allowed to stir at −78° C. for 1 hour when it was diluted with ether and quenched by the addition of saturated NH$_4$Cl solution. The organic layer was washed with water, brine, dried over MgSO$_4$ and evaporated to provide 994 mg of a clear colorless oil. Flash chromatography was performed on 100 g of silica gel packed and loaded with 2% EtOAc/hexane and eluted with 3% EtOAc/hexane collecting 30 mL fractions. Fractions 18 to 25 were combined and evaporated to provide 850 mg (87%) of title compound in the form of a clear colorless oil.

TLC Silica gel (9:1 hexane/EtOAc) $R_f=0.53$.

IR (CCL$_4$) 2969, 2928, 2874, 1730, 1512, 1452, 1368, 1269, 1146, 849 cm$^{-1}$.

$^1$H NMR (270 MHz, CDCl$_3$): δ7.14 (s, 4H), 6.23 (s, 1H), 5.15 (m, 1H), 2.88 (t, 2H, J=7 Hz), 2.52 (t, 2H, J=7 Hz), 2.17 (m, 4H), 1.85 (s, 3H), 1.70 (s, 3H), 1.63 (s, 3H), 1.41 (s, 9H) ppm.

MS (CI-NH$_3$, +ions) m/e 346 (M+NH$_4$).

Anal. Calc'd for C$_{22}$H$_{32}$O$_2$: C, 80.44; H, 9.82 Found: C, 80.51; H, 9.76.

D.

(E)-4-(2,6-Dimethyl-1,5-heptadienyl)benzenepropanol

To 215 mg (5.66 mmol) of lithium aluminum hydride under argon at 0° C. was added 10 mL of dry ether followed by 1.24 g (3.77 mmol) of Part C compound in 20 mL of dry ether dropwise over 10 minutes. The reaction was allowed to stir at 0° for 0.5 hours when it was quenched by the addition of 0.23 mL of H$_2$O, 0.23 mL of 15% NaOH solution and then with 0.68 mL of H$_2$O. After stirring for 0.5 hours, Na$_2$SO$_4$ was added and the mixture was allowed to stir for 1 hour before filtering through a pad of Celite washing copiously with ether. Evaporation provided 973 mg of a pale yellow oil. Flash chromatography was performed on 100 g of silica gel packed and loaded with 7:1 hexane/EtOAc and eluted with 6:1 hexane/EtOAc collecting 30 mL fractions. Fractions 25 to 42 were combined and evaporated to provide 876 mg (90%) of title compound in the form of a clear colorless oil.

TLC Silica gel (4:1 hexane/EtOAc) $R_f=0.19$.

IR (CCl$_4$) 3346, 2928, 2857, 1670, 1510, 1447, 1377, 1059 cm$^{-1}$.

$^1$H NMR (270 MHz, CDCl$_3$): δ7.15 (m, 4H), 6.23 (s, 1H), 5.16 (m, 1H), 3.66 (br t, 2H, J=6.5 Hz), 2.68 (t, 2H, J=7.6 Hz), 2.18 (m, 4H), 1.89 (m, 2H), 1.85 (s, 3H), 1.70 (s, 3H), 1.63 (s, 3H), 1.54 (br s, 1H) ppm.

MS (CI-NH$_3$, +ions) m/e 276 (M+NH$_4$).

Anal. Calc'd for C$_{18}$H$_{26}$O: C, 83.67; H, 10.14 Found: C, 83.79; H, 10.01.

E.

(E)-1-(2,6-Dimethyl-1,5-heptadienyl)4-(3-iodopropyl)-benzene

To a stirred solution of 300 mg (1.16 mmol) of Part D compound, 336 mg (1.28 mmol) of triphenylphosphine and 166 mg (2.44 mmol) of imidazole in 6 mL of THF under argon at room temperature was added 294 mg (1.16 mmol) of iodine in 6 mL of THF dropwise over 5 minutes. Upon addition the clear solution would turn yellow and then quickly back to clear. Near the end of the addition the color remained pale yellow. After addition, the reaction was complete by TLC. The reaction was diluted with ether and washed with water, saturated Na$_2$S$_2$O$_3$, brine, dried over MgSO$_4$ and evaporated to provide an oily white solid. Flash chromatography was performed on 50 g of silica gel packed, loaded and eluted with hexane collecting 15 mL fractions. Fractions 7 to 24 were combined and evaporated to provide 342 mg (80%) of title compound in the form of a clear colorless oil.

TLC Silica gel (4:1 hexane/EtOAc) $R_f=0.65$.

$^1$H NMR (270 MHz, CDCl$_3$): δ7.15 (m, 2H), 6.23 (s, 1H), 5.16 (m, 1H), 3.17 (t, 2H, J=7 Hz), 2.70 (t, 2H, J=7 Hz), 2.19 (m, 4H), 2.14 (quint., 2H, J=7 Hz), 1.86 (s, 3H), 1.70 (s, 3H), 1.63 (s, 3H) ppm.

F.
(E)-[4-[4-(2,6-Dimethyl-1,5-heptadienyl)phenyl]-butylidene]bisphosphonic acid, tetraethyl ester To a suspension of 111 mg (2.79 mmol) of 60% NaH in mineral oil in 3 mL of DMF under argon at 0° C. was added 0.71 mL (2.88 mmol) of tetraethyl methylenediphosphonate over 10 minutes with much gas evolution. The reaction was allowed to warm to room temperature and stir for 0.5 hours when 342 mg (0.929 mmol) of Part E compound in 5 mL of DMF was added. The reaction was allowed to stir at room temperature overnight. The reaction was diluted with ether and quenched by the addition of saturated $NH_4Cl$ solution. The organic layer was washed with water, brine, dried over $MgSO_4$ and evaporated to provide 569 mg of a very pale yellow oil. Flash chromatography was performed on 85 g of silica gel packed, loaded and eluted with 2:98 $CH_3OH/CH_2Cl_2$ collecting 20 mL fractions. Fractions 32 to 54 were combined and evaporated to provide 329 mg (67%) of a clear colorless oil.

TLC Silica gel (5:95 $CH_3OH/CH_2Cl_2$) $R_f=0.29$.

IR (CC14) 3481, 2980, 2930, 1477, 1250, 1163, 1024, 970 $cm^{-1}$.

$^1H$ NMR (270 MHz, $CDCl_3$): δ7.13 (m, 4H), 6.22 (s, 1H), 5.15 (m, 1H), 4.15 (m, 8H), 2.61 (t, 2H, J=6.45 Hz), 2.30 (tt, 1H, J=23 and 5 Hz)*, 2.17 (m, 4H), 1.93 (m, 4H), 1.85 (s, 3H), 1.69 (s, 3H), 1.63 (s, 3H), 1.31 (m, 12H total) ppm.
*This resonance is partially obscured.

MS (CI, +ions) m/e 529 (M+H).

[Anal. Calc'd for $C_{27}H_{46}O_6P_2$: C, 61.35; H, 8.77; P, 11.72. Found: C, 61.22; H, 9.00; P, 12.00.

G.
(E)-[4-[4-(2,6-Dimethyl-1,5-heptadienyl)phenyl]-butylidene]bisphosphonic acid, tripotassium salt To a solution of 485 mg (0.917 mmol) of Part F ester in 7 mL of dry dichloromethane under argon at 0° C. was added 0.36 mL (2.75 mmol) of 2,4,6-collidine followed by 0.72 mL (5.50 mmol) of bromotrimethylsilane and the reaction was allowed to warm to room temperature and stir for 24 hours. The solvent was evaporated and pumped at high vacuum for 1 hour. The remainder was dissolved in 5.5 mL of 1 M KOH solution, stirred for 1 hour, diluted with water and lyophilized to provide 870 mg of crude material which was purified by MPLC on a column of CHP20P gel (2.5 cm diameter ×21 cm height) eluted with water (fractions 1 to 15) followed by a gradient created by the gradual addition of 500 mL of 70:30 $CH_3CN/H_2O$ to a reservoir of 450 mL of water. Approximately 10 mL fractions were collected. Fractions 47 to 59 were combined, the acetonitrile was evaporated at reduced pressure and the aqueous solution was adjusted to pH 12 and repurified by MPLC on a column of CHP20P (2.5 cm diameter ×20 cm height) eluted with water fractions (1 to 12) followed by a gradient created by the gradual addition of 500 mL of a 60:40 $CH_3CN/H_2O$ to a reservoir of 45 mL of water. Fractions 28 to 33 were combined, the acetonitrile was evaporated at reduced pressure and the aqueous solution was lyophilized to provide 225 mg of a dense white lyophilate #1. Fractions 43 to 46 from the first CHP20P chromatography were combined, the acetonitrile was evaporated at reduced pressure and the aqueous solution was lyophilized to provide 162 mg of a dense white lyophilate #2. Fractions 34 to 37 from the second CHP20P chromatography were combined. The acetonitrile was evaporated at reduced pressure and the aqueous solution was lyophilized to provide 61 mg of a dense white lyophilate #3.

Lyophilate #2 and lyophilate #3 were combined and the pH was adjusted to 12. The material was repurified by MPLC on a column of SP207 (2.5 cm diameter ×14 cm height) eluted with water fractions (1 to 9) followed by a gradient created by the gradual addition of 500 mL of $CH_3CN$ to a reservoir of 450 mL of water. Approximately 12 mL fractions were collected. Fraction 23 was evaporated at reduced pressure to remove the acetonitrile and the aqueous solution was lyophilized to provide 21 mg of a dense white lyophilate #4. Lyophilate #1 and lyophilate #4 were combined with about 15 mL of water and lyophilized to provide 243 mg (50%) of title compound in the form of a dense white lyophilate. Further drying under high vacuum led to an insignificant loss of mass. $^1H$ NMR and microanalysis indicate that this material contains 1 equiv. of acetic acid.

IR (KBr) 3385, 2966, 2928, 2359, 1576, 1406, 1144, 1113, 885 $cm^{-1}$.

$^1H$ NMR (400 MHz, $D_2O$): δ7.26 (d, 2H, J=8 Hz), 7.21 (d, 2H, J=8 Hz), 6.25 (s, 1H), 5.20 (m, 1H), 2.60 (t, 2H, J=7 Hz), 2.18 (m, 4H), 1.88 (tt, 1H, J=22 and 5 Hz)*, 1.81 (s, 3H), 1.80 (s, 4H), 1.65 (s, 3H), 1.59 (s, 3H) ppm.
*This resonance is partially obscured.

MS (FAB, +ions) m/e 531 (M+H), 493 (M+2H-K), 455 (M+3H-2K).

Anal. Calc'd for $C_{19}H_{27}O_6P_2K_3 \cdot 1.4$ $H_2O \cdot 1.0$ $CH_3CO_2H$: C, 40.95; H, 5.53; P, 10.06 Found: C,41.01; H, 5.18; P, 9.75.

EXAMPLE 12
(E)-(7,11-Dimethyl-6,10-dodecadienylidene)bisphosphonic acid, tripotassium salt

A. (E)-6,10-Dimethyl-5,9-undecadien-1-ol

A solution of 198 mL (58.0 mmol) of 0.29M Grignard reagent (Example 4, Part A(2)) in THF and 48 mL (275.9 mmol) of HMPA at 0° C. under argon was treated dropwise with 2.0 g (11.6 mmol) of geranyl chloride (Example 5, Part A) in 20 mL of THF. After addition, the reaction was allowed to warm to room temperature for 2 hours, at which point the reaction was diluted with 1:1 hexane/ether and quenched with 1 N HCl solution. The organic layer was washed with 1 N HCl followed by water, saturated sodium bicarbonate, brine, dried over $MgSO_4$ and evaporated to provide 3.59 g of crude oil. Flash chromatography was performed on 360 g of silica gel packed and loaded with 10:1 hexane/EtOAc and eluted with 7:1 hexane/EtOAc collecting 30 mL fractions. Fractions 32 to 49 were combined and evaporated to provide 1.68 g (74%) of an oil.

TLC Silica gel (7:1 hexane/EtOAc) $R_f=0.19$.

$^1H$ NMR ($CDCl_3$, 270 MHz): δ511.(m, 2H), 3.61 (t, H, J=6.45 Hz), 2.03 (m, 6H), 1.68 (s, 3H), 1.59 (s, 6H), 1.5-1.6 (m, 2H), 1.41 (m, 2H) ppm.

B. (E)-6,10-Dimethyl-5,9-undecadien-1-yl iodide

A solution of 1.80 g (9.20 mmol) of Part A (E)-6,10-dimethyl-5,9-undecadien-1-ol in 50 mL of methylene chloride and 2.00 mL (14.3 mmol) of triethylamine at 0° C. was treated with 1.14 g (10.00 mmol) of methanesulfonyl chloride dropwise over 0.2 hours. The reaction mixture was stirred for 1.0 hour when it was quenched with saturated aqueous $NH_4Cl$ solution and diluted with ether. The organic fraction was washed with saturated NaHCO$_3$, brine, dried (Na$_2$SO$_4$) and evaporated to provide a crude colorless oil. The crude mesylate (~9.0 mmol) was diluted with 50 mL of acetone and treated with 4.05 g (27.00 mmol) of NaI, refluxed for 5 hours, and cooled to room temperature. The mixture was diluted with 250 mL of ether and extracted with NaHSO$_3$, brine, dried (MgSO$_4$) and concentrated to provide a pale yellow oil. The oil was purified by flash chromatography (180 g of silica gel) eluting with hexane to provide 2.60 g (85%) of title iodide as a colorless oil.

TLC Silica gel (hexane) R$_f$=0.55.

IR (neat) 2963, 2926, 2854, 1448, 1377, 1221, 1107 cm$^{-1}$.

$^1$H NMR (CDCl$_3$, 270 MHz): δ5.10 (m, 2H), 3.20 (t, 2H, J=6.5 Hz), 2.05 (m, 6H), 1.80 (quint., 2H, J=6.0 Hz), 1.60 (s, 3H), 1.55 (s, 6H), 1.45 (m, 2H) ppm.

Mass Spec (CI-NH$_3$, +ions) m/e 306 (M), 324 (M+NH$_4$)

C.
(E)-(7,11-Dimethyl-6,10-dodecadienylidene)bisphosphonic acid, tetraethyl ester To a suspension of 144 mg (6.00 mmol) of NaH in 5 mL of dry DMF at 0° C. under argon was added 1.72 g (6.00 mmol) of tetraethyl methylenediphosphonate over 15 minutes to give a yellow solution. The reaction was allowed to warm to room temperature and stir for 0.5 hours when 0.63 g (2.00 mmol) of Part B iodide was added in one portion. The reaction mixture was stirred for 18 hours when it was quenched with saturated aqueous NH$_4$Cl solution and diluted with ethyl acetate. The organic fraction was washed with water, brine, dried (Na$_2$SO$_4$) and evaporated to provide a crude yellow oil. Flash chromatography was performed on 100 g of silica gel eluted with 4:96 methanol/methylene chloride collecting in 50 mL fractions to provide 0.45 g (47%) of title compound in the form of a pale yellow oil.

TLC Silica gel (1:9 methanol/methylene chloride) R$_f$=0.75.

IR (CHCl3 solution) 2980, 2930, 1645, 1445, 1250, 1165, 1097, 1028, 972 cm$^{-1}$. $^1$H NMR (CDCl$_3$, 270 MHz): δ5.10 (q, 2H, J=5.9 Hz), 4.20 (m, 8H), 2.27 (tt, 1H, J=24.0, 5.9 Hz), 2.10-1.80 (m, 8H), 1.67 (s, 3H), 1.60 (s, 3H), 1.59 (s, 3H), 1.57 (m, 2H), 1.33 (t, 12H, J=7.1 Hz), 1.32 (m, 2H) ppm.

Mass Spec (CI-NH$_3$, +ions) m/e 467 (M+H), 484 (M+NH$_4$)

D.
(E)-(7,11-Dimethyl-6,10-dodecadienylidene)bisphosphonic acid, tripotassium salt To a stirred solution of 0.43 g (0.90 mmol) of Part C ester in 7 mL of dichloromethane at room temperature was added 0.22 g (1.38 mmol) of 2,4,6-collidine followed by 0.70 g (4.57 mmol) of bromotrimethylsilane. The reaction was allowed to stir at room temperature for 14 hours when the solvent was evaporated and the semisolid residue pumped (~1 mm pressure) for 0.5 hours. The residue was dissolved by adding 4.0 mL of 1 N KOH solution (4.0 mmol) then diluting with 15 mL of water. The solution was freeze dried to provide off white solids. The solids were purified by MPLC on a column of SP207SS gel (2.5 cm diam. ×15 cm height) eluting with water (150 mL) followed by a gradient created by the gradual addition of 400 mL of acetonitrile to a reservoir of 350 mL of water. Approximately 10 mL fractions were collected. The acetonitrile was removed under reduced pressure and the aqueous solution was lyophilized to provide 0.39 g (92%) of title compound as a white lyophilate.

IR (KBr) 3426, 2964, 2923, 2856, 1630, 1506, 1298, 866cm$^{-1}$.

$^1$H NMR (D20, 400 MHz): δ5.23 (t, 1H, J=7.0 Hz), 5.15 (t, 1H, J=7.0 Hz), 2.05 (m, 2H), 1.98 (m, 4H), 1.74 (m, 3H), 1.63 (s, 3H), 1.57 (s, 6H), 1.37 (m, 2H), 1.28 (quint., 2H, J=7.0 Hz) ppm.

Mass Spec (FAB, +ions), m/e 469 (M+H), 431 (M-K+2H), 413 (M-K+2H-H$_2$O), 493 (M-2K+3H).

Anal. Calc'd for C$_{14}$H$_{25}$O$_6$K$_3$P$_2$+1.42 H$_2$O: C, 34.03; H, 5.68; P, 12.54 Found: C, 34.03; H, 5.84; P, 12.69.

EXAMPLE 13
(10-Methyl-9-undecenylidene)bisphosphonic acid, tripotassium salt

A. 9-Methyl-8-decen-1-ol

A solution of 55.0 mL (~52 mmol) of 0.95M Grignard reagent prepared in Example 3, Part A in THF and 15.0 mL of hexamethylphosphoric triamide (HMPA) at 0° C. was treated dropwise with 1.95 g (13.1 mmol) of phenyl bromide in 8 mL of THF over 10 minutes. After the addition the reaction was allowed to warm to room temperature and stir for 3.5 hours, at which point the reaction was diluted with ether and quenched with 100 mL (100 mmol) of 1M HCl solution. The organic layer was washed two times with NH$_4$Cl solution, dried over MgSO$_4$ and evaporated to provide a pale yellow oil. The oil was purified by flash chromatography performed on 200 g of silica gel eluted with 1:4 ethyl acetate/hexanes to provide 3.50 g of oil and hexanol. The hexanol was removed by distillation under reduced pressure (BP 75° C., ~20 mm Hg) to leave 1.50 g (67%) of title compound in the form of a colorless oil. This material contains ~2% of the Sn2' product, which could not be separated.

TLC Silica gel (1:9 ethyl acetate/hexane) R$_f$=0.20.

IR (neat) 3326, 2927, 2855, 1452, 1377, 1059, 625 cm$^{-1}$.

$^1$H NMR (CDCl3, 270 MHz): δ5.13 (t, 1H, J=7.1 Hz), 3.60 (t, 2H, J=6.4 Hz), 2.40 (m, 1H), 1.90 (m, 2H), 1.67 (s, 3H), 1.59 (s, 3H), 1.50 (m, 2H), 1.39 (m, 8H) ppm.

MS (CI-NH$_3$, +ions) m/e 188 (M+NH$_4$).

B. 10-Iodo-2-methyl-2-decene

To a stirred solution of 1.20 g (7.05 mmol) of Part A compound and 2.00 mL (13.70 mmol) of triethylamine in 10 mL of methylene chloride at 0° C. was added 0.67 mL (8.47 mmol) of methanesulfonyl chloride dropwise over 15 minutes. After 1 hour at 0° C. the reaction was diluted with ether and washed with aqueous solutions of NH$_4$Cl, NaHCO$_3$, and brine. The organic layer was dried (MgSO$_4$) and concentrated under reduced pressure to provide the crude mesylate. The residual oil was dissolved in 150 mL of acetone and treated with 4.00 g (28.0 mmol) of NaI and stirred overnight at room temperature. The reaction mixture was diluted with ether and washed with aqueous solutions of Na$_2$SO$_3$ and brine. The organic fraction was dried over MgSO$_4$ and concentrated to provide a yellow oil. The oil was purified by flash chromatography on 100 g of silica gel eluted with hexanes to provide 1.80 g (6.43 mmol, 68% overall yield) of title compound as a colorless oil.

TLC Silica gel (hexanes) $R_f=0.50$.

IR (CC14 solution) 2926, 2854, 1738, 1641, 1448, 1228 cm$^{-1}$.

$^1$H NMR (270 MHz, CDCl$_3$): δ5.10 (t, 1H, J=7.0 Hz), 3.15 (t, 2H, J=7.0 Hz), 1.95 (m, 2H), 1.83 (quint., 2H, J=5.7 Hz), 1.66 (s, 3H), 1.57 (s, 3H), 1.35 (m, 2H), 1.30 (m, 6H) ppm.

MS (CI-NH$_3$, +ions) m/e 298 (M+NH$_4$).

C. (10-Methyl-9-undecenylidene)bisphosphonic acid, tetraethyl ester

A suspension of 180 mg (7.50 mmol) of NaH in 7 mL of dry DMF at 0° C. under argon was treated with 2.16 g (7.50 mmol) of tetraethyl methylenediphosphonate over 20 minutes to give a yellow solution. The reaction was allowed to warm to room temperature and stir for 0.5 hours when 0.70 g (2.50 mmol) of Part B iodide was added in one portion. The reaction mixture was stirred for 18 hours when it was quenched with saturated aqueous NH$_4$Cl solution and diluted with ethyl acetate. The organic fraction was washed with brine, dried over Na$_2$SO$_4$ and evaporated to provide a crude yellow oil. Flash chromatography was performed on 100 g of silica gel packed, loaded and eluted with ethyl acetate (0.3 L), followed by 1:9 ethanol/ethyl acetate (1 L) to provide 0.73 g (66%) of title ester as a pale yellow oil.

TLC Silica gel (1:9 ethanol/ethyl acetate) $R_f=0.45$.

IR (KBr) 3053, 2985, 2929, 2856, 1444, 1266, 1028, 972, 739 cm$^{-1}$.

$^1$H NMR (CDCl$_3$ 270 MHz): δ5.11 (t, 1H, J=7.0 Hz), 4.19 (m, 8H), 2.27 (tt, 1H, J=24.0, 5.9 Hz), 2.05–1.80 (m, 4H), 1.67 (s, 3H), 1.59 (s, 3H), 1.55 (m, 2H), 1.34 (t, 9H, J=7.0 Hz), 1.29 (m, 8H) ppm.

MS (CI-NH$_4$, +ions) m/e 458 (M+NH$_4$), 441 (M+H).

D. (10-Methyl-9-undecenylidene)bisphosphonic acid, tripotassium salt

To a stirred solution of 0.70 g (1.59 mmol) of Part C ester in 7.0 mL of dichloromethane at 0° C. was added 0.39 mL (3.00 mmol) of 2,4,6-collidine followed by 1.05 mL (7.95 mmol) of bromotrimethylsilane. The reaction was allowed to stir at room temperature for 13 hours when the solvent was evaporated and the semisolid residue pumped (~1 mm pressure) for 0.5 hours. The residue was dissolved in 6.40 mL of 1 N KOH solution (6.40 mmol), diluted with 15 mL of water and freeze dried. The crude white solids were purified by MPLC on a column of SP207SS gel (2.5 cm diam. ×25 cm height) eluting with water (250 mL), followed by a gradient created by the gradual addition of 400 mL acetonitrile to a reservoir of 350 mL of water. Approximately 15 mL fractions were collected. The aqueous solution was filtered and lyophilized to provide 0.58 g (82%) of title product as a white lyophilate.

TLC Silica gel (5:4:1 n-propanol/conc. ammonia/water) $R_f=0.05$. $^1$NMR (D$_2$O, 400 MHz): δ5.18 (t, 1H, J=7.0 Hz), 1.96 (m, 2H), 1.70 (m, 3H), 1.63 (s, 3H), 1.56 (s, 3H), 1.45 (m, 2H), 1.25 (s, 8H) ppm.

Mass Spec. (FAB, +ions) m/e 519 (M+2K-H), 481 (M+K), 443 (M+H), 425 (M-H$_2$O+H).

Anal. Calc'd for C$_{12}$H$_{23}$O$_6$K$_3$P$_1$+1.89 H$_2$O: C, 30.24; H, 5.66; P, 13.00. Found: C, 30.24; H. 5.75; P, 13.04.

EXAMPLE 14

[4-[4-(2-Methyl-1-propenyl)phenyl]butylidene]bisphosphonic acid, trisodium salt

A. 1-Bromo-4-(2-methyl-1-propenyl)benzene

To a stirred slurry of 17.29 g (40.0 mmol) of isopropyltriphenylphosphonium iodide and 500 mg (2 mmol) of 18-crown-6 in 100 mL of THF under nitrogen at 5° C. was added 4.50 g (40.0 mmol) of potassium t-butoxide over 5 minutes. The resulting deep red-orange slurry was stirred 10 minutes and then a solution of 6.50 g (35.0 mmol) of p-bromobenzaldehyde in 40 mL of THF was added at a rate to keep the temperature below +10° C. The resulting bright yellow slurry was stirred for 20 minutes and then poured into 300 mL of hexanes. The solids were filtered off and the filtrate evaporated. This residue was purified by flash chromatography (5×15 cm column) and eluted with hexanes to provide 5.66 g (77%) of title compound as a colorless oil.

TLC Silica gel (hexanes) $R_f=0.32$. $^1$H NMR (CDCl$_3$, 270 MHz): δ7.40 (d, 2H, J=8.4 Hz), 7.05 (d, 2H, J=8.4 Hz), 6.17 (s, 1H), 1.88 (s, 1H), 1.81 (s, 1H) ppm.

MICROANALYSIS Calc'd for C$_{10}$H$_{11}$Br: C, 56.90; H, 5.25. Found: C, 56.83; H, 5.22.

MS (CI-NH$_3$, −ions) m/e 209 (M-H).

B. 4-(2-Methyl-1-propenyl)benzaldehyde

To a stirred solution of 5.26 g (24.9 mmol) of Part A bromide in 25 mL of THF under argon at −70° C. was added 10.5 mL (26.3 mmol) of 2.5 M n-butyl lithium in hexanes over 10 minutes. A purple color appeared after the first few drops and finally an extremely thick slurry formed. After stirring for 30 minutes, 2.3 mL (30.0 mmol) of DMF in 4 mL THF was added rapidly to the reaction mixture. The temperature rose to −40° C. and a colorless, homogeneous solution resulted. The reaction was warmed to 0° C., quenched with 10% citric acid and partitioned between ether and water. The aqueous layer was re-extracted with ether; the extracts were combined, washed three times with water, dried (MgSO$_4$), filtered and evaporated. The crude product was purified by flash chromatography (5×20 cm column) eluted with 3:5 dichloromethane/hexanes to provide 3.74 g (94%) of title aldehyde as a colorless oil.

TLC Silica gel (3:7 dichloromethane/hexanes) $R_f=0.20$.

IR (CHCl$_3$ film) 2927, 2830, 1690, 1603, 1357, 760 cm$^{-1}$.

$^1$H NMR (CDCl$_3$, 270 mHz): δ9.97 (s, 1H), 7.81 (d, 2H, J=8.2 Hz), 7.36 (d, 2H, J=8.2 Hz), 6.30 (br s, 1H), 1.94 (d, 3H, J=1.7 Hz), 1.90 (d, 3H, J=1.2 Hz) ppm.

MS (CI-NH$_3$, +ions) m/e 161 (M+H), 178 (M+NH$_4$).

C. (E)-3-[4-(2-Methyl-1-propenyl)phenyl]2-propenoic acid, methyl ester

To a stirred slurry of 1.00 g (25.0 mmol) of 60% mineral oil dispersion of NaH in 50 mL of THF under argon at room temperature was added 4.05 mL (25.0 mmol) of trimethyl phosphonoacetate over 30 seconds. The reaction bubbled vigorously and autogenously refluxed. The resulting thick slurry was stirred at 50° C. for 30 minutes and then a solution of 3.50 g (21.8 mmol) Part B aldehyde in 10 mL THF was added rapidly. A clear solution formed almost at once. After 1 hour, the reaction was cooled to room temperature, diluted with 250 mL ether, washed twice with saturated sodium bicarbonate solution, dried (MgSO$_4$) and evaporated onto 15 g silica gel. The product was purified by flash chromatography (5×15 cm column) eluted with 500 mL hexanes and then dichloromethane to give 4.40 g (93%) of title ester as a white solid, mp 60°-61° C.

TLC Silica gel (1:1 dichloromethane/hexanes) R$_f$=0.34.

IR (KBr) 2969, 1715, 1632, 1600, 1435, 1316, 1172 cm$^{-1}$.

$^1$H NMR (CDCl$_3$, 270 MHz): δ7.67 (d, 1H, J=15.8 Hz), 7.46 (d, 2H, J=8.2 Hz), 7.23 (d, 2H, J=8.2 Hz), 6.40 (d, 1H, J=15.8 Hz), 6.25 (br s, 1H), 3.82 (s, 3H), 1.91 (s, 3H), 1.90 (s, 3H) ppm.

MICROANALYSIS Calc'd for C$_{14}$H$_{16}$O$_2$: C, 77.75; H, 7.46 Found: C, 77.87; H, 7.68.

D. 4-(2-Methyl-1-propenyl)benzenepropanoic acid, methyl ester

To a stirred slurry of 1.75 g (8.1 mmol) Part C ester in 40 mL methanol at 10°-12° C. under argon was added 395 mg (16.2 mmol) of magnesium turnings. After ca. 15 minutes gas bubbles formed at the metal surface and a cloudy solution formed. The reaction was closely kept at 10°-12° C. for 2 hours, and then quenched with 10% citric acid to neutrality, extracted three times with dichloromethane, dried (MgSO$_4$) and evaporated to provide 1.76 g (100%) of title ester as a colorless oil. The product was used in subsequent reactions without purification.

TLC Silica gel (1:1 dichloromethane/hexanes) R$_f$=0.34.

IR (CHCl$_3$ solution) 2955, 1732, 1512, 1439, 868 cm$^{-1}$.

$^1$H NMR (CDCl$_3$, 270 MHz): δ7.13 (br s, 4H), 6.22 (br s, 1H), 3.66 (s, 3H), 2.93 (t, 2H, J=7.0 Hz), 2.62 (t, 2H, J=7.0 Hz), 1.88 (d, 3H, J=1.8 Hz), 1.84 (d, 3H, J=1.2 Hz) ppm.

MS (CI-NH$_3$, +ions) m/e 219 (M+H).

E. 4-(2-Methyl-1-propenyl)benzenepropanol

To a stirred solution of 1.80 g (8.3 mmol) of Part D ester in 10 mL of THF under argon was added 5.0 mL (5.0 mmol) of a 1M solution of lithium aluminum hydride in THF over 1 minute. After 1 hour, the reaction was quenched with ca. 0.2 mL brine, diluted with ether, washed with 10% citric acid, dried (MgSO$_4$) and evaporated. Purification by flash chromatography (5x15 cm column) eluted with 1:25 ether/dichloromethane afforded 1.45 g (92%) of title alcohol as a colorless oil.

TLC Silica gel (1:24 ether/dichloromethane) R$_f$=0.2.

IR (CHCl$_3$ solution) 3624, 3024, 2936, 2863, 1705, 1510, 1454, 1237 cm$^{-1}$.

$^1$H NMR (CDCl$_3$, 270 MHz): δ7.14 (br s, 4H), 6.25 (br s, 1H), 3.66 (br dt, 2H, J=3 Hz, ca. 8 Hz), 2.67 (t, 2H, J=7.7 Hz), 1.90 (m, 2H), 1.88 (d, 3H, J=1.1 Hz), 1.85 (d, 3H, J=1.1 Hz), 1.54 (t, 1H, J=ca 3 Hz) ppm.

F. 1-(3-Iodopropyl)-4-(2-methyl-1-propenyl)benzene

To a stirred solution of 1.37 g (7.20 mmol) of Part E alcohol, 2.08 g (8.0 mmol) of triphenylphosphine and 1.03 g (15.1 mmol) of imidazole in 40 mL of THF was added a solution of 1.83 g (7.2 mmol) of iodine in 20 mL of THF over 20 minutes. After 10 minutes, the light yellow reaction mixture was diluted with pentane and washed once each with 10% sodium bisulfite solution, water and brine. The organic layer was dried (MgSO$_4$) and evaporated onto 5 g silica gel. Purification by flash chromatography (5×15 cm column) eluted with pentane gave title iodide, 1.88 g (87%) as a colorless oil.

TLC Silica gel (pentane) R$_f$=0.44.

IR (CHCl3 solution) 2982, 2932, 1653, 1445, 1248, 1024 cm$^{-1}$.

$^1$H NMR (CDCl$_3$, 270 MHz): δ7.13 (br s, 4H), 6.23 (br s, 1H), 3.16 (t, 2H, J=6.5 Hz), 2.67 (t, 2H, J=7.3 Hz), 2.11 (quintet, 2H, J=7 Hz), 1.89 (d, 3H, J=1.2 Hz), 1.85 (d, 3H, J=1.2 Hz) ppm.

MS (CI-NH$_3$, +ion) m/e 300 (M+).

G. [4-[4-(2-Methyl-1-propenyl)phenyl]butylidene]bisphosphonic acid, tetraethyl ester To a stirred slurry of 750 mg (18.7 mmol) of 60% mineral oil dispersion of sodium hydride in 20 mL of DMF under argon at 0° C. was added, over 10 minutes, a solution of 5.35 g (18.6 mmol) of tetraethyl methylenediphosphonate in 10 mL of DMF. The ice bath was removed and the solution was stirred at ambient temperature for 30 minutes. A solution of 1.85 g (6.16 mmol) Part F iodide in 3 mL DMF was then added to the resulting clear solution. After 15 hours, 9 mL 1M potassium bisulfate solution was added and the volatiles evaporated at 40° C. under vacuum. The resulting semi-solid residue was partitioned between ether and water. The aqueous layer was extracted once with ether and the organic layers combined and dried (MgSO$_4$) The crude product (4.20 g) was purified by flash chromatography (8×35 cm column) eluted with 1:24 ethanol/ethyl acetate to give 2.09 g (74%) of title ester as a yellow oil.

TLC Silica gel (1:16 ethanol/ethyl acetate) R$_f$=0.34.

IR (CHCl3 solution) 3009, 2933, 2857, 1510, 1447, 1213, 872 cm$^{-1}$.

$^1$H NMR (CDCl$_3$, 270 MHz): δ7.12 (br s, 4H), 6.23 (br s, 1H), 4.14 (m, 8H), 2.61 (t, 2H, J=7.6 Hz), 2.29 (tt, 1H, J=5.3, 24.0 Hz), 1.90 (m, 4H), 1.89 (s, 3H), 1.84 (s, 3H), 1.30 (dt, 12H) ppm.

MS (CI-NH3, +ion) m/e 461 (M+H).

H. [4-[4-(2-Methyl-1-propenyl)phenyl]butylidene]bisphosphonic acid, trisodium salt To a stirred solution of 1.322 g (2.87 mmol) Part G ester and 1.15 mL (8.6 mmol) of 2,4,6-collidine in 12 mL of dichloromethane under argon at room temperature was added 2.30 mL (17.2 mmol) of bromotrimethylsilane. After 22 hours, the resulting clear solution was evaporated at 35° C. and the residue stirred for 1 hour with 17 mL 1M sodium hydroxide. The solution was lyophilized and then purified by MPLC (2.5×20 cm column of Mitsubishi Kasei Sepabeads SP207SS resin): 10.5 mL fractions, 7 mL/minute flow rate, eluted with 160 mL water, then a gradient of 1:3 isopropanol/water (450 mL) into water (500 mL). Fractions 13-21 pere collected, evaporated to ca. 10 mL volume and precipitated with acetone to give 820 mg (69%) of title product as a white, waxy solid. The material occluded acetone (⅛ mole equivalent, 1.6% by weight).

IR (KBr) 3428, 2965, 2926, 2861, 1640, 1101, 876, 548 cm$^{-1}$.

$^1$H NMR (D$_2$O, 270 MHz): δ7.15 (d, 2H, J=8.2 Hz), 7.08 (d, 2H, J=8.2 Hz), 6.14 (br s, 1H), 2.49 (t, 2H, J=6.5 Hz), 1.72 (s, 3H), 1.69 (s, 3H), 1.60 (m, 5H) ppm.

MICROANALYSIS

Calc'd for $C_{14}H_{19}Na_3O_6P_2 \cdot 2H_2O \cdot \frac{1}{2}C_3H_6O$: C, 37.74; H, 5.23; P, 13.54. Found: C, 37.60; H, 4.96; P, 13.56.

MS (FAB, +ion) m/e 371 (M+3H-2Na), 393 (M+H-Na), 415 (M+H), 437 (M+Na).

EXAMPLE 15

[4-[4-(4-Methyl-3-pentenyl)phenyl]butylidene]bisphosphonic acid, tripotassium salt

A. 1-(Bromomethyl)-4-(4-methyl-3-pentenyl)benzene

A description of the preparation of the title A. compound is set out in Example 23, Parts A to C.

B. 4-(4-Methyl-3-pentenyl)benzenepropanoic acid, 1,1-dimethylethyl ester

To a stirred solution of 20.0 mL (10.0 mmol) of 0.5M lithium diisopropylamide (LDA) in THF under argon at 0° C. was added 3.5 mL HMPA. The bright yellow solution was stirred 20 minutes and then cooled to −78° C. A solution of 1.45 mL (10.3 mmol) of t-butyl acetate in 3 mL THF was added over 5 minutes. After 30 minutes, a solution of 1.80 g (7.11 mmol) of Part A bromide in 3 mL THF was added over 10 minutes. After stirring 3 hours, the reaction was allowed to warm to room temperature in situ for 16 hours. The reaction was quenched with 10% citric acid and extracted three times with hexane. The organic extracts were combined, washed once with saturated NaHCO3 solution, dried ($Na_2SO_4$) and evaporated. Purification by flash chromatography (5×15 cm column) eluted with 1:2 dichloromethane/hexanes gave 1.78 g (87%) of title ester as a colorless oil.

TLC Silica gel (2:3 dichloromethane/hexanes) $R_f$=0.40. $^1$H NMR (CDCl$_3$, 270 MHz): δ7.09 (br s, 4H), 5.16 (m, 1H), 2.87 (t, 2H, J=7.6 Hz), 2.54 (m, 4H), 2.28 (q, 2H, J=7.3 Hz), 1.68 (s, 3H), 1.55 (s, 3H), 1.41 (s, 3H) ppm.

Anal. Calc'd for C C, 79.12; H, 9.78. Found: C, 79.13; H, 9.89.

MS (CI-NH$_3$, +ions) m/e 289 (M+H).

C. 4-(4-Methyl-3-pentenyl)benzenepropanol

To a stirred solution of 1.64 g (5.7 mmol) of Part B ester in 10 mL of THF under argon at room temperature was added 3.5 mL (3.5 mmol) of 1M lithium aluminum hydride in THF over 2 minutes. The resulting solution was heated at reflux for 16 hours. The reaction was cooled, quenched with 0.5 mL of brine, diluted with ether and filtered through MgSO$_4$ and Celite. The filtrate was evaporated and the residue was purified by flash chromatography (5×20 cm column, 1:49 ether/dichloromethane as eluent) to give 1.13 g (91%) of title alcohol as a colorless oil.

TLC Silica gel (CH$_2$Cl$_2$) $R_f$=0.18.

IR (CH$_2$Cl$_2$ film) 3383, 2926, 2857, 1636, 1512, 1451, 1375, 1057 cm$^{-1}$.

$^1$H NMR (CDCl$_3$, 270 MHz): δ7.10 (br s, 4H), 5.18 (td, 1H, J=7.1 Hz), 3.64 (t, 2H, J=5.7 Hz), 2.64 (m, 4H), 2.26 (q, 2H, J=7.5 Hz), 1.92 (br s, 1H), 1.86 (m, 2H), 1.68 (s, 3H), 1.56 (s, 3H) ppm.

MS (CI, NH$_3$, +ions) m/e 236 (M+NH$_4$)

D. 1-(3-Iodopropyl)-4-(4-methyl-3-pentenyl)benzene

To a stirred solution of 1.03 g (4.72 mmol) of Part C alcohol, 1.36 g (5.2 mmol) of triphenylphosphine and 675 mg (10.1 mmol) of imidazole in 20 mL of THF under argon at room temperature was added a solution of 1.32 g (5.20 mmol) of iodine in 10 mL of THF over 15 minutes. After 30 minutes, the light yellow cloudy solution was diluted with ether and washed once with 10% sodium bisulfite solution. The organic extract was dried (MgSO$_4$) and evaporated. The residue was purified by flash chromatography (5×15 cm column) eluted with hexanes to give 1.28 g (83%) of title iodide as a colorless oil.

TLC Silica gel (dichloromethane) $R_f$=0.61.

$^I$R (CH$_2$Cl$_2$ film) 2963, 2924, 2855, 1636, 1512, 1445, 1375, 1213, 822 cm$^{-1}$. $^1$H NMR (CDCl$_3$, 270 MHz): 6 7.24 (br s, 4H), 5.31 (br t, 1H, J=7 Hz), 3.29 (t, 2H, J=7 Hz), 2.82 (t, 2H, J=7 Hz), 2.74 (t, 2H, J=7 Hz), 2.43 (q, 2H, J=7 Hz), 2.24 (quintet, 2H, J=7 Hz), 1.83 (s, 3H), 1.70 (s, 3H) ppm.

MS (CI-NH$_3$, +ions) m/e 328 (M$^+$)

E. [4-[4-(4-Methyl-3-pentenyl)phenyl]-butylidene]bisphosphonic acid, tetraethyl ester To a stirred slurry of 480 mg (12 mmol) of a 60% mineral oil dispersion of sodium hydride in 10 mL of DMF under argon at 0° C. was added, over 10 minutes, a solution of 3.50 g (12.1 mmol) of tetraethyl methylenediphosphonate in 2 mL of DMF. The ice bath was removed and the solution was stirred at ambient temperature for 30 minutes. A solution of 1.25 g (3.8 mmol) of Part D iodide in 1 mL DMF was then added to the resulting clear solution. After 16 hours, 0.70 mL (12 mmol) of acetic acid was added and the volatiles evaporated at 40° C. under vacuum. The resulting semisolid residue was partitioned between ether and saturated sodium bicarbonate solution. The aqueous layer was extracted once with ether and the organic layers combined and dried (MgSO$_4$). The crude product was purified by flash chromatography (5×15 cm column) eluted with 1:15 ethanol/ethyl acetate to give 760 mg (41%) of title ester as a yellow oil.

TLC Silica gel (1:19 ethanol/ethyl acetate) $R_f$=0.22.

$^1$H NMR (CDCl$_3$, 270 MHz): δ7.09 (br s, 4H), 5.17 (br t, 1H, J=7 Hz), 4.14 (m, 8H), 2.59 (m, 4H), 2.30 (m, 3H), 1.93 (m, 4H), 1.68 (s, 3H), 1.57 (s, 3H), 1.31 (dt, 12H, J=5.8, 7.0 Hz) ppm.

F. [4-[4-(4-Methyl-3-pentenyl)phenyl]butylidene]bisphosphonic acid, tripotassium salt To a stirred solution of 0.66 g (1.35 mmol) of Part E ester and 0.55 mL (4.1 mmol) of 2,4,6-collidine in 10 mL of dichloromethane under argon at room temperature was added 1.1 mL (8.1 mmol) of bromotrimethylsilane. After 20 hours, the resulting clear solution was evaporated at 35° C. and the residue stirred for 1 hour with 14 mL of 1M potassium hydroxide. The solution was lyophilized and then purified by MPLC (2.5×25 cm column of Mitsubishi Kasei Sepabeads SP207SS resin): 8 mL fractions, 6.7 mL/minute flow rate, eluted with 160 mL water, then a gradient of 1:1 isopropanol:water (450 mL) into water (500 mL). Fractions 40–49 were collected, evaporated to ca. 30 mL volume and lyophilized to give 370 mg (52%) of title product as a white powder.

IR (KBr) 3397, 2967, 2857, 1512, 1439, 1375, 1107 20 cm$^{-1}$. $^1$H NMR (D$_2$O, 270 MHz): 6 7.15 (d, 2H, J=8.2 Hz), 7.10 (d, 2H, J=8.2 Hz), 5.12 (br t, 1H), 2.51 (m, 4H), 2.18 (q, 2H, J=7.0 Hz), 1.70 (m, 5H), 1.55 (s, 3H), 1.77 (s, 3H) ppm.

Anal. Calc'd for $C_{16}H_{23}K_3O_6P_2 \cdot 2H_2O$: C, 36.49; H, 5.17; P, 11.76. Found: C, 36.47; H, 4.98; P, 11.78.

MS (FAB, +ion) m/e 473 (M+2H-K), 491 (M+H), 529 (M+K).

EXAMPLE 16

(6,10-Dimethylundecylidene)bisphosphonic acid, tetrasodium salt

A. (6,10-Dimethylundecylidene)bisphosphonic acid, tetraethyl ester

A solution of 1.00 g (2.21 mmol) of Example 5 tetraethyl ester in 20 mL of ethanol was hydrogenated at 1 atm in the presence of 100 mg of 10% palladium on carbon for 24 hours, at which time the reaction was filtered through a cake of celite and the solvent evaporated. The oily residue was further purified through 40 g of silica gel, eluting with 5:95 $CH_3OH/CH_2Cl_2$. The product fractions were combined and evaporated to provide 860 mg (85%) of title ester as a colorless oil.

TLC Silica gel (95:5 dichloromethane/methanol) $R_f=0.36$.

IR ($CCl_4$) 2958, 2929, 2870, 1720, 1466, 1367, 1252, 1029 cm$^{-1}$.

$^1$H NMR (270 MHz, $CDCl_3$): δ4.18 (m, 6H), 2.27 (tt, 1H, J=5.9, 24.0 Hz), 1.92 (m, 2H), 1.55, 1.25, 1.20 (3 m, 14H), 1.34 (t, 12H, H=7.0 Hz), 0.86 (d, 6H, J=6.5 Hz), 0.84 (d, 3H, J=6.5 Hz) ppm.

MS (CI-$NH_3$, +ions) m/e 474 (M+$NH_4$), 457 (M+H).

B. (6,10-Dimethylundecylidene)bisphosphonic acid, tetrasodium salt

To a stirred solution of 860 mg (1.89 mmol) of Part A ester in 10 mL of dichloromethane at room temperature under argon was added 1.24 mL (9.43 mmol) of bromotrimethylsilane. The reaction stirred for 18 hours, at which time the solvent was evaporated and the residue was pumped (high vacuum) for 2 hours. The remainder was treated with 8.33 mL (8.33 mmol) of 1M NaOH and evaporated to dryness in vacuo. The crude residue was precipitated by dissolving the sample in 5 mL of water, warming to 50° C., treating the solution with 1 mL of acetone and placing the mixture in an ice bath. The precipitate was filtered and washed with 6 mL of 5:1 water/acetone. This washing procedure was performed three times, followed by a wash with 10 mL of 1:1 water/acetone and 10 mL of acetone. In each of the washings, the solids were triturated with a spatula in order to aid the extraction and solidification. The resulting fine white solids were pumped (high vacuum) for 18 hours to provide 453 mg (56%) of title product.

IR (KBr) 2955, 2926, 2868, 1466, 1098, 949, 552 cm$^{-1}$.

$^1$H NMR (400 MHz, $D_2O$): δ1.69 (m, 3H), 1.46, 1.35, 1.24, 1.09 (4m, 14H), 0.79 (d, 9H, J=6.6 Hz) ppm.

MS (FAB, +ions) m/e 455 (M+Na), 433 (M+H), 411 (M+2H-Na).

Anal. calc'd for $C_{13}H_{26}P_2O_6Na_4$·2.57 mol $H_2O$: Effective MW=478.46. C, 32.63; H, 6.56; P, 12.94 Found: C, 32.63; H, 6.70; P, 13.19.

EXAMPLE 17

[4-[3-(2-Methyl-1-propenyl)phenyl]butylidene]bisphosphonic acid, trisodium salt

3-Bromobenzaldehyde was obtained from Aldrich Chemical Company (#B 5,720-6) and was used without purification.

A. 1-Bromo-3-(2-methyl-1-propenyl)benzene

To a stirred slurry of 17.83 g (41.2 mmol) of isopropyltriphenylphosphonium iodide and 300 mg (1.1 mmol) of 18-crown-6 in 50 mL of THF under nitrogen at 5° C. was added 4.60 g (41.0 mmol) of potassium t-butoxide over 5 minutes. The resulting deep red-orange slurry was stirred 10 minutes and then a solution of 4.31 mL (37.0 mmol) of 3-bromobenzaldehyde in 40 mL of THF was added at a rate to keep the temperature below 10° C. The resulting bright yellow slurry was stirred for 20 minutes and then poured into 300 mL of hexanes. The solids were filtered off and the filtrate evaporated. This residue was purified by flash chromatography (5×15 cm column) and eluted with hexanes to provide 5.88 g (75%) of title compound as a colorless oil.

TLC Silica gel (hexanes) $R_f=0.33$.

$^1$H NMR ($CDCl_3$, 270 MHz): δ7.35 (s, 1H), 7.28 (dt, 1H, J=2.0, 7.0 Hz), 7.12 (m, 2H), 6.17 (br s, 1H), 1.88 (d, 3H, J=1.1 Hz), 1.83 (d, 3H, J=1.1 Hz) ppm.

MS (CI-$NH_3$, +ions) m/e 210 (M+.).

B. 3-(2-Methyl-1-propenyl)benzaldehyde

To a stirred solution of 5.85 g (27.7 mmol) of Part A compound in 50 mL of THF under argon at −70° C. was added 13 mL (32.5 mmol) of 2.5M n-butyl lithium in hexanes over 10 minutes. After stirring for 30 minutes, 4 mL (54 mmol) of DMF was added rapidly to the reaction mixture. The temperature rose to −40° C. and a colorless, homogeneous solution resulted. The reaction was warmed to 0° C., quenched with 10% citric acid and partitioned between ether and water. The aqueous layer was re-extracted with ether; the extracts were combined, washed three times with water, dried (MgSO$_4$), filtered and evaporated. The crude product was purified by flash chromatography (5×15 cm column) eluted with 1:3 dichloromethane/hexanes to provide 3.84 g (87%) of title aldehyde as a colorless oil.

TLC Silica gel (3:7 dichloromethane/hexanes) $R_f=0.22$.

IR (CHCl$_3$ film) 2927, 2830, 1690, 1603, 1357, 760 cm$^{-1}$.

$^1$H NMR (CDCl$_3$, 270 MHz) δ9.99 (s, 1H), 7.68 (m, 2H), 7.46 (m, 2H), 6.29 (s, 1H), 1.92 (s, 1H), 1.86 (s, 1H) ppm.

MS (CI-NH$_3$, +ions) m/e 161 (M+H).

C. 3-[3-(2-Methyl-1-propenyl)phenyl]-2-propenoic acid, methyl ester

To a stirred slurry of 0.46 g (11.5 mmol) 60% mineral oil dispersion of NaH in 25 mL of tetrahydrofuran under argon at room temperature was added 1.94 mL (12.0 mmol) of trimethyl phosphonoacetate over 30 seconds. The reaction bubbled vigorously and autogenously refluxed. The resulting thick slurry was stirred at 50° C. for 30 minutes and then a solution of 1.60 g (10.0 mmol) of Part B aldehyde in 10 mL of tetrahydrofuran was added rapidly. A clear solution formed almost at once. After 1 hour, the reaction was cooled to room temperature, diluted with 250 mL ether, washed twice with saturated sodium bicarbonate solution, dried (MgSO$_4$) and evaporated onto 10 g silica gel. The product was purified by flash chromatography (5×15 cm column) eluted with 500 mL hexanes and then dichloromethane to give 1.56 g (72%) of title ester as a colorless oil.

TLC Silica gel (1:1 dichloromethane/hexanes) $R_f=0.35$.

IR (KBr) 2969, 1715, 1632, 1600, 1435, 1316, 1172 cm$^{-1}$.

$^1$H NMR (CDCl$_3$, 270 MHz) δ7.69 (d, 1H, J = 16.4 Hz), 7.1-7.3 (m, 4H), 6.42 (d, 1H, J = 16.4 Hz) 6.24 (br, s, 1H), 3.79 (s, 3H), 1.90 (s, 3H), 1.85 (s, 3H), ppm.

MS (CI-NH$_3$, +ions) m/e 217 (M+H).

D. 3-(2-Methyl-1-propenyl)benzenepropanoic acid, methyl ester

To a stirred solution of 1.32 g (6.1 mmol) of Part C compound in 30 mL of methanol (dried over 3A sieves) at 10°-12° C. under argon was added 300 mg (12.2 mmol) of magnesium turnings. After ca. 15 minutes, gas bubbles formed at the metal surface and a cloudy solution formed. The reaction was closely kept at 10°-12° C. for 2 hours, and then quenched with 25 mL of 1M hydrochloric acid, extracted twice with ether, dried (MgSO$_4$) and evaporated to provide 1.32 g (100%) of title compound as a colorless oil. The product was used in subsequent reactions without purification.

TLC Silica gel (dichloromethane) $R_f=0.48$.

IR (CHCl$_3$ solution) 2955, 1732, 1512, 1439, 868 cm$^{-1}$.

$^1$H NMR (CDCl$_3$, 270 MHz): δ7.40 (m, 1H), 7.24 (m, 3H), 6.43 (br s, 1H), 3.84 (s, 3H), 3.12 (t, 2H, J=7.7 Hz), 2.84 (t, 2H, J=7.0 Hz), 2.07 (d, 3H, J=1.2 Hz), 2.03 (d, 3H, J=1.1 Hz) ppm.

MS (CI-NH$_3$), +ions) m/e 219 (M+H).

E. 3-(2-Methyl-1-propenyl)benzenepropanol

To a stirred solution of 1.30 g (6.0 mmol) of Part D compound in 10 mL of tetrahydrofuran under argon was added 4.0 mL (4.0 mmol) of a 1M solution of lithium aluminum hydride in tetrahydrofuran over 1 minute. After 1 hour, the reaction was quenched with ca. 0.2 mL brine, diluted with ether, washed with 10% citric acid, dried (MgSO$_4$) and evaporated. Purification by flash chromatography (5×20 cm column) eluted with 1:32 ether/dichloromethane afforded 1.13 g (99%) of title alcohol as a colorless oil.

TLC Silica gel (1.33 ether/dichloromethane) $R_f=0.23$.

IR (CHCl$_3$ solution) 3333, 2932, 2863, 1657, 1451, 1057, 702 cm$^{-1}$.

$^1$H NMR (CDCl$_3$, 270 MHz) δ7.21 (m, 1H), 7.04 (m, 3H), 6.24 (br s, 1H), 3.63 (t, 2H, J = 6.4 Hz), 2.67 (t, 2H, J = 7.6 Hz), 2.12 (s, 1H), 1.88 (s, 3H), 1.86 (m, 2H), 1.85 (s, 3H) ppm.

MS (CI-NH$_3$ +ions) m/e 190 (M+)

F. 1-(3-Iodopropyl)-3-(2-methyl-1-propenyl)benzene

To a stirred solution of 740 mg (3.90 mmol) of Part E alcohol, 1.01 g (3.9 mmol) of triphenylphosphine and 560 mg (8.0 mmol) of imidazole in 15 mL of tetrahydrofuran was added a solution of 990 mg (3.90 mmol) iodine in 5 mL of tetrahydrofuran over 20 minutes. After 10 minutes, the light yellow reaction mixture was diluted with pentane and washed once each with 10% sodium bisulfite solution, water and brine. The organic layer was dried (MgSO$_4$) and evaporated onto 5 g silica gel. Purification by flash chromatography (5×15 cm column) eluted with pentane gave title iodide 0.89 g, (76%), as a colorless oil.

TLC Silica gel (pentane) $R_f$0.48.

$^1$H NMR(CDCl$_3$, 270 MHz) δ7.22 (m, 1H), 7.04 (m, 3H), 6.24 (br s, 1H), 3.16 (t, 2H, J = 7.0 Hz), 2.70 (t, 2H, J = 8.0 Hz), 2.11 (tt, 2H, J = 7.0, 8.0 Hz), 1.89 (s, 3H), 1.85 (s, 3H) ppm.

MS (CI-NH$_3$, +ion) m/e 300 (M+).

G. [4-[3-(2-Methyl-1-propenyl)phenyl]butylidene]bisphosphonic acid, tetraethyl ester To a stirred slurry of 356 mg (8.9 mmol) of 60% mineral oil dispersion of sodium hydride in 10 mL of dimethylformamide under argon at 0° was added, over 10 minutes a solution of 2.59 g (9.0 mmol) of tetraethyl methylenediphosphonate in 10 mL of dimethylformamide. The ice bath was removed and the solution was stirred at ambient temperature for 30 minutes. A solution of 0.89 g (3.0 mmol) of Part F compound in 2 mL dimethylformamide was then added to the resulting clear solution. After 15 hours, 0.52 mL (8.9 mmol) of acetic acid was added and the volatiles evaporated at 40° C. under vacuum. The resulting semi-solid residue was partitioned between ether and saturated sodium bicarbonate solution. The aqueous layer was extracted once with ether and the organic layers combined and dried (MgSO$_4$). The crude product was purified by flash chromatography (5×15 cm column) eluted with 1:22 ethanol/ethyl acetate to give 830 mg (61%) of title ester as a yellow oil.

TLC Silica gel (1: 22 ethanol/ethyl acetate) $R_f=0.25$.

IR (CHCl$_3$ solution) 2980, 2930, 2870, 1601, 1445, 1244, 1024, 972 cm$^{-1}$.

$^1$H NMR (CDCl$_3$, 270 MHz) δ 7.21 (m, 1H), 7.02 (m, 3H), 6.24 (br s, 1H), 4.14 (m, 8H), 2.62 (t, 2H, J = 6.7 Hz) 2.30 (tt, 1H, J = 5.3, 24.2 Hz), 1.90 (m, 4H), 1,89 (s, 3H), 1.85 (s, 3H), 1.3 (dt, 12H, J = 1.2, 7Hz) ppm.

MS (CI-NH$_3$, +ion) m/e 461 (M+H).

H. [4-[3-(2-Methyl-1-propenyl)phenyl]butylidene]bisphosphonic acid, trisodium salt To a stirred solution of 820 mg (1.78 mmol) Part G ester and 0.73 mL (5.3 mmol) of 2,4,6-collidine in 10 mL of dichloromethane under argon at room temperature was added 1.45 mL (10.6 mmol) of bromotrimethylsilane. After 22 hours, the resulting clear solution was evaporated at 35° C. and the residue stirred for 1 hour with 11 mL 1M sodium hydroxide. The solution was lyophilized and then purified by MPLC (2.5×25 cm column of Mitsubishi Kasei Sepabeads SP207SS resin): 10.7 mL fractions, 8.2 mL/min flow rate, eluted with 160 mL water, then a gradient of 1:3 isopropanol: water (500 mL) into water (500 mL). Fractions 20–32 were collected, evaporated to ca. 10 mL volume and added dropwise to 35 mL of methanol at room temperature. Cooling to 0° C. gave 350 mg (45%) of title product as a white solid.

IR (KBr) 3428, 2928, 2860, 1636, 1485, 1448, 1157, 880 cm$^{-1}$.

$^1$H NMR (D$_2$O, 270 MHz) δ7.21 (m, 1H), 7.0 (m, 3H), 6.18 (br s, 1H), 2.51 (t, 2H, J=5.5 Hz), 1.76 (s, 3H), 1.72 (s, 3H), 1.70 (m, 5H) ppm.

MS (FAB, +ion) m/e 371 (M+3H-2Na), 393 (M+2H-Na), 415 (M+H), 437 (M+Na).

Anal. Cald'd for C$_{14}$H$_{19}$Na$_3$O$_6$P$_1$·1.25 H$_2$O: C, 38.50; H, 4.96; P, 14.19. Found: C, 38.45; H, 5.11; P, 14.16.

EXAMPLE 18

[4-([1,1'-Biphenyl]-4-yl)butylidene]bisphosphonic acid, tetrasodium salt

A. (E)-3-([1,1']-Biphenyl]-4-yl)-2-propenoic acid, methyl ester

Sodium hydride (2.40 g, 60 wt. % in mineral oil, 60.3 mmol) was washed with hexane (2×50 mL), then suspended in THF (125 mL) under argon. Trimethyl phosphonoacetate (9.8 mL, 60.3 mmol) was added to the suspension over 20 minutes (mild exotherm). A thick precipitate formed and was stirred at room temperature for 30 minutes, then at 50° C. for 30 minutes. After cooling to 0° C., a solution of 4-biphenylcarboxaldehyde (10.0 g, 54.9 mmol) in THF (40 mL) was added over 20 minutes, at which time the precipitate dissolved. The reaction mixture was allowed to stir at 0° C for 1 hour, then at room temperature for 1 hour. The reaction mixture was diluted with $CH_2Cl_2$ and washed with saturated $NH_4Cl$ and water, then dried over $MgSO_4$. Evaporation gave the crude product, which was recrystallized from EtOAc/hexane to afford title ester (7.82 g, 60%) as white plates (mp 147°-149° C.). The mother liquor was concentrated in vacuo and the resultant solid was recrystallized from $CH_3OH$ to afford additional title ester (1.90 g, 15%) as white plates (mp 147°-149° C.). Total yield of title ester: 9.72 g (75%).

TLC Silica gel (1:1 $CH_2Cl_2$/hexane) $R_f=0.24$.

IR (KBr) 3063, 2992, 2944, 1719, 1636, 1327, 1312, 1198, 1184, 1173, 984, 833, 772, 737, 689 cm$^{-1}$.

$^1$H NMR (CDCl$_3$, 270 MHz): δ7.74 (d, 1H, J=16.4 Hz), 7.61 (m, 6H), 7.46 (t, 2H, J=7.6 Hz), 7.37 (m, 1H), 6.48 (d, 1H, J=16.4 Hz), 3.82 (d, 3H, J=1.2 Hz) ppm.

Anal. Calc'd for $C_{16}H_{14}O_2$: C, 80.65; H, 5.92 Found: C, 80.38; H, 5.90.

B. 3-([1,1'-Biphenyl]-4-yl)propanoic acid, methyl ester

A mixture of Part A ester (3.0 g, 12.6 mmol) and 10% palladium on carbon (150 mg) in THF (50 mL) was maintained under a balloon of hydrogen for 22 hours, then filtered through a layered pad of silica gel under Celite. The solids were washed with THF (200 mL), and the filtrate was evaporated to provide title ester (3.0 g, 99%) as a white solid. mp: 58°-58.5° C.

TLC Silica gel (1:1 $CH_2Cl_2$/hexane) $R_f=0.25$.

IR (KBr) 3030, 2957, 1742, 1487, 1437, 1165 cm$^{-1}$.

$^1$H NMR (CDCl$_3$, 270 MHz) δ7.57 (dm, 2H, J=7 Hz), 7.52 (dm, 2H, J=7 Hz), 7.42 (tm, 2H, J=7 Hz), 7.29 (m, 3H), 3.68 (s, 3H), 2.99 (t, 2H, J=7.6 Hz), 2.67 (t, 2H, J=7.6 Hz) ppm.

Anal. Calc'd for $C_{16}H_{16}O_2$: C, 79.97; H, 6.71 Found: C, 79.79; H, 6.67.

C. 4-(3-Iodopropyl)-1,1'-biphenyl

Lithium aluminum hydride (17.6 mL, 1.0M in THF, 17.6 mmol) was added dropwise quickly over 15 minutes to a solution of Part B ester (4.23 g, 17.6 mmol) in THF (100 mL) at 0° C. under argon. The opaque reaction mixture was stirred at 0° C. for an additional 15 minutes, then quenched by addition of hydrated $Na_2SO_4$ until gas evolution ceased. The resultant gelatinous suspension was diluted with EtOAc (100 mL), filtered through Celite, and washed with EtOAc (200 mL). The filtrate was evaporated to give 3.80 g of a white solid.

The alcohol prepared above was dissolved in $CH_2Cl_2$ and cooled to 0° C. under argon. Triethylamine (4.9 mL, 35.2 mmol) was added, followed by dropwise addition of methanesulfonyl chloride (1.5 mL, 19.4 mmol) over 5 minutes. The resultant cloudy yellow reaction mixture was stirred at 0° C. for 15 minutes, diluted with $CH_2Cl_2$ (200 mL), and washed with 1N HCl (75 mL), saturated $NaHCO_3$ (50 mL), and brine. After drying over $MgSO_4$, the solvent was evaporated to give 5.27 g of a white solid.

The mesylate prepared above was dissolved in acetone (150 mL) under argon. Sodium iodide (13.2 g, 88.0 mmol) was added, and the resultant heterogeneous mixture was heated to and maintained at reflux for 1.5 hours, then cooled to room temperature. The reaction mixture was concentrated in vacuo and the resultant yellow solid was partitioned between $CH_2Cl_2$ (150 mL) and water (75 mL). The organic layer was washed with brine (50 mL), then dried over $MgSO_4$ Evaporation gave a yellow oil, which was purified by flash chromatography on silica gel (75 g) eluting with hexane to give title iodide (5.27g, 93%) as a colorless oil which crystallized on standing. mp: 42°-44° C.

TLC Silica gel (Hexane) $R_f=0.10$.

IR (KBr) 3055, 3030, 2936, 1487, 1449, 1406, 1169, 752 cm$^{-1}$.

$^1$H NMR (CDCl3, 270 MHz) δ 7.50, 7.55 (two dm, 2H each, J=7 Hz), 7.41 (tm, 2H; J=7 Hz), 7.31 (tm, 1H, J=7 Hz), 7.25 (d, 2H, J=7.6 Hz), 3.18 (t, 2H, J=7 Hz), 2.75 (t, 2H, J=7 Hz), 2.14 (quint, 2H, J=7 Hz) ppm.

MS (CI-NH$_3$, +ions) m/z 340 (M+NH$_4$), 322 (M+H).

Anal. Calc'd for $C_{15}H_{15}I$: C, 55.92; H, 4.69 Found: C, 55.88; H, 4.57.

D. [4-([1,1'-Biphenyl]-4-yl)butylidene]bisphosphonic acid, tetraethyl ester

To a suspension of 290 mg (7.26 mmol) of 60% NaH in mineral oil in 3 mL of DMF was added 1.86 mL (7.50 mmol) of tetraethyl methylenediphosphonate neat over 10 minutes with much gas evolution. After 30 minutes at room temperature, the mixture was cooled to 0° C. and 780 mg (2.42 mmol) of Part C. iodide in 5 mL of DMF was added and the reaction was allowed to warm to room temperature and stir for 72 hours. The mixture was diluted with saturated NH$_4$Cl, and the organic layer was washed with water and brine, dried (MgSO$_4$) and evaporated to provide 982 mg of a yellow oil. Flash chromatography on 100 g of silica gel eluted with 2:98 $CH_3OH/CH_2Cl_2$ provided 503 mg (43%) of title compound contaminated with a trace of tetraethyl methylenediphosphonate. The material was rechromatographed on 50 g of silica gel eluted with 1.5:98.5 $CH_3OH/CH_2Cl_2$ to provide 408 mg (35%) of the tetraester as a colorless oil.

IR (CH$_2$Cl$_2$) 2986, 1638, 1487, 1392, 1240, 1163, 1022, 974 cm$^{-1}$.

$^1$H-NMR (CDCl$_3$, 270 MHz): δ 7.50, 7.56 (two dm, 2H each, J=7 Hz), 7.41 (tm, 2H, J=7 Hz), 7.31 (tm, 1H, J=7 Hz), 7.25 (d, 2H, J=8 Hz), 4.16 (m, 8H), 2.69 (t, 2H, J=7 Hz), 2.31 (tt, 1H, J=5.3 and 24 Hz), 1.98 (m, 4H), 1.31 (t, 12H, J=7 Hz) ppm.

MS (CI-NH$_3$, +ions) m/z 500 (M+NH$_4$), 483 (M+H).

Anal. Calc'd for $C_{24}H_{36}O_6P_2$+0.69 equiv H$_2$O: C, 58.25; H, 7.61; P, 12.52.

Found: C, 58.14; H, 7.56; P, 12.85.

E. [4-([1,1'-Biphenyl]-4-yl)butylidene]bisphosphonic acid

To a stirred solution of 382 mg (0.792 mmol) of Part D ester in 5 mL of CH$_2$Cl$_2$ under argon at room temperature was added 0.63 mL (4.75 mmol) of TMSBr and the reaction was allowed to stir at room termperature for 18 hours. The solvent was evaporated and traces of volatiles were pumped off at high vacuum for 1 hour. The remainder was dissolved in 20 mL of methanol, stirred for 1 hour, and then evaporated. The sticky, semisolid residue was triturated with ether, and the resulting yellow-white solid was recrystallized from acetone/ether to provide 235 mg (81%) of title product as a white powder, mp 199°-200° C.

$^1$H-NMR (CD$_3$OD, 400 MHz): δ 7.56 (d, 2H, J=7.3 Hz), 7.50 (d, 2H, J=8.1 Hz), 7.41 (dd, 2H, J=7.3 and.8 Hz), 7.31 (m, 3H), 2.69 (t, 2H, J=7 Hz), 2.24 (tt, 1H, J=6 and 23 Hz), 1.99 (m, 4H) ppm.

MS (FAB, +ions) m/z 393 (M+Na), 371 (M+H).

Anal. Calc'd for C$_{16}$H$_{20}$O$_2$+0.40 equiv H$_2$O: C, 50.92; H, 5.54; P, 16.41.

Found: C, 50.92; H, 5.50; P, 16.50.

F. [4-([1,1'-Biphenyl]-4-yl)butylidene]bisphosphonic acid, tetrasodium salt

A mixture of Part E acid (3.50 g, 9.46 mmol) and 1N NaOH (39.7 mL, 39.7 mmol) in water (40 mL) was stirred at room temperature until all of the solid had dissolved. The reaction mixture was heated to 45° C., at which time acetone was added in aliquots (150 mL total) until the mixture became cloudy. The reaction mixture was allowed to cool to room temperature, then was cooled at 4° C. for 2 hours. The precipitate was filtered and washed with 4:1 acetone/water (3×30 mL) and air-dried. The gummy solid obtained was pumped under vacuum overnight to give 2.62 g of a white solid, which contained a minor impurity by $^1$H NMR. The product was purified by chromatography on SP207SS gel (5×20 cm column) eluted with water. Approximately 25 mL fractions were collected. Fractions 20-36 were combined and lyophilized to give title salt (2.17 g, 50%) as a white solid.

IR (KBr) 3424, 2934, 1638, 1487, 1107, 847, 762, 698 cm$^{-1}$.

$^1$H NMR (D$_2$O, 270 MHz) δ 7.57 (d, 2H, J=7.3 Hz), 7.52 (d, 2H, J=7.7 Hz), 7.39 (t, 2H, J=7.3 Hz), 7.30 (m, 3H), 2.60 (t, 2H, J=6.7 Hz), 1.75 (m, 5H) ppm.

$^{31}$P NMR (D$_2$O, 36.2 MHz) δ 20.3 (s) ppm.

MS (FAB, −ions) m/z 391 (M+2H-3Na), 369 (M+3H-4Na), 351 (M+3H-4Na-H$_2$O).

Anal. Calc'd for C$_{16}$H$_{16}$Na$_4$O$_6$P$_2$.2.6 equiv H$_2$O: C, 38.05; H, 4.23; P, 12.27

Found: C, 37.78; H, 4.27; P, 12.65.

EXAMPLE 19

[4-(4-Propylphenyl)butylidene]bisphosphonic acid

A. 4-Propylbenzenemethanol

To a stirred solution of 5.09 g (30.6 mmol) of 4-propylbenzoic acid in 50 mL of THF under argon at room temperature was added 1.0 g (26 mmol) of powdered lithium aluminum hydride over 10 minutes. The resulting gray slurry was heated to reflux for 6 hours. The reaction was cooled to room temperature and cautiously quenched with ca. 1 mL of brine. When the slurry had become completely white, it was diluted with ether, dried (MgSO$_4$) and evaporated. Bulb-to-bulb distillation (0.5 mm Hg, 160° C.) afforded 4.25 g (91%) of title alcohol as a colorless oil.

TLC Silica gel (1:49 ether/dichloromethane) R$_f$=0.31.

$^1$H NMR (CDCl$_3$, 270 MHz): δ 7.25 (d, 2H, J=8.2 Hz), 7.15 (d, 2H, J=8.2 Hz), 4.61 (s, 2H), 2.58 (t, 2H, J=7.0 Hz), 1.94 (s, 1H), 1.61 (sextet, 2H, J=7.0 Hz), 0.93 (t, 3H, J=7.0 Hz) ppm.

MS (CI-NH$_3$, +ions) m/e 153 (M+H).

B. 1-(Bromomethyl)-4-propylbenzene

To a stirred solution of 3.71 g (24.7 mmol) of Part A alcohol and 7.12 g (27.2 mmol) of triphenylphosphine in 100 mL of dichloromethane at −42° C. under argon was added 4.84 g (29.5 mmol) of powdered, recrystallized N-bromosuccinimide over 20 minutes. The reaction temperature was not allowed to rise above −35° C. After 30 minutes, the reaction was evaporated onto 15 g silica gel. Purification by flash chromatography (5×15 cm column) eluting with pentane provided 4.49 g (85%) of title bromide as a colorless oil.

TLC Silica gel (pentane) R$_f$=0.62.

IR (film) 2959, 2930, 2870, 1514, 1227, 1202, 606 cm$^{-1}$.

$^1$NMR (CDCl$_3$, 270 MHz): δ 7.28 (d, 2H, J=8.2 Hz), 7.13 (d, 2H, J=8.2 Hz), 4.46 (s, 2H), 2.56 (t, 2H, J=7.0 Hz), 1.60 (sextet, 2H, J=7.0 Hz), 0.92 (t, 3H, J=7.0 Hz).

MS (CI-NH$_3$, +ions) m/e 213 (M+H).

C. 4-Propylbenzenepropanoic acid, t-butyl ester

To a stirred solution of 46 mL (14.5 mmol) of 0.32M lithium diisopropylamide in 7:1 THF/hexane under argon at −10° C., was added 7.0 mL (40 mmol) of HMPA. The resulting yellow solution was stirred for 20 minutes, cooled to −78° C., and then 1.93 mL (14.3 mmol) of neat t-butyl acetate was added at a rate to keep the temperature below −65° C. The resulting nearly colorless solution was stirred for 30 minutes and then a solution of 3.00 g (14.1 mmol) of Part B bromide in 10 mL of THF was added over 10 minutes. The solution was maintained at −78° C. for 72 hours. The reaction was quenched with 10% citric acid solution and extracted twice with ether.

The ether extracts were combined, washed twice with water, once with saturated sodium bicarbonate solution, once with 10% sodium bisulfite solution and once with brine. After drying (MgSO$_4$), the crude product was purified by flash chromatography (5×20 cm column) eluting with 1:3 dichloromethane/hexanes to give 3.45 g (99%) of title ester as a colorless oil.

TLC Silica gel (2:3 dichloromethane/hexanes) R$_f$=0.38.

$^1$H NMR (CDCl$_3$, 270 MHz): δ 7.08 (s, 4H), 2.87 (t, 2H, J=8.2 Hz), 2.54 (t, 2H, J=7.0 Hz), 2.51 (t, 2H, J=7.6 Hz), 1.60 (m, 2H), 1.40 (s, 9H) ppm.

MS (CI-NH$_3$, +ions) m/e 249 (M+H).

D. 4-Propylbenzenepropanol

To a stirred solution of 2.42 g (9.7 mmol) of Part C ester in 10 mL THF at room temperature was added a solution of 6.0 mL (6.0 mmol) of 1M lithium aluminum hydride in THF over 1 minute. The cloudy solution was set to reflux for 15 hours. The reaction was then cooled, quenched with brine and extracted three times with ether. The extracts were combined, dried (MgSO$_4$) and evaporated onto 5 g of silica gel. Purification by flash chromatography (2.5 × 10 cm column) eluted with dichloromethane gave 1.48 g (86%) of title alcohol as a colorless oil.

TLC Silica gel (1:49 ether/dichloromethane) $R_f=0.36$.

IR (thin film) 3337, 3007, 2930, 2870, 1514, 1454, 1061, 1040 cm$^{-1}$.

$^1$H NMR (CDCl$_3$, 270 MHz): δ 7.24 (br s, 4H), 3.77 (t, 2H, J=6.5 Hz), 2.80 (t, 2H, J=7.6 Hz), 2.70 (t, 2H, J=7.2 Hz), 2.48 (br s, 1H), 2.03 (m, 2H), 1.76 (sextet, 2H, J=7.6 Hz), 1.09 (t, 3H, J=7.6 Hz) ppm.

MS (CI-NH$_3$, +ions) m/e 196 (M+NH$_4$).

E. 1-(3-Iodopropyl)-4-propylbenzene

To a stirred solution of 1.443 g (8.10 mmol) of Part D alcohol, 2.12 g (8.10 mmol) of triphenylphosphine and 1.18 mg (16.2 mmol) of imidazole in 30 mL of THF was added a solution of 2.06 g (8.1 mmol) of iodine in 10 mL of THF over 20 minutes. After 10 minutes, the light yellow reaction mixture was diluted with pentane and washed once each with 10% sodium bisulfite solution, water and brine. The organic layer was dried (MgSO$_4$) and evaporated onto 5 g silica gel. Purification by flash chromatography (5 × 15 cm column) eluted with hexanes gave title iodide, 1.96 g (84%), as a colorless oil.

TLC Silica gel (hexanes) $R_f=0.68$.

$^1$H NMR (CDCl$_3$, 270 MHz): δ 7.24 (br s, 4H), 3.29 (t, 2H, J=6.5 Hz), 2.83 (t, 2H, J=7.0 Hz), 2.70 (t, 2H, J=7.0 Hz), 2.25 (quintet, 2H, J=7 Hz), 1.76 (sextet, 2H, J=7 Hz), 1.08 (t, 3H, J=7.0 Hz) ppm.

MS (CI-NH$_3$, +ion) m/e 289 (M+H).

F. [4-(4-Propylphenyl)butylidene]bisphosphonic acid, tetraethyl ester

To a stirred slurry of 480 mg (12.0 mmol) of 60% mineral oil dispersion of sodium hydride in 10 mL of DMF under argon at 0° C. was added, over 10 minutes, a solution of 3.50 g (12.1 mmol) of tetraethyl methylenediphosphonate. The ice bath was removed and the solution was stirred ar ambient temperature for 30 minutes. A solution of 1.15 g (3.99 mmol) of Part E iodide in 2 mL DMF was added to the resulting clear solution. After 15 hours, 0.71 mL (12.1 mmol) of acetic acid was added and the volatiles evaporated at 30° C. under vacuum. The resulting semi-solid residue was partitioned between ether and water. The aqueous layer was extracted once with ether and the organic layers combined and dried (MgSO$_4$). The crude product was purified by flash chromatography (5 × 20 cm column) eluted with 1:16 ethanol/ethyl acetate to give 1.30 g (73%) of title ester as a colorless oil.

TLC Silica gel (1:16 ethanol/ethyl acetate) $R_f=0.21$.

$^1$H NMR (CDCl$_3$, 270 MHz): δ 7.11 (br s, 4H), 4.13 (m, 8H), 2.54 (m, 4H), 2.29 (tt, 1H, J=24, 5.9 Hz), 1.90 (m, 4H), 1.60 (sextet, 2H, J=7.6 Hz), 1.31 (dt, 12H, J=1.8, 7 Hz), 0.93 (t, 3H, J=7.6 Hz) ppm.

G. [4-(4-Propylphenyl)butylidene]bisphosphonic acid

To a stirred solution of 1.18 g (2.63 mmol) of Part F ester in 10 mL of dichloromethane under argon at room temperature was added 2.2 mL (15.8 mmol) of bromotrimethylsilane. After 16 hours, the clear reaction mixture was evaporated ar 40° C. The residue was stirred in 20 mL of methanol at room temperature under argon for 1 hour. After evaporation at 50° C. the resulting solid residue was recrystallized from ethyl acetate to give 720 mg (81%) of title product as a white solid, mp 199.5°–201.5° C.

IR (KBr) 3422, 2957, 2930, 2870, 1514, 1464, 1236, 999, 934 cm$^{-1}$.

$^1$H NMR (DMSO-d$_6$, 270 MHz): δ 7.09 (d, 2H, J=8.2 Hz), 7.05 (d, 2H, J=8.2 Hz), 2.60 (t, 2H, J=7.3 Hz), 2.52 (t, 2H, J=7.6 Hz), 2.22 (tt, 1H, J=5.7, 23.4 Hz), 1.92 (m, 4H), 1.60 (sextet, 2H, J=7.3 Hz) ppm.

MS (FAB, +ions) m/e 354 (M+NH$_4$), 337 (M+H).

MICROANALYSIS Calc'd for C$_{13}$H$_{22}$O$_6$P$_2$: C, 46.43; H, 6.59; P, 18.42.

Found: C, 46.34; H, 6.52; P, 18.29.

EXAMPLE 20

(E)-[4-[4-(2-Methyl-1-propenyl)phenyl]-3-butenylidene]bisphosphonic acid, trisodium salt

A.

(E)-3-[4-(2-Methyl-1-propenyl)phenyl]-2-propen-1-ol

To a solution of 1.75 g (8.1 mmol) of Example 15, Part C ester in 10 mL of toluene under argon at −20° C. was added over 20 minutes, 17.0 mL (17.0 mmol) of a 1M solution of diisobutylaluminum in toluene. The resulting colorless solution was stirred for 1 hour and then quenched with 5 mL of 10% citric acid solution. The mixture was extracted with ether and the extract washed twice with saturated ammonium chloride solution, once with water and once with brine. The organic extract was dried (Na$_2$SO$_4$), filtered, and evaporated to give title alcohol as 1.38 g (90%) of a white solid, mp 62°–64° C.

TLC Silica gel (1:49 ether/dichloromethane) $R_f=0.29$.

IR (film) 3396, 2968, 2828, 1699, 1603, 1379, 1178, 1091 cm$^{-1}$.

$^1$H NMR (CDCl$_3$, 270 MHz): δ 7.32 (d, 2H, J=8.2 Hz), 7.17 (d, 2H, J=8.2 Hz), 6.58 (d, 1H, J=15.8 Hz), 6.32 (dt, 1H, J=15.8, 5.3 Hz), 6.24 (br s, 1H), 4.30 (d, 2H, J=5.3 Hz), 1.90 (s, 3H), 1.87 (s, 3H), 1.65 (s, 1H) ppm.

MS (CI-NH$_3$, −ions) m/e 187 (M-H).

Anal. Calc'd for C$_{13}$H$_{16}$O: C, 82.93; H, 8.57.

Found: C, 82.89; H, 8.84.

B.

(E)-1-(3-Chloro-1-propenyl)-4-(2-methyl-1-propenyl)-benzene

To a stirred solution of 1.03 g (7.71 mmol) of N-chlorosuccinimide in 15 mL dichloromethane at −30° C. under argon was added 0.63 mL (8.5 mmol) dimethylsulfide over 5 minutes. After an additional 10 minutes, the reaction was warmed to 0° C. for 10 minutes and then cooled to −40° C. A solution of 1.28 g (6.80 mmol) of Part A alcohol in 15 mL dichloromethane was then added at a rate such that the reaction temperature did not rise above −35° C. After the addition was complete, the reaction was warmed to 0° C. over 1 hour and then stirred for 1 hour at 0° C. The resulting cloudy solution was quenched with ice water and extracted twice with hexanes. The extracts were combined, washed with cold brine, dried (Na$_2$SO$_4$) and evaporated to obtain 1.38 g (98%) of title chloride as a light yellow solid, mp 48°–50° C.

IR (film) 2967, 2926, 1700, 1605, 1250, 969 cm$^{-1}$.

$^1$H NMR (CDCl$_3$, 270 MHz): δ 6.84 (m, 4H), 5.98 (d, 1H, J=7 Hz), 5.96 (br s, 1H), 5.71 (dt, 1H, J=15.8, 7 Hz), 3.46 (dd, 2H, J=7.0, 1.2 Hz), 1.44 (d, 3H, J=1.2 Hz), 1.42 (d, 3H, J=1.2 Hz) ppm.

MS (CI-NH$_3$, −ions) m/e 205 (M-H).

C. (E)-[4-[4-(2-Methyl-1-propenyl)phenyl]-3-butenylidene]bisphosphonic acid, tetraethyl ester To a stirred slurry of 700 mg (17.5 mmol) of sodium hydride (60% mineral oil dispersion) in 20 mL DMF under argon at 0° C. was added, over 10 minutes, a solution of 5.00 g (17.3 mmol) of tetraethyl methylenediphosphonate in 5 mL DMF. The ice bath was removed and the solution was stirred at ambient temperature for 30 minutes. A solution of 1.30 g (6.30 mmol) of Part B compound in 5 mL DMF was then added to the resulting clear solution. After 15 hours, 1.02 mL (17.5 mmol) of acetic acid was added and the volatiles evaporated at 40° C. under vacuum. The resulting residue was partitioned between ether and water. The aqueous layer was extracted twice with ether and the organic layers were combined and dried (MgSO$_4$). The crude product (2.65 g) was purified by flash chromatography (5×15 cm column) eluted with 1:15 ethanol/ethyl acetate to give 1.51 g (52%) of title ester as a colorless oil.

TLC Silica gel (1:9 ethanol/ethyl acetate) R$_f$=0.29.
IR (film) 2967, 2926, 1700, 1606, 1250, 968 cm$^{-1}$.
$^1$H NMR (CDCl$_3$, 270 MHz): δ 7.29 (d, 2H, J=8.2 Hz), 7.15 (d, 2H, J=8.2 Hz), 6.46 (d, 1H, J=15.8 Hz), 6.33 (dt, 1H, J=15.8, 6.5 Hz), 6.23 (br s, 1H), 4.19 (m, 8H), 2.85 (tt, 2H, J=6.5, 17 Hz), 2.46 (tt, 1H, J=6.5, 23.5 Hz), 1.90 (s, 3H), 1.87 (s, 3H), 1.33 (dt, 12H, J=1.8, 6.8 Hz) ppm.

D. (E)-[4-[4-(2-Methyl-1-propenyl)phenyl]-3-butenylidene]bisphosphonic acid, trisodium salt To a stirred solution of 960 mg (2.1 mmol) of Part C ester and 544 μL (4.1 mmol) 2,4,6-collidine in 9 mL of dichloromethane under argon at room temperature was added 1.24 mL (9.3 mmol, 6 equivalents) of bromotrimethylsilane. After 24 hours, the resulting clear solution was evaporated at 30° C. and the residue stirred for 1 hour with 14.5 mL (7.25 mmol) of 0.5M sodium hydroxide solution. The solution was lyophilized and then purified by MPLC (2.5×20 cm column of Mitsubishi Kasei Sepabeads SP207SS resin): 10.5 mL fractions, 7 mL/1 minute flow rate, eluted with water. Fractions 12-20 were collected, partially evaporated and lyophilized to give 595 mg (69%) of title compound as a flocculant white solid. After 24 days, HPLC of the product indicated that the compound had partially decomposed. The material was dissolved in 10 mL of water and brought to pH 12.2 with 1M sodium hydroxide and repurified by MPLC (2.5×20 cm column of Mitsubishi Kasei Sepadbeads SP207SS resin): 10.5 mL fractions, 7 mL/minute flow rate, eluted with water. The compound eluted in fractions 10-21. Fractions 15-20 were pooled, lyophilized and then precipitated from water/acetone to give 388 mg of title compound as a white, waxy solid.

IR (KBr) 3433, 2968, 1650, 1510, 1111 cm$^{-1}$.
$^1$H NMR (D$_2$O, 270 MHz): δ 7.38 (d, 2H, J=8.2 Hz), 7.21 (d, 2H, J=8.2 Hz), 6.47 (m, 2H), 6.24 (br s, 1H, 2.64 (septet, 2H, J=7 Hz), 1.8 (tt, 1H, J=7, 14 Hz), 1.83 (s, 3H), 1.81 (s, 3H) ppm.
MS (FAB, +ions) m/e 369 (M-2Na+3H), 391 (M-Na+2H), 413 (M+H), 435 (M+Na).
Anal. Calc'd for C$_{14}$H$_{17}$Na$_3$O$_6$P$_2$.3/2 H$_2$O: C, 38.28; H, 4.59; P, 14.10.
Found: C, 37.95; H, 4.55; P, 14.22.

EXAMPLE 21

[4-[4-(2-Methylpropyl)phenyl]butylidene]bisphosphonic acid, disodium salt

A. [4-[4-(2-Methylpropyl)phenyl]butylidene]bisphosphonic acid, tetraethyl ester A slurry of 0.5 g (8 mmol) of ammonium formate and 508 mg (1.1 mmol) of Example 20, Part C ester in 10 mL of ethanol was stirred under argon for 20 minutes and then 0.5 g of 10% palladium on carbon was added. Gas evolution commenced within 10 minutes. After 16 hours, the reaction mixture was filtered through Celite, the collected solids washed with dichloromethane and the filtrate evaporated. The resulting residue was dissolved in dichloromethane, filtered through sodium sulfate and re-evaporated. Purification by flash chromatography (2.5×10 cm column) eluted with 1:32 ethanol/ethyl acetate gave 400 mg (80%) of title ester as a colorless oil.

TLC silica gel (1:32 ethanol/ethyl acetate) R$_f$=0.31.
$^1$H NMR (CDCl$_3$, 270 MHz): δ 7.07 (d, 2H, J=5.9 Hz), 7.04 (d, 2H, J=5.9 Hz), 4.15 (m, 8H), 2.60 (t, 2H, J=7.6 Hz), 2.42 (d, 2H, J=7.0 Hz), 2.29 (tt, 1H, J=5.8, 24.0 Hz), 1.90 (m, 5H), 1.30 (m, 12H), 0.88 (dt, 6H, J=1.7 Hz) ppm.
MS (CI-NH$_3$, +ions) m/e 463 (M+H).

B. [4-[4-(2-Methylpropyl)phenyl]butylidene]bisphosphonic acid, disodium salt To a stirred solution of 395 mg (0.85 mmol) of Part A ester and 340 μL (2.6 mmol) of 2,4,6-collidine in 3.5 mL of dichloromethane under argon at room temperature was added 0.68 mL (5.1 mmol) of bromotrimethylsilane. After 22 hours, the resulting clear solution was evaporated at 25° C. and the residue stirred for 1 hour with 5.6 mL (2.8 mmol) of 0.5M sodium hydroxide solution. The solution was lyophilized and then purified by MPLC (2.5×20 cm column of Mitsubishi Kasei Sepadbeads SP207SS resin): 11.5 mL fractions, 7 mL/minute flow rate, eluted with 170 mL of water followed by a gradient prepared from 450 mL 2:1 isopropanol/water into 500 mL water. Fractions 35-48 were collected, partially evaporated and lyophilized to give 235 mg (66%) of title product as a flocculant white solid.

IR (KBr) 3422, 2954, 2869, 1514, 1465, 1168, 1086 cm$^{-1}$.
$^1$H NMR (D$_2$O, 270 MHz): δ 7.17 (d, 2H, J=7.9 Hz), 7.11 (d, 2H, J=7.9 Hz), 2.56 (t, 2H, J=5.3 Hz), 2.38. (d, 2H, J=7.0 Hz), 1.91 (tt, 1H, J=6.5, 21.7 Hz), 1.7 (m, 5H), 0.79 (d, 6H, J=8 Hz) ppm.
Anal. Calc'd for C$_{14}$H$_{22}$Na$_2$O$_6$P$_2$.5/4 H$_2$O: C, 40.35; H, 5.93; P, 14.86.
Found: C, 40.31; H, 6.03; P, 14.81.
MS (FAB, +ions) m/e 373 (M-Na+2H), 395 (M+H), 417 (M+Na), 439 (M+2Na-H).

EXAMPLE 22

[6-[4-(2-Methyl-1-propenyl)phenyl]hexylidene]bisphosphonic acid, trisodium salt

A. 5-[4-(2-Methyl-1-propenyl)phenyl]pentanoic acid, 1,1-dimethylethyl ester

In a flame-dried flask, to a stirred solution of 1.54 mL (11.0 mmol) of diisopropylamine in 20 mL of THF at −10° C. under argon, was added 4.4 mL (11 mmol) of 2.5M n-butyllithium in hexane at a rate to keep the temperature below +5° C. The resulting light yellow solution was stirred 10 minutes and then 4.0 mL of HMPA was added. After 20 minutes, the reaction was cooled to −72° C. and 1.62 mL (11.5 mmol) of t-butyl acetate was added over 5 minutes. The bright yellow solution was stirred 30 minutes and then a solution of 3.00 g (10.0 mmol) of Example 15, Part F iodide in 5 mL of THF was added over 10 minutes. The reaction was stirred and allowed to warm to room temperature in situ. After 24 hours, the reaction was quenched with saturated ammonium chloride solution and diluted with ether.

The organic phase was washed three times with water, once with sodium bicarbonate solution and once with saturated 10% sodium bisulfite solution, dried ($Na_2SO_4$) and evaporated. The crude product was purified by flash chromatography (5×20 cm column) eluted with 1:4 dichloromethane/hexanes to provide 2.46 g (85%) of title ester as a colorless oil.

TLC Silica gel (1:4 dichloromethane/hexane) $R_f$=0.25.

$^1$H NMR (CDCl$_3$, 270 MHz): δ 7.12 (m, 4H), 6.23 (br s, 1H), 2.60 (t, 2H, J=4.7 Hz), 2.23 (t, 2H, J=4.7 Hz), 1.88 (s, 3H), 1.85 (s, 3H), 1.63 (m, 4H), 1.43 (s, 9H) ppm.

MS (CI-NH$_3$, +ions) m/e 289 (M+H), 233 (M-C$_4$H$_8$).

B. 4-(2-Methyl-1-propenyl)benzenepentanol

To a stirred solution of 1.90 g (6.59 mmol) of Part A ester in 5 mL THF under argon at room temperature was added a solution of 7.0 mL (7.0 mmol) of 1M lithium aluminum hydride in THF over 1 minute. The cloudy solution was set to reflux for 15 hours. The reaction was then cooled, quenched with brine and extracted three times with ether. The extracts were combined, dried (MgSO$_4$) and evaporated onto 5 g of silica gel. Purification by flash chromatography (2.5×10 cm column) eluted with dichloromethane gave 1.28 g (89%) of title alcohol as a colorless oil.

TLC Silica gel (dichloromethane) $R_f$=0.26.

$^1$H NMR (CDCl$_3$, 270 MHz): δ 7.12 (d, 2H, J=2.3 Hz), 7.10 (d, 2H, J=2.3 Hz), 6.23 (br s, 1H), 3.61 (q, 2H, J=6.4 Hz), 2.59 (t, 2H, J=8.2 Hz), 1.88 (d, 3H, J=1.8 Hz), 1.85 (d, 3H, J=1.2 Hz), 1.60 (m, 5H), 1.42 (m, 2H) ppm.

MS (CI-NH$_3$, +ions) m/e 219 (M+H).

C. 1-(5-Iodopentyl)-4-(2-methyl-1-propenyl)benzene

To a stirred solution of 1.17 g (5.36 mmol) of Part B alcohol, 1.55 g (5.9 mmol) of triphenylphosphine and 783 mg (11.5 mmol) of imidazole in 25 mL of THF was added a solution of 1.37 g (5.4 mmol) of iodine in 10 mL of THF over 20 minutes. After 10 minutes, the light yellow reaction mixture was diluted with pentane and washed once each with 10% sodium bisulfite solution, water and brine. The organic layer was dried (MgSO$_4$) and evaporated onto 5 g silica gel. Purification by flash chromatography (5×15 cm column) eluted with pentane gave title iodide, 1.88 g (92%) as a colorless oil.

TLC Silica gel (1:1 hexanes/dichloromethane) $R_f$=0.79.

$^1$H NMR (CDCl$_3$ 270 MHz): δ 7.12 (d, 2H, J=2.3 Hz), 7.10 (d, 2H, J=2.3 Hz), 6.23 (br s, 1H), 3.16 (t, 2H, J=7.0 Hz), 2.58 (t, 2H, J=8.2 Hz), 1.88 (d, 3H, J=1.2 Hz), 1.85 (d, 3H, J=1.1 Hz), 1.81 (m, 2H), 1.63 (m, 2H), 1.43 (m, 2H) ppm.

D. [6-[4-(2-Methyl-1-propenyl)phenyl]hexylidene]bisphosphonic acid, tetraethyl ester To a stirred slurry of 580 mg (14.5 mmol) of a 60% mineral oil dispersion of sodium hydride in 20 mL of DMF under argon at 0° C. was added, over 10 minutes, a solution of 4.20 g (14.6 mmol) of tetraethyl methylenediphosphonate. The ice bath was removed and the solution was stirred at ambient temperature for 30 minutes. A solution of 1.60 g (4.87 mmol) of Part C compound in 5 mL DMF was then added to the resulting clear solution. After 15 hours, 0.85 mL (14.5 mmol) of acetic acid was added and the volatiles evaporated at 30° C. under vacuum. The resulting semi-solid residue was partitioned between ether and water. The aqueous layer was extracted once with ether and the organic layers combined and dried (MgSO$_4$). The crude product was purified by flash chromatography (5×20 cm column) eluted with 1:66 ethanol/ethyl acetate to give 1.96 g (82%) of title ester as a colorless oil.

TLC Silica gel (1:32 methanol/ethyl acetate) $R_f$=0.48.

$^1$H NMR (CDCl$_3$, 270 MHz): δ 7.11 (m, 4H), 6.23 (br s, 1H), 4.17 (m, 8H), 2.58 (t, 2H, J=7.6 Hz), 2.26 (tt, 1H, J=24, 3.9 Hz), 1.95 (m, 2H), 1.89 (s, 3H), 1.86 (s, 3H), 1.62 (m, 4H), 1.33 (t+m, 14H, J=7 Hz) ppm.

E. [6-[4-(2-Methyl-1-propenyl)phenyl]hexylidene]bisphosphonic acid, trisodium salt To a stirred solution of 0.98 g (2.00 mmol) of Part D ester and 0.80 mL (6.0 mmol) of 2,4,6-collidine in 9 mL of dichloromethane under argon at room temperature was added 1.60 mL (12.0 mmol) of bromotrimethylsilane. After 22 hours, the resulting clear solution was evaporated at 35° C. and the residue stirred for 1 hour with 14 mL 1 M sodium hydroxide. The solution was lyophilized and then purified by MPLC (2.5×20 cm column of Mitsubishi Kasei Sepabeads SP207SS resin): 10.5 mL fractions, 7 mL/minute flow rate, eluted with 160 mL water, then a gradient of 2:3 isopropanol:water (450 mL) into water (500 mL). Fractions 18-37 were combined, evaporated to ca. 10 mL volume and precipitated with acetone to give 385 mg (40%) of title product as a white, waxy solid.

$^1$H NMR (D$_2$O, 270 MHz): δ 7.19 (d, 2H, J=8.2 Hz), 7.15 (d, 2H, J=8.2 Hz), 6.26 (br s, 1H), 2.54 (t, 2H, J=7.6 Hz), 1.81 (s, 3H), 1.77 (s, 3H), 1.3-1.8 (m, 7H), 1.26 (m, 2H) ppm.

Anal. Calc'd for $C_{16}H_{23}O_6P_2 \cdot 1.87 H_2O$: C, 40.38; H, 5.66; P, 13.02

Found: C, 40.38, H, 5.55; P, 12.85.

MS (FAB, +ion) m/e 421 (M+2H-Na), 443 (M+H), 465 (M+Na), 487 (M+2Na-H).

EXAMPLE 23

[2-[4-(4-Methyl-3-pentenyl)phenyl]ethylidene]bisphosphonic acid, tripotassium salt

A. 4-(4-Methyl-3-pentenyl)benzoic acid, methyl ester

In a flame-dried flask, to a stirred solution of 11.8 mL (84.3 mmol) of diisopropylamine in 80 mL of THF at −10° C. under argon, was added 33.0 mL (82.5 mmol) of 2.5M n-butyllithium in hexane at a rate to keep the temperature below +5° C. The resulting light yellow solution was stirred 10 minutes and then a solution of 5.45 g (40.0 mmol) of p-methylbenzoic acid in 20 mL of THF was added over 15 minutes. The resulting deep red solution was stirred for 45 minutes and 4.61 mL (40.0 mmol) of 1-bromo-3-methyl-3-butene was then added over 5 minutes. Within 15 minutes, the solution had faded to a light yellow color. The reaction mixture was poured into 150 mL of ice cold 1M hydrochloric acid and extracted twice with ether. The ether extracts were combined, washed once with 1M hydrochloric acid and then extracted twice with 45 mL portions of 1M sodium hydroxide solution. The base extracts were combined, washed once with ether and then poured into 95 mL of 1M hydrochloric acid. A white solid formed which was extracted into dichloromethane. The organic extract was dried ($MgSO_4$) and evaporated to give 7.10 g of a white, waxy solid. The solid was dissolved in 30 mL of DMF under argon and 1.65 g (41.2 mmol) of NaH (60% mineral oil dispersion) was added in small portions. After 30 minutes, 3.1 mL (50.1 mmol) of iodomethane was added and the reaction was stirred at room temperature. After 24 hours, the reaction was quenched with water and extracted three times with hexanes. The extracts were combined, washed once with saturated sodium bicarbonate solution, once with 10% sodium thiosulfate solution, twice with water, once with brine, dried ($MgSO_4$) and evaporated. Distillation with a 10 cm Vigreau column at 0.25 mm Hg gave 3.68 g (42%) of title compound as a colorless oil, bp 105°–107° C.

TLC Silica gel (2:3 dichloromethane/hexanes) $R_f = 0.4$.

IR ($CHCl_3$ film) 3016, 2930, 1717, 1610, 1438, 1285, 1224, 1208 $cm^{-1}$.

$^1H$ NMR ($CDCl_3$, 270 MHz): δ 7.94 (d, 2H, J=8.2 Hz), 7.23 (d, 2H, J=8.4 Hz), 5.13 (br t, 1H, J=7.6 Hz), 3.89 (s, 3H), 2.68 (t, 2H, J=7.1 Hz), 2.30 (dt, 2H, J=7.6, 7.0 Hz), 1.67 (s, 3H), 1.53 (s, 3H) ppm.

MS (CI-$NH_3$, +ions) m/e 219 (M+H).

B. 1-(Hydroxymethyl)-4-(4-methyl-3-pentenyl)benzene

To a solution of 3.35 g (15.3 mmol) of Part A ester in 20 mL of THF at room temperature under argon was added a solution of 8.0 mL (8.0 mmol) of 1M lithium aluminum hydride in THF over 5 minutes. After 2 hours, the reaction mixture was quenched with 0.5 mL of saturated brine and partitioned between ether and 10% citric acid solution. The ether extract was dried ($MgSO_4$), filtered and evaporated. Purification by flash chromatography (5×15 cm column) using 2:3 ether/hexane as eluent gave 2.56 g (88%) of title alcohol as a colorless oil.

TLC Silica gel (2:3 ether/hexanes) $R_f = 0.21$.

IR ($CHCl_3$ film) 3300, 2920, 1514, 1442, 1373, 1206, 1011 $cm^{-1}$.

$^1H$ NMR ($CDCl_3$, 270 MHz): δ 7.20 (d, 2H, J=8.2 Hz), 7.13 (d, 2H, J=8.2 Hz), 5.15 (br t, 1H, J=7.0 Hz), 4.53 (d, 2H, J=5.2 Hz), 2.60 (t, 2H, J=7.3 Hz), 2.57 (d, 1H), 2.28 (q, J=7.6 Hz, 2H), 1.66 (d, 3H, J=1.2 Hz), 1.53 (s, 3H) ppm.

MS (CI, $NH_3$, +ions) m/e 208 (M+$NH_4$)

C. 1-(Bromomethyl)-4-(4-methyl-3-pentenyl)benzene

To a stirred solution of 2.49 g (13.0 mmol) of Part B alcohol and 3.75 g (14.3 mmol) of triphenylphosphine in 50 mL of dichloromethane under argon at −40° C. was added 2.56 g (14.3 mmol) of powdered N-bromosuccinimide in portions over 10 minutes. The reaction temperature was not allowed to rise over −35° C. After 1 hour, the reaction mixture was evaporated onto 5 g of silica gel. Purification by flash chromatography (5×15 cm column) using 1:3 dichloromethane/hexanes as the eluent, gave 3.03 (92%) of title bromide as a colorless oil.

TLC Silica gel (1:3 dichloromethane/hexanes) $R_f = 0.23$.

$^1H$ NMR ($CDCl_3$, 270 MHz): δ 7.27 (d, 2H, J=8.2 Hz), 7.14 (d, 2H, J=8.2 Hz), 5.15 (br t, 1H, J=7.2 Hz), 4.46 (s, 2H), 2.61 (t, 2H, J=7 Hz), 2.26 (q, 2H, J=7 Hz), 1.67 (d, 3H, J=1.1 Hz), 1.55 (s, 3H) ppm.

MS (CI-MH3, +ions) m/e 270, 272 (M+$NH_4$).

D. [2-[4-(4-Methyl-3-pentenyl)phenyl]ethylidene]bisphosphonic acid, tetraethyl ester To a stirred slurry of 480 mg (12.0 mmol) of 60% mineral oil dispersion of sodium hydride in 15 mL of DMF under argon at 0° C. was added, over 10 minutes, a solution of 3.50 g (12.1 mmol) of tetraethyl methylenediphosphonate in 5 mL of DMF. The ice bath was removed and the solution was stirred at ambient temperature for 30 minutes. A solution of 1.00 g (3.95 mmol) of Part C bromide in 2 mL DMF was then added to the resulting clear solution. After 24 hours, 0.70 mL (12 mmol) of acetic acid was added and the volatiles evaporated at 40° C. under vacuum. The resulting semi-solid residue was partitioned between ether and saturated sodium bicarbonate solution. The aqueous layer was extracted once with ether and the organic layers combined and dried ($MgSO_4$). The crude product was purified by flash chromatography (5×15 cm column) eluted with 1:21 ethanol/ethyl acetate to give 1.02 g (62%) of title ester as a yellow oil.

TLC Silica gel (1:21 ethanol/ethyl acetate) $R_f = 0.21$.

IR ($CH_2Cl_2$ film) 2982, 2930, 1445, 1242, 1026, 974, 823 $cm^{-1}$.

$^1H$ NMR ($CDCl_3$, 270 MHz): δ 7.18 (d, 2H, J=8.2 Hz), 7.10 (d, 2H, J=8.2 Hz), 5.15 (br t, 1H, J=7.0 Hz), 4.10 (m, 8H), 3.22 (dt, 2H, J=5.9, 16.4 Hz), 2.65 (tt, 1H, J=6.4, 24 Hz), 2.59 (t, 2H, J=7.7 Hz), 2.25 (m, 2H), 1.68 (s, 3H), 1.57 (s, 3H), 1.28 (dt, 12H, J=4.7, 7.0 Hz) ppm.

MS (CI-$NH_3$, +ions) m/e 461 (M+H).

E. [2-[4-(4-Methyl-3-pentenyl)phenyl]ethylidene]bisphosphonic acid, tripotassium salt To a stirred solution of 895 mg (1.94 mmol) of Part D ester and 0.85 mL (6.6 mmol) of 2,4,6-collidine in 10 mL of dichloromethane under argon at room temperature was added 1.7 mL (13 mmol) of bromotrimethylsilane. After 22 hours, the resulting clear solution was evaporated at 35° C. and the residue stirred for 1 hour with 15 mL 1M potassium hydroxide. The solution was lyophilized and then purified by MPLC (2.5×20 cm column of Mitsubishi Kasei Sepabeads CHP20P resin): 10.5 mL fractions, 8.8 mL/minute flow rate, eluted with water. Fractions 16–20 were collected and lyophilized to give title product as a white lyophilate, 465 mg (48%).

$^1H$ NMR ($D_2O$, 270 MHz): δ 7.19 (d, 2H, J=7.9 Hz), 7.06 (d, 2H, J=7.9 Hz), 5.09 (br t, 1H, J=6.7 Hz), 2.94 (dt, 2H, J=6.5, 15.8 Hz), 2.49 (t, 2H, J=7.5 Hz), 2.16 (dt, 2H, J=6.7, 7.5 Hz), 2.02 (tt, 2H, J=6.6, 21.4 Hz), 1.51 (s, 3H), 1.44 (s, 3H) ppm.

MS (FAB, +ions) m/e 463 (M+H), 425 (M+2H-K).

Anal. Calc'd for $C_{14}h_{19}K_3O_6P_2 \cdot 2 H_2O$: C, 33.72; H, 4.65; P, 12.42

Found: C, 33.62; H, 4.62; P, 12.78.

EXAMPLE 24

(E)-[2-[4-(2,6-Dimethyl-1,5-heptadienyl)phenyl]ethylidene]bisphosphonic acid, tripotassium salt

A.

(E)-[2-[4-(2,6-Dimethyl-1,5-heptadienyl)phenyl]ethylidene]bisphosphonic acid, tetraethyl ester To 195 mg (4.87 mmol) of 60% NaH in mineral oil under argon at 0° C. was added 3 mL of DMF followed by 1.25 mL (5.02 mmol) of tetraethyl methylenediphosphonate dropwise over 10 minutes with much gas evolution. The reaction was allowed to stir for 0.5 hours at 0° C. when 476 mg (1.62 mmol) of Example 12, Part B compound in 5 mL of DMF was added and the reaction was gradually allowed to warm to room temperature and stir overnight. The reaction was diluted with ether and quenched by the addition of saturated NH$_4$Cl solution. The organic layer was washed with water, brine, dried over MgSO$_4$ and evaporated to provide 984 mg of a pale yellow oil. Flash chromatography was performed on 100 g of silica gel packed, loaded and eluted with 2:98 CH$_3$OH/CH$_2$Cl$_2$ collecting 30 mL fractions. Fractions 61 to 105 were combined and evaporated to provide 481 mg (59%) of title ester as a clear colorless oil.

TLC Silica gel (5:95 CH$_3$OH/CH$_2$Cl$_2$) R$_f$=0.35.

IR (CCl$_4$) 2981, 2930, 1445, 1251, 1029, 973, 801 cm$^{-1}$.

1H NMR (270 MHz, CDCl$_3$): δ 7.21 (d, 2H, J=8 Hz), 7.13 (d, 2H, J=8 Hz), 6.22 (s, 1H), 5.15 (m, 1H), 4.10 (m, 8H total), 3.23 (td, 2H, J=16 and 6.4 Hz), 2.65 (tt, 1H, J=24 and 6.4 Hz), 2.17 (m, 4H), 1.84 (s, 3H), 1.70 (s, 3H), 1.63 (s, 3H), 1.26 (td, 12H, J=7 and 4.7 Hz) ppm.

MS (CI, +ions) m/e 518 (M+NH$_4$), 501 (M+H).

Anal. Calc'd for C$_{25}$H$_{42}$O$_6$P$_2$.0.50 H$_2$O: C, 58.93; H, 8.51; P, 12.16.

Found: C, 58.56; H, 8.22; P, 12.37.

B.

(E)-[2-[4-(2,6-Dimethyl-1,5-heptadienyl)phenyl]ethylidene]bisphosphonic acid, tripotassium salt To a stirred solution of 450 mg (0.90 mmol) of Part A ester in 7 mL of CH$_2$Cl$_2$ under argon at 0° C. was added 0.36 mL (2.69 mmol) of 2,4,6-collidine followed by 0.71 mL (5.39 mmol) of bromotrimethylsilane and the reaction was allowed to warm to room temperature and stir overnight. The solvent was evaporated and pumped at high vacuum for 1 hour. The remainder was dissolved in 5.4 mL (5.4 mmol) of 1M KOH, stirred for 1 hour, diluted with water and lyophilized to provide 934 mg of crude product. The crude material was purified by MPLC on a column of CHP20P (2.5 cm diameter×19 cm height) eluted with water (fractions 1 to 12) followed by a gradient created by the gradual addition of 500 mL of a 70:30 CH$_3$CN/H$_2$O to a reservoir of 450 mL of water. Approximately 10 mL fractions were collected. Fractions 28 to 33 were combined, the acetonitrile was evaporated at reduced pressure and the aqueous solution was lyophilized to provide 220 mg (49%) of title product in the form of a dense white lyophilate.

IR (KBr) 3433, 3190, 2967, 2924, 1644, 1510, 1445, 1131, 1108, 883 cm$^{-1}$.

$^1$H NMR (400 MHz, D$_2$O): δ 7.34 (d, 2H, J=8.2 Hz), 7.20 (d, 2H, J=8.2 Hz), 6.26 (s, 1H), 5.20 (m, 1H), 3.05 (td, 2H, J=16 and 6 Hz), 2.17 (m, 4H), 2.13 (tt, 1H, J=21 and 6 Hz), 1.83 (s, 3H), 1.64 (s, 3H), 1.59 (s, 3H) ppm.

MS (FAB, +ions) m/e 503 (M+H), 465 (M+2H-K), 427 (M+3H-2K).

Anal. Calc'd for C$_{17}$H$_{23}$O$_6$P$_2$K$_3$.1.81 H$_2$O (Effective MW=535.22): C, 38.15; H, 5.01; P, 11.57

Found: C, 38.15; H, 5.15; P, 11.67

EXAMPLES 25

(E)-[5-[4-(2,6-Dimethyl-1,5-heptadienyl)phenyl]pentylidene]bisphosphonic acid, tripotassium salt

A.

1-(Hydroxybutyl)-4-(2,6-dimethyl-1,5-heptadienyl)benzene

To a stirred solution of 700 mg (2.39 mmol) of Example 11, Part B bromide and 68 mg (0.477 mmol) of CuBr in 15 mL of THF under argon at −30° C. was added 9.5 mL (4.78 mmol) of 0.5M Grignard reagent (dichloro[μ-[1-hexanolato(2-)-C$^6$:O$^1$]]dimagnesium, prepared in Example 3, Part A) in THF over 10 minutes. The reaction was allowed to stir at −30° C. when after 2 hours it was diluted with ether and quenched by the addition of saturated NH$_4$Cl solution. The ether layer was washed with dilute aqueous ammonia, water, brine, dried over MgSO$_4$ and evaporated to provide 660 mg of a clear colorless oil. Flash chromatography was performed on 100 g of silica gel packed and loaded with 6:1 hexane/EtOAc and eluted with 5:1 hexane/EtOAc collecting 20 mL fractions. Fractions 37 to 63 were combined and evaporated to provide 475 mg (73%) of title compound as a clear colorless oil.

TLC Silica gel (4:1 hexane/EtOAc) R$_f$=0.16.

IR (CCl$_4$) 3341, 2931, 2859, 1606 1511, 1447, 1358, 1059, 861 cm$^{-1}$.

$^1$NMR (270 MHz, CDCl$_3$) δ 7.15 (d, 2H, J=8 Hz), 7.12 (d, 2H, J=8 Hz), 6.23 (s, 1H), 5.16 (m, 1H), 3.64 (t, 2H, J=6 Hz), 2.62 (t, 2H, J=7 Hz), 2.18 (m, 4H), 1.85 (d, 3H, J=1 Hz), 1.70 (s, 3H), 1.63 (s, 3H), 1.50–1.80 (m, 4H), 1.38 (br s, 1H) ppm.

MS (CI-NH$_3$, +ions) m/e 290 (M+NH$_4$), 273 (M+H).

Anal. Calc'd for C$_{19}$H$_{28}$O.0.50 H$_2$O: C, 81.09; H, 10.39.

Found: C, 81.27; H, 10.30.

B.

1-(4-Iodobutyl)-4-(2,6-dimethyl-1,5-heptadienyl)benzene

To a stirred solution of 620 mg (2.27 mmol) of Part A compound, 655 mg (2.49 mmol) of triphenylphosphine and 324 mg (4.77 mmol) of imidazole in 15 mL of THF under argon at room temperature was added 576 mg (2.27 mmol) of iodine in 15 mL of THF dropwise over 10 minutes. Upon addition of the iodine the solution color would change from clear to pale yellow and then quickly back to clear. Near the end of the addition the color remained pale yellow and the reaction was allowed to stir at room temperature for 15 minutes when it was diluted with ether and washed with saturated Na$_2$S$_2$O$_3$ solution, water, brine, dried over MgSO$_4$ and evaporated to provide an oily white solid. The crude material was purified by flash chromatography on 50 g of silica gel eluted with pentane collecting 50 mL fractions. Fractions 4 to 12 were combined and evaporated to provide 728 mg (84%) of title iodide as a clear colorless oil.

TLC Silica gel (4:1 hexane/EtOAc) R$_f$=0.68.

IR (CCl$_4$) 2928, 2854, 1650, 1511, 1447, 1206, 863 cm$^{-1}$:

$^1$H NMR (270 MHz, CDCl$_3$): δ 7.15 (d, 2H, J=6 Hz), 7.11 (d, 2H, J=6 Hz), 6.23 (s, 1H), 5.17 (m, 1H), 3.18 (t, 2H, J=7 Hz), 2.60 (t, 2H, J=7 Hz), 2.18 (m, 4H), 1.86 (s, 3H), 1.70 (s, 3H), 1.63 (s, 3H), 1.60–1.90 (m, 4H) ppm.

MS (CI-NH$_3$, +ions) m/e 400 (M+NH$_4$), 383 (M+H).

Anal. Calc'd for C$_{19}$H$_{27}$I: C, 59.69; H, 7.12; I, 33.19. Found: C, 59.79; H, 7.25; I, 33.21.

C.
(E)-[5-[4-(2,6-Dimethyl-1,5-heptadienyl)phenyl]pentylidene]bisphosphonic acid, tetraethyl ester To 314 mg (7.85 mmol) of 60% NaH in mineral oil under argon at 0° C. was added 5 mL of DMF followed by 2.01 mL (8.09 mmol) of tetraethyl methylenediphosphonate added neat dropwise over 15 minutes with much gas evolution. The reaction was allowed to warm to room temperature and stir for 0.5 hours when 728 mg (2.61 mmol) of Part B iodide in 5 mL of DMF was added and the reaction was allowed to stir at room temperature overnight. The reaction was diluted with ether and quenched by the addition of saturated NH$_4$Cl solution. The organic layer was washed with water, brine, dried over MgSO$_4$ and evaporated to provide 1.53 g of a pale yellow oil. Flash chromatography was performed on 150 g of silica gel packed, loaded and eluted with 2:98 methanol/dichloromethane collecting 40 mL fractions. Fractions 20 to 34 were combined and evaporated to provide 804 mg (57%) of title ester as a clear colorless oil.

TLC Silica gel (5:95 CH$_3$OH/CH$_2$Cl$_2$) R$_f$=0.23.

IR (CCl$_4$) 2980, 2930, 2859, 1653, 1444, 1251, 1026, 971, 836 cm$^{-1}$.

$^1$NMR (270 MHz, CDCl$_3$): δ 7.14 (d, 2H, J=8.8 Hz), 7.10 (d, 2H, J=8.2 Hz), 6.22 (s, 1H), 5.15 (m, 1H), 4.15 (m, 8H total), 2.60 (t, 2H, J=7 Hz), 2.26 (tt, 1H, J=24 and 6 Hz), 2.17 (m, 4H), 1.85 (d, 3H, J=1 Hz), 1.70 (s, 3H), 1.63 (s, 3H), 1.50–2.00 (m, 6H), 1.32 (t, 12H, J=7 Hz) ppm.

MS (CI-NH$_3$, +ions) m/e 560 (M+NH$_4$), 543 (M+H).

Anal. Calc'd for C$_{28}$H$_{48}$O$_6$P$_2$.0.74 H$_2$O: C, 60.49; H, 8.97; P, 11.14. Found: C, 60.49; H, 8.89; P, 11.40

D.
(E)-[5-[4-(2,6-Dimethyl-1,5-heptadienyl)phenyl]pentylidene]bisphosphonic acid, tripotassium salt To a stirred solution of 704 mg (1.29 mmol) of Part C ester in 10 mL of dichloromethane under argon at 0° C. was added 0.51 mL (3.86 mmol) of 2,4,6-collidine followed by 1.02 mL (7.74 mmol) of bromotrimethylsilane and the reaction was allowed to warm to room temperature and stir overnight. The solvent was evaporated and pumped at high vacuum for 1 hour. The remainder was dissolved in 7.7 mL (7.70 mmol) of 1M KOH solution, stirred for 1 hour, diluted with water and lyophilized. The crude material was purified by MPLC on a column of CHP20P (2.5 cm diameter×23 cm height) eluted with water (fractions 1 to 15) followed by a gradient created by the gradual addition of 500 mL of 70:30 CH$_3$CN/H$_2$O to a reservoir of 450 mL of water. Approximately 10 mL fractions were collected. Fractions 41 to 43 were combined, the acetonitrile was evaporated at reduced pressure and the aqueous solution was lyophilized to provide 336 mg (48%) of title product in the form of a dense white lyophilate.

IR (KBr) 3365, 2928, 2858, 1650, 1511, 1450, 1384, 1107, 966, 874 cm$^{-1}$.

$^1$H NMR (400 MHz, D$_2$O): δ 7.23 (d, 2H, J=8.2 Hz), 7.18 (d, 2H, J=8.2 Hz), 6.23 (s, 1H), 5.18 (m, 1H), 2.58 (t, 2H, J=6.45 Hz), 2.15 (m, 4H), 1.80 (s, 3H), 1.63 (s, 3H), 1.40–1.90 (m, 7H total), 1.57 (s, 3H) ppm.

MS (FAB, +ions) m/e 589 (M+K), 545 (M+H), 527 (M+H-H$_2$O), 487 (M+2H-K).

Anal. Calc'd for C$_{20}$H$_{29}$K$_3$O$_6$P$_2$.1.49 H$_2$O: C, 42.03; H, 5.64; P, 10.84.

Found: C, 42.03; H, 5.54; P, 10.58.

EXAMPLE 26
(Z)-(6,10-Dimethyl-5,9-undecadienylidene)bisphosphonic acid, tetrasodium salt

A. (Z)-8-Chloro-2,6-dimethyl-2,6-octadiene

To a stirred solution of 10.0 g (64.83 mmol) of (Z)-3,7-dimethyl-2,6-octadien-1-ol and 9.42 mL (71.31 mmol) of 2,4,6-collidine under argon at room temperature was added dropwise 2.74 g (64.83 mmol) of lithium chloride in 30 mL of DMF. The mixture was cooled to 0° C. and treated with 5.52 mL (71.31 mmol) of methanesulfonyl chloride dropwise over 10 minutes. The reaction was stirred at 0° C. for 4 hours (solid present), then was poured into 300 mL of ice/water. The aqueous solution was washed three times with 200 mL portions of hexane. The organic layers were combined and washed with 5% KHSO$_4$, water, saturated NaHCO$_3$, brine, dried (MgSO$_4$) and evaporated to provide 9.48 g (85%) of title chloride as a pale yellow oil.

TLC Silica gel (8:1 hexanes/ethyl acetate) R$_f$=0.44.

$^1$H NMR (270 MHz, CDCl$_3$): δ 5.45 (t, 1H, J=6.0 Hz), 5.11 (m, 1H), 4.08 (d, 2H, J=7.0 Hz), 2.11 (m, 4H), 1.77 (s, 3H), 1.69 (s, 3H), 1.62 (s, 3H) ppm.

B. (Z)-(3,7-Dimethyl-2,6-octadienyl)propanedioic acid, diethyl ester

To a stirred solution of 3.96 g (0.165 mol) of NaH in 100 mL of THF at 0° C. under argon was added dropwise 25.10 mL (0.165 mol) of diethyl malonate over 15 minutes. The solution was stirred for 0.5 hours at 0° C., at which time 9.50 g (0.055 mol) of Part A chloride in 50 mL of THF was added dropwise over 15 minutes. The reaction gradually warmed and was stirred for 18 hours at room temperature, then was diluted with ether and quenched with saturated NH$_4$Cl. The organic layer was washed with water, brine, dried (MgSO$_4$) and concentrated to provide a pale yellow oil. The excess diethyl malonate was distilled away (1.5 mm Hg, 75° C.) from the title diester providing 14.10 g (87%) of title ester as a colorless oil.

TLC Silica gel (9:1 hexanes/ethyl acetate) R$_f$=0.44.

$^1$H NMR (270 MHz, CDCl$_3$): δ 5.10 (m, 2H), 4.18 (q, 4H, J=7.0 Hz), 3.30 (t, 1H, J=7.6 Hz), 2.59 (t, 2H, J=7.6 Hz), 2.06 (m, 4H), 1.68 (s, 6H), 1.61 (s, 3H), 1.25 (t, 6H, J=7.0 Hz) ppm.

C. (Z)-5,9-Dimethyl-4,8-decadienoic acid, ethyl ester

A stirred solution of 14.10 g (47.60 mmol) of Part B diester, 1.0 mL (57.12 mmol) of water and 4.85 g (114.3 mmol) of lithium chloride in 50 mL of DMSO was heated to 190° C. for 3 hours. The reaction was cooled to room temperature and diluted with 500 mL of a 1:1 solution of hexane/ether, then washed with water, brine and dried (MgSO$_4$). The organic layer was concentrated to provide 6.40 g (28.6 mol) of title ester as a pale yellow oil.

TLC Silica gel (95:5 hexanes/ethyl acetate) $R_f=0.34$.

$^1$H NMR (270 MHz, CDCl$_3$): δ 5.11 (m, 2H), 4.12 (q, 2H, J=7.0 Hz), 2.30 (m, 2H), 2.05 (m, 2H), 1.68 (s, 6H), 1.61 (s, 3H), 1.25 (t, 3H, J=7.0 Hz) ppm.

MS (CI-NH$_3$, +ions) m/e 242 (M+NH$_4$), 225 (M+H).

D. (Z)-5,9-Dimethyl-4,8-decadien-1-ol

To a stirred solution of 1.10 g (28.60 mmol) of lithium aluminum hydride in 125.0 mL of ether at 0° C. under argon was added dropwise 6.40 g (28.60 mmol) of Part C ester in 35.0 mL of ether over 10 minutes. The mixture stirred for 1.5 hours and was quenched by the following: 1.10 mL of water, 1.10 mL of 15% NaOH and 3.30 mL of water. The resulting suspension was dried (MgSO$_4$) and filtered through a Celite cake. The filtrate was concentrated to provide 5.80 g of a yellow oil. The oil was purified by short path distillation (0.5 mm-Hg; 142°-145° C.) to provide 3.26 g (63% overall from Part A chloride) of title alcohol as a colorless oil.

TLC Silica gel (9:1 hexanes/ethyl acetate) $R_f=0.20$.

$^1$H NMR (270 MHz, CDCl$_3$): δ 5.12 (m, 2H), 3.64 (q, 2H, J=6.5 Hz), 2.05 (m, 6H), 1.70 (s, 3H), 1.69 (s, 3H), 1.61 (s, 3H), 1.60 (m, 2H) ppm.

E. Methanesulfonic acid, (Z)-(5,9-dimethyl-4,8-decadienyl) ester

To a stirred solution of 3.26 g (17.91 mmol) of Part D alcohol in 50 mL of dichloromethane at 0° C. under argon was added 3.25 mL (23.28 mmol) of triethylamine and 1.66 mL (21.49 mmol) of methanesulfonyl chloride. The reaction was stirred for 2 hours at which time it was diluted with ether and washed with 5% KHSO$_4$, saturated NaHCO$_3$ and brine. The organic layer was dried (MgSO$_4$) and evaporated to provide 4.20 g (91%) of sulfonate as a pale yellow oil.

TLC Silica gel (CH$_2$Cl$_2$) $R_f=0.63$.

$^1$H NMR (270 MHz, CDCl$_3$): δ 5.10 (m, 2H), 4.21 (t, 2H, J=6.5 Hz), 2.99 (s, 3H), 2.10 (q, 2H, J=7.6 Hz), 2.04 (m, 4H), 1.78 (quint, 2H, J=7.0 Hz), 1.70 (s, 3H), 1.68 (s, 3H), 1.61 (s, 3H) ppm.

F. (Z)-10-Iodo-2,6-dimethyl-2,6-decadiene

To a stirred solution of 4.20 g (16.15 mmol) of Part E sulfonate in 100 mL of acetone at room temperature under argon was added 9.68 g (64.60 mmol) of sodium iodide. The reaction mixture was refluxed for 3.5 hours at which time it was diluted with 200 mL of a 1:1 mixture of water/hexane. The organic layer was washed with saturated sodium sulfite, dried (MgSO$_4$) and evaporated to provide 4.43 g of a pale yellow oil. The residue obtained was purified by filtration through 50 g of silica gel, eluting with hexane. Pure product fractions were combined to provide 4.29 g (91%) of title iodide as a colorless oil.

TLC Silica gel (hexanes) $R_f=0.56$.

IR (CCl$_4$) 2961, 2924, 1647, 1447, 1376, 1209, 1164 cm$^{-1}$.

$^1$H NMR (270 MHz, CDCl$_3$): δ 5.09 (m, 2H), 3.18 (t, 2H, J=7.0 Hz), 2.10 (m, 6H), 1.85 (quint, 2H, J=7.3 Hz), 1.69 (s, 6H), 1.62 (s, 3H) ppm.

MS (CI-NH$_3$, +ions) m/e 310 (M+NH$_4$), 292 (M).

G. (Z)-(6,10-Dimethyl-5,9-undecadienylidene)bisphosphonic acid, tetraethyl ester To a stirred solution of 246 mg (10.26 mmol) of sodium hydride in 20 mL of DMF at 0° C. under argon was added 2.55 mL (10.26 mmol) of tetraethyl methylenediphosphonate dropwise over 20 minutes. After 0.5 hours, 1.0 g (3.42 mmol) of Part F iodide in 3.0 mL of DMF was added and the reaction was stirred for 18 hours. The reaction was diluted with ether and saturated NH$_4$Cl, the organic fraction was washed with water, brine, dried (MgSO$_4$) and evaporated to provide 1.40 g of a yellow oil. Flash chromatography was performed on 200 g of silica gel eluting with 49.5:49.5:1 acetone/ethyl acetate/methanol (2 liters) followed by 47.5:47.5:5 acetone/ethyl acetate/methanol (1 liter). Approximately 30 mL fractions were collected. Product fractions were combined and evaporated to provide 1.10 g (73%) of title ester as a pale yellow oil.

TLC Silica gel (95:5 dichloromethane/methanol) $R_f=0.22$.

IR (CCl$_4$) 2980, 2930, 1442, 1392, 1248, 1163, 1028, 968 cm$^{-1}$.

$^1$H NMR (270 MHz, CDCl$_3$): δ 5.11 (t, 2H, J=6.5 Hz), 4.18 (m, 8H), 2.27 (tt, 1H, J=6.0, 24.3 Hz), 2.20-1.80 (m, 8H), 1.68 (s, 6H), 1.61 (m+s, 5H total), 1.34 (t, 12H, J=7.0 Hz) ppm.

MS (CI-NH$_3$, +ions) m/e 470 (M+NH$_4$), 453 (M+H).

H. (Z)-(6,10-Dimethyl-5,9-undecadienylidene)bisphosphonic acid, tetrasodium salt To a stirred solution of 1.00 g (2.21 mmol) of Part G ester in 20 mL of dichloromethane at room temperature under argon was added 876 μL (6.63 mmol) of 2,4,6-collidine followed by 1.75 mL (13.27 mmol) of bromotrimethylsilane. The reaction was stirred at room temperature for 24 hours at which time the solvent was evaporated and the residue pumped (high vacuum) for 2 hours. The remainder was treated with 9.72 mL (9.72 mmol) of 1M NaOH and evaporated to dryness. The crude residue was precipitated by dissolving the sample in 5.0 mL of water, warming to 50° C., treating the solution with 5.0 mL of acetone and placing the mixture in an ice bath. The supernatant was decanted away from the gelatinous solid and the solid was washed with 10 mL of 4:1 acetone/water and allowed to stir for 10 minutes. This washing procedure was performed three times at which point the solid was filterable. In each of the washings the solid was triturated with a spatula in order to aid the purification and solidification. The filtered solids were washed with 20 mL of 4:1 acetone/water, 20 mL of acetone and pumped (high vacuum) for 18 hours to provide 710 mg (75%) of the tetrasodium salt which contained 3% of the E-isomer. Further purification was performed on SP207SS gel (2.5 cm diameter×28 cm height) eluted with water, collecting approximately 10 mL fractions. Fractions #27-32 were combined and lyophilized to provide 153 mg of a white amorphous lyophilate. The white lyophilate was precipitated by being dissolved in 5 mL of water, treated with 566 μL (0.566 mmol) of 1M NaOH, heated to 50° C., treated with 15 mL of acetone and being placed in an ice bath. The solid was filtered and washed with 3:1 acetone/water. This procedure was done three times. The solid had a final wash of acetone then was pumped on under high vacuum for 24 hours to provide 137 mg (22%) of title tetrasodium salt (essentially pure cis by HPLC) as a white solid. Fractions #33-60 were combined and lyophilized to provide 386 (43%) of trisodium salt of the title product (containing 2% E-isomer by HPLC) as a white amorphous lyophilate.

Data for title tetrasodium salt:
IR (KBr) 2963, 2926, 2859, 1636, 1447, 1105 cm$^{-1}$.
$^1$H NMR (400 MHz, D$_2$O): δ 5.26 (t, 1H, J=7.0 Hz), 5.16 (m, 1H), 2.06 (m, 6H), 1.70 (m, 3H), 1.64 (s, 3H), 1.63 (s, 3H), 1.58 (s, 3H), 1.50 (m, 2H) ppm.
MS (FAB, +ions) m/e 451 (M+Na), 429 (M+H), 407 (M+2H-Na).
Anal. Calc'd for C$_{13}$H$_{22}$P$_2$O$_6$Na$_4$.3.0 mol H$_2$O Effective MW=482.2 C, 32.38; H, 5.85; P, 12.85.
Found: C, 32.03; H, 5.38; P, 12.54.

EXAMPLE 27

(E,E)-[4-[4-(2,6-Dimethyl-1,5-heptadienyl)phenyl]-3-butenylidene]bisphosphonic acid, tripotassium salt A. (E)-4-(2,6-Dimethyl-1,5-heptadienyl) benzaldehyde To a stirred solution of 815 mg (3.54 mmol) of (E)-4-(2,6-dimethyl-1,5-heptadienyl)benzenemethanol (prepared in Example 11 Part A) and 622 mg (5.31 mmol) of 4-methylmorpholine N-oxide in 15 mL of dry CH$_2$Cl$_2$ under argon at room temperature containing 1.8 g of 4 Å molecular sieves was added 62 mg (5 mol %) of tetrapropylammonium perruthenate in 3 portions over a few minutes giving a vigorous reaction. The reaction was allowed to stir at room temperature for 0.5 hours when it was filtered through a pad of silica gel washing copiously with CH$_2$Cl$_2$. Evaporation provided 800 mg of a clear colorless oil. Flash chromatography was performed on 80 g of silica gel packed and loaded with 30:1 hexane/EtOAc and eluted with 25:1 hexane/EtOAc collecting 12 mL fractions. Fractions 36 to 53 were combined and evaporated to provide 574 mg (71%) of title compound in the form of a clear colorless oil.

TLC Silica gel (CH$_2$Cl$_2$) R$_f$=0.63.
IR (CCl$_4$) 2964, 2930, 2731, 1706, 1604, 1567, 1450, 1379, 1281 cm$^{-1}$.
$^1$H NMR (270 MHz, CDCl$_3$): δ 9.97 (s, 1H), 7.81 (d, 2H, J=8 Hz), 7.37 (d, 2H, J=8 Hz), 6.30 (s, 1H), 5.15 (m, 1H), 2.22 (m, 4H), 1.90 (s, 3H), 1.70 (s, 3H), 1.64 (s, 3H) ppm.
MS (CI-NH$_3$, +ions) m/e 246 (M+NH$_4$), 229 (M+H).

B.

(E,E)-3-[4-(2,6-Dimethyl-1,5-heptadienyl)phenyl]-2-propenoic acid, methyl ester

To 133 mg (3.33 mmol) of 60% NaH in mineral oil under argon at room temperature was added 25 mL of THF followed by 0.54 mL (3.33 mmol) of trimethyl phosphonoacetate resulting in an exothermic reaction. The thick mixture was warmed to 50° C. and stirred for 1 hour when 693 mg (3.03 mmol) of Part A aldehyde in 10 mL of THF was added dropwise over a 5 minute period resulting in a colorless solution which was allowed to stir at 50° C. overnight. The reaction was diluted with ether and washed with saturated NaHCO$_3$, saturated NaHSO$_3$, water, brine, dried over MgSO$_4$ and evaporated to provide 852 mg of a pale yellow oil. Flash chromatography was performed on 85 g of silica gel packed and loaded with 4:1 hexane/dichloromethane and eluted with 3:1 hexane/dichloromethane collecting 30 mL fractions. Fractions 35 to 82 were combined and evaporated to provide 739 mg (86%) of title compound as a clear colorless oil.

TLC Silica gel (3:1 hexane/dichloromethane) R$_f$=0.18.
IR (CCl$_4$) 2955, 1723, 1638, 1436, 1366, 1314, 1170 cm$^{-1}$.

$^1$H NMR (270 MHz, CDCl$_3$): δ 7.67 (d, 1H, J=15.8 Hz), 7.46 (d, 2H, J=8.2 Hz), 7.25 (d, 2H, J=8.2 Hz), 6.40 (d, 1H, J=15.8 Hz), 6.25 (s, 1H), 5.15 (m, 1H), 3.79 (s, 3H), 2.20 (m, 4H), 1.88 (s, 3H), 1.70 (s, 3H), 1.63 (s, 3H) ppm.
MS (CI-NH$_3$, +ions) m/e 302 (M+NH$_4$), 285 (M+H).
Anal. Calc'd for C$_{19}$H$_{24}$O$_2$.0.37 H$_2$O: C, 78.41; H, 8.57.
Found: C, 78.41; H, 8.40.

C.

(E,E)-3-[4-(2,6-Dimethyl-1,5-heptadienyl)phenyl]-2-propen-1-ol

To a stirred solution of 739 mg (2.59 mmol) of Part B ester in 7 mL of toluene under argon at −20° C. was added 5.46 mL (5.46 mmol) of 1M DIBAL-H in hexanes over 20 minutes resulting in a pale yellow solution. The reaction was allowed to stir at −20° C. for 40 minutes when it was quenched with 5 mL of 10% citric acid solution and diluted with ether. The ether layer was washed with saturated NH$_4$Cl solution, water, brine, dried over Na$_2$SO$_4$ and evaporated to provide 648 mg (97%) of a white solid. Flash chromatography was performed on 65 g of silica gel packed, loaded and eluted with dichloromethane collecting 40 mL fractions. Fractions 14 to 30 were combined and evaporated to provide 608 mg (91%) of title compound as a white solid, mp 35°-36° C.

TLC Silica gel (CH$_2$Cl$_2$) R$_f$=0.28.
IR (CCl$_4$) 3406, 2962, 2928, 2856, 1708, 1604, 1452, 1168 cm$^{-1}$.
$^1$H NMR (270 MHz, CDCl$_3$): δ 7.32 (d, 2H, J=8.2 Hz), 7.18 (d, 2H, J=8.2 Hz), 6.58 (d, 1H, J=15.8 Hz), 6.33 (dt, 1H, J=15.8 and 5.8 Hz), 6.23 (s, 1H), 5.16 (m, 1H), 4.29 (d, 2H, J=5.8 Hz), 2.18 (m, 4H), 1.87 (s, 3H), 1.70 (s, 3H), 1.63 (s, 3H) ppm.
MS (CI, +ions) m/e 255 (M.), 239 (M+H-H$_4$O).
Anal. Calc'd for C$_{18}$H$_{24}$O.0.20 H$_2$O: C, 83.16; H, 9.46.
Found: C, 83.16; H, 9.40.

D.

(E,E)-1-(3-Chloro-1-propenyl)-4-(2,6-dimethyl-1,5-heptadienyl)benzene

To a stirred solution of 593 mg (2.31 mmol) of N-chlorosuccinimide in 15 mL of CH$_2$Cl$_2$ under argon at −35° C. (internal temperature) was added 0.24 mL (3.23 mmol) of dimethyl sulfide over 10 minutes. The mixture was warmed to 0° C. for 15 minutes, then cooled again to −35° C. when 593 mg (2.31 mmol) of Part C alcohol in 15 mL of CH$_2$Cl$_2$ was added dropwise over 10 minutes. After addition the reaction was allowed to warm to 0° C. gradually over 2 hours. After 1 hour at 0° C. the reaction was quenched with ice cold water, diluted with 500 mL of hexane and washed with water, brine, dried over MgSO$_4$ and evaporated to provide 545 mg of title compound as a yellow oil which was used directly in the next reaction.

E.

(E,E)-[4-[4-(2,6-Dimethyl-1,5-heptadienyl)phenyl]-3-butenylidene]bisphosphonic acid, tetraethyl ester To 238 mg (5.95 mmol) of 60% NaH in mineral oil under argon at 0° C. was added 5 mL of DMF and 1.53 mL (6.14 mmol) of tetraethyl methylenediphosphonate was added neat over 15 minutes with much gas evolution. The reaction was allowed to warm to room temperature and stir for 0.5 hours and then cooled again to 0° C. when 545 mg (1.98 mmol) of Part D chloride in 10 mL of DMF was added. After addition the reaction was allowed to warm to room temperature and stir overnight. The reaction was diluted with ether and quenched by the addition of saturated NH₄Cl solution. The organic layer was washed with water, brine, dried over MgSO₄ and evaporated to provide 997 mg of a yellow oil. Flash chromatography was performed on 100 g of silica gel packed, loaded, and eluted with 2:98 CH₃OH/CH₂Cl₂ collected 30 mL fractions. Fractions 27 to 46 were combined and evaporated to provide 659 mg (54% overall from Part C alcohol) of title ester as pale yellow oil.

TLC Silica gel (5:95 CH₃OH/CH₂Cl₂) $R_f$=0.26.

IR (CCl₄) 2982, 2931, 1720, 1253, 1029, 971 cm⁻¹.

¹H NMR (270 MHz, CDCl₃): δ 7.29 (d, 2H, J=8.2 Hz), 7.17 (d, 2H, J=8.2 Hz), 6.46 (d, 1H, J=15.8 Hz), 6.33 (dt, J=15.8 and 6.5 Hz), 5.15 (m, 1H), 4.18 (m, 8H total), 2.87 (tt, 2H, J=17 and 6.5 Hz), 2.45 (tt, 1H, J=24 and 6.5 Hz), 2.19 (m, 4H), 1.87 (s, 3H), 1.70 (s, 3H), 1.63 (s, 3H), 1.33 (dt, 12H, J=1.5 and 7 Hz) ppm.

MS (CI, +ions) m/e 527 (M+H).

Anal. Calc'd for C₂₇H₄₄O₆P₂.0.56 H₂O: C, 60.42; H, 8.47; P, 11.54.

Found: C, 60.42; H, 8.37; P, 11.49.

F. (E,E)-[4-[4-(2,6-Dimethyl-1,5-heptadienyl)phenyl]-3-butenylidene]bisphosphonic acid, tripotassium salt To a stirred solution of 639 mg (1.21 mmol) of Part E ester in 10 mL of dichloromethane under argon at 0° C. was added 0.48 mL (3.64 mmol) of 2,4,6-collidine followed by 0.96 mL (7.26 mmol) of bromotrimethylsilane and the reaction was allowed to warm to room temperature and stir overnight. The solvent was evaporated and pumped at high vacuum for 1 hour. The remainder was dissolved in 7.3 mL (7.30 mmol) of 1M KOH, stirred for 1 hour, diluted with water and lyophilized to provide 964 mg of crude lyophilate. The crude material was purified by MPLC on a column of CHP20P (2.5 cm diameter×22 cm height) eluted with water (fractions 1 to 15) followed by a gradient created by the gradual addition of 500 mL of a 70:30 CH₃CN/H₂O to a reservoir of 450 mL of water. Approximately 10 mL fractions were collected. Fractions were combined, the acetonitrile was evaporated at reduced pressure and the aqueous solution was lyophilized to provide 220 mg (35%) of title product as a dense white lyophilate.

IR (KBr) 3417, 2967, 2918, 1647, 1508, 1447, 1114, 870 cm⁻¹.

¹H NMR (400 MHz, D₂O): δ 6 7.41 (d, 2H, J=8.2 Hz), 7.23 (d, 2H, J=8.2 Hz), 6.54 (dt, 1H, J=16 and 6.5 Hz), 6.47 (d, 1H, J=16 Hz), 6.25 (s, 1H), 5.20 (m, 1H), 2.60 (tt, 2H, J=6.5 and 15 Hz), 2.15 (m, 4H), 1.89 (tt, 1H, J=7 and 21 Hz), 1.83 (s, 3H), 1.64 (s, 3H), 1.58 (s, 3H) ppm.

MS (FAB, +ions) m/e 529 (M+H), 491 (M+2H-K), 452 (M+3H-2K).

Anal. Calc'd for C₁₉H₂₅K₃O₆P₂.1.05 H₂O: C, 41.68; H, 4.99; P, 11.31.

Found: C, 41.68; H, 4.96; P, 11.49.

EXAMPLES 28

(E)-(8,12-Dimethyl-7,11-tridecadienylidene)bisphosphonic acid, tetrasodium salt

A. (E)-7,11-Dimethyl-6,10-dodecadienoic acid, 1,1-dimethylethyl ester

To a stirred solution of 1.10 mL (7.71 mmol) of freshly distilled diisopropylamine in 7.0 mL of THF under argon at −78° C. was added 3.20 mL (5.14 mmol) of 1.6M n-butyllithium in hexanes to give a pale yellow solution. The solution was allowed to warm to 0° C. for 15 minutes then cooled again to −78° C., at which time 693 μL (5.14 mmol) of t-butylacetate (t-BuOAc) was added neat. After an additional 15 minutes at −78° C., 1.79 mL (10.28 mmol) of HMPA was added followed by the addition of 1.50 g (5.14 mmol) of Example 5, Part F iodide in 5 mL of THF dropwise over 5 minutes. The reaction was stirred at −78° C. for 2 hours at which time it was warmed to room temperature, diluted with 50 mL of ether and quenched with saturated NH₄Cl. The organic layer was washed with water, brine, dried (MgSO₄) and evaporated to provide 1.39 g of a pale yellow oil. Flash chromatography was performed on 100 g of silica gel eluting with hexane (1 L) and 9:1 hexane/EtOAc (1 L). Product fractions were combined and evaporated to provide 1.15 g (92%) of title compound as a pale yellow oil.

TLC Silica gel (9:1 hexane/ethyl acetate) $R_f$=0.70.

IR (CCl₄) 2976, 2928, 2857, 1732, 1454, 1368, 1155 cm⁻¹.

¹H NMR (270 MHz, CDCl₃): δ 5.20 (t, 1H, J=6.9 Hz), 5.18 (t, 1H, J=6.9 Hz), 2.30 (t, 2H, J=7.3 Hz), 2.14 (m, 2H), 2.08 (m, 4H), 1.77 (s, 3H), 1.69 (m+s, 8H), 1.53 (s, 9H), 1.47 (m, 2H) ppm.

MS (CI-NH₃) m/e 298 (M+NH₄), 281 (M+H).

B. (E)-7,11-Dimethyl-6,10-dodecadien-1-ol

To a stirred solution of 234 mg (6.16 mmol) of lithium aluminum hydride in 10 mL of ether at 0° C. under argon was added dropwise over 10 minutes 1.15 g (4.10 mmol) of Part A ester. The reaction was stirred for 1 hour at which time it was quenched by the following: 234 μL of water, 234 μL of 15% NaOH in water and 700 μL of water. The granular mixture was stirred and dried (Na₂SO₄) for 0.5 hours at which time the mixture was filtered through a celite cake and the cake was washed with ether followed by dichloromethane. The filtrate was evaporated to provide 834 mg of a colorless oil. Flash chromatography was performed on 100 g of silica gel eluting with 1:1 hexane/EtOAc (1 L). Pure product fractions were combined and evaporated to provide 824 mg (96%) of title alcohol as a colorless oil.

TLC Silica gel (9:1 hexane/ethyl acetate) $R_f$=0.15.

IR (CCl₄) 3300, 2928, 2856, 1450, 1377, 1151, 1107, 1055 cm⁻¹.

1H NMR (270 MHz, CDCl₃): δ 5.13 (t, 1H, J=7.0 Hz), 5.10 (t, 1H, J=7.0 Hz), 3.63 (t, 2H, J=6.5 Hz), 2.10 (m, 2H), 2.01 (m, 4H), 1.68 (s, 3H), 1.60 (s, 6H), 1.56 (m, 2H), 1.36 (m,4H) ppm.

MS (CI-NH₃) m/e 228 (M+NH₄)

C. (E)-12-Iodo-2,6-dimethyl-2,6-dodecadiene

To a stirred solution of 820 mg (3.90 mmol) of Part B alcohol in 8 mL of THF under argon at room temperature was added 3.07 g (11.71 mmol) of triphenylphosphine, 797 mg (11.71 mmol) of imidazole and 1.98 g (7.81 mmol) of iodine. After 1 hour, the brown solution was diluted with ether and washed with saturated sodium sulfite, brine, dried (MgSO$_4$) and evaporated. Flash chromatography was performed on 100 g of silica gel eluting with hexane. Pure product fractions were combined and evaporated to provide 913 mg (73%) of title iodide as a colorless oil.

TLC Silica gel (Hexane) R$_f$=0.46.

IR (CCl$_4$) 2922, 2853, 1449, 1383 cm$^{-1}$.

$^1$H NMR (270 MHz, CDCl$_3$): δ 5.22 (t, 1H, J=6.5 Hz), 5.19 (t, 1H, J=6.5 Hz), 3.29 (t, 2H, J=7.0 Hz), 2.14 (m, 2H), 2.09 (m, 4H), 1.93 (quint, 2H, J=7.0 Hz), 1.78 (s, 3H), 1.70 (s, 6H), 1.45 (m,4H) ppm.

MS (CI-NH$_3$) m/e 338 (M+NH$_4$), 320 (M).

D.
(E)-(8,12-Dimethyl-7,11-tridecadienylidene)bisphosphonic acid, tetraethyl ester To a stirred mixture of 113 mg (4.69 mmol) of sodium hydride in 10 mL of THF at 0° C. under argon was added dropwise over 5 minutes 1.17 mL (4.69 mmol) of tetraethyl methylenediphosphate in 5 mL of THF. The mixture was stirred at 0° C. for 0.5 hours at which time 500 mg (1.56 mmol) of Part C iodide in 5 mL of THF was added dropwise over 5 minutes. The reaction was stirred at 0° C. for 1 hour, resulting in a clear solution which was brought to room temperature for 18 hours. The reaction was diluted with ether and quenched with saturated NH$_4$Cl. The organic layer was washed with water, brine, dried (MgSO$_4$) and evaporated to provide 800 mg of a pale yellow oil. Flash chromatography was performed on 100 g of silica gel eluting with 49.5:49.5:1 acetone/EtOAc/methanol (2 L). Pure product fractions were combined and evaporated to provide 420 mg (56%) of title ester as a colorless oil.

TLC Silica gel (49.5:49.5:1 acetone/ethyl acetate/-methanol) R$_f$=0.67.

IR (CCl$_4$) 2980, 2930, 2859, 1456, 1250, 1028, 787, 762 cm$^{-1}$.

$^1$H NMR (270 MHz, CDCl$_3$): δ 5.10 (m, 2H), 4.17 (m, 8H), 2.27 (tt, 1H, J=5.9, 24.0 Hz), 2.10–1.80 (m, 8H), 1.68 (s, 3H), 1.60 (s, 3H), 1.59 (s+m, 5H), 1.34 (t +m, 16H, J=7.0 Hz) ppm.

MS (CI-NH$_3$) m/e 498 (M+NH$_4$), 481 (M+H).

E.
(E)-(8,12-Dimethyl-7,11-tridecadienylidene)bisphosphonic acid, tetrasodium salt To a stirred solution of 410 mg (0.854 mmol) of Part D ester in 10 mL of dichloromethane at room temperature under argon was added 339 μL (2.56 mmol) of 2,4,6-collidine followed by 676 μL (5.12 mmol) of bromotrimethylsilane. The reaction was stirred at room temperature for 18 hours, at which time the solvent was evaporated and the residue pumped under high vacuum for 1 hour. The remainder was treated with 3.76 mL (3.76 mmol) of 1M NaOH and lyophilized. The crude lyophilate was precipitated by dissolving the sample in 5 mL of water, warming to 50° C., treating the solution with 2 mL of acetone and placing the cloudy mixture in an ice bath. The precipitate was filtered and the solid was washed with 4:1 acetone/water, while being broken up with a spatula. This procedure was performed three times. The solids had a final wash of acetone and was pumped under high vacuum for 18 hours to provide 268 mg (69%) of title product as a white solid.

IR (KBr) 2924, 2855, 1636, 1451, 1096, 949 cm$^{-1}$.

$^1$H NMR (400 MHz, D$_2$O): δ 5.22 (t, 1H, J=7.0 Hz), 5.14 (t, 1H, J=7.0 Hz), 2.06 (m, 2H), 1.97 (m, 4H), 1.80–1.50 (m, 3H), 1.63 (s, 3H), 1.56 (s, 6H), 1.45 (m, 2H), 1.29 (m, 4H) ppm.

MS (FAB, +ions) m/e 479 (M+Na), 457 (M+H), 435 (M+2H-Na).

Anal. Cald'd for C$_{15}$H$_{26}$P$_2$O$_6$Na$_4$·1.33 mol H$_2$O: Effective MW=480.24. C, 37.52; H, 6.02; P, 12.90.

Found: C, 37.66; H, 6.41; P, 13.10.

EXAMPLE 29
(E)-(5,9-Dimethyl-4,8-decadienyl)bisphosphonic acid, trisodium salt

A. (E)-(E)-5,9-Dimethyl-4,8-decadienyl-1-yl bromide

To a solution of 3.00 g (16.5 mmol) of Example 5, Part D alcohol and 30 mL of THF at 0° C. was added 4.19 g (16.0 mmol) of triphenylphosphine in one portion, followed by 2.94 g (16.5 mmol) of N-bromosuccinimide. The reaction was allowed to stir for 2 hours at 0° C., at which point the volatiles were removed under reduced pressure leaving a semisolid residue. The residue was diluted with 250 mL of ethyl acetate, washed with water, dried (MgSO$_4$) and concentrated leaving the crude bromide. The remainder was purified by flash chromatography on 300 g of silica gel with hexanes to yield 2.00 g (50%) of title bromide as a pale yellow oil.

TLC Silica gel (hexanes) R$_f$=0.53.

$^1$H NMR (CDCl$_3$, 270 MHz): δ 5.10 (t, 2H, J=6.5 Hz), 3.39 (t, 2H, J=7.1 Hz), 2.10 (m, 6H), 1.90 (quint., 2H, J=7.0 Hz), 1.68 (s, 3H), 1.62 (s, 3H), 1.60 (s, 3H) ppm.

B. (E)-(5,9-Dimethyl-4,8-decadienyl)phosphonic acid, diethyl ester

A mixture of 1.50 g (6.12 mmol) of title bromide and 1.00 (6.13 mmol) of triethylphosphite was heated to 125° C. (external bath temperature) for 20 hours. The product was cooled to room temperature and purified by flash chromatography on 300 g of silica gel with 5:95 ethanol/ethyl acetate to yield 0.80 g (44%) of title compound as a pale yellow oil.

TLC Silica gel (10:90 ethanol/ethyl acetate) R$_f$=0.83.

IR (film) 2978, 2914, 1444, 1390, 1058, 1030, 960 cm$^{-1}$.

$^1$H NMR (CDCl$_3$, 270 MHz): δ 6 5.08 (t, 2H, J=6.5 Hz), 4.10 (m, 4H), 2.05 (m, 6H), 1.75 (m, 2H), 1.68 (s, 3H), 1.60 (s, 6H), 1.32 (t, 6H, 7.0 Hz) ppm.

MS (CI-NH$_3$, +ions) m/e 320 (M+NH$_4$), 303 (M+H).

C. (E)-(5,9-Dimethyl-4,8-decadienyl)bisphosphonic acid, tetraethyl ester

To a stirred solution of 0.80 g (2.65 mmol) of Part B compound and 10 mL of THF at −78° C. was added 2.45 mL (1.30M, 3.18 mmol) of sec-butyllithium dropwise over 3 minutes. After 0.3 hours at −78° C. the reaction mixture was quickly added (via cannula) to a mixture of 0.91 g (5.3 mmol) of diethyl chlorophosphate in 5 mL of THF at −78° C. The mixture was stirred at −78° C. for 0.5 hours and was warmed to −40° C. for 1 hour. The reaction was quenched with NH$_4$Cl solution, diluted with ethyl acetate and washed with aqueous solutions of NH$_4$Cl, NaHCO$_3$, and brine. The organic layer was dried (MgSO$_4$) and concentrated under reduced pressure. The residual oil was purified by flash chromatography on 50 g of silica gel eluted with 10:90 ethanol/ethyl acetate to provide 0.47 g (40%) of title ester as a colorless oil.

TLC Silica gel (1:9 ethanol/ethyl acetate) $R_f=0.50$.

IR (film) 2982, 2932, 1663, 1444, 1391, 1252, 1164, 1027, 1030, 969 cm$^{-1}$.

$^1$H NMR (CDCl$_3$, 270 MHz): δ 5.09 (t, 2H, J=6.5 Hz), 4.10 (m, 8H), 2.25 (m, 3H), 2.00 (m, 6H), 1.68 (s, 3H), 1.62 (s, 3H), 1.60 (s, 3H), 1.34 (t, 12H, J=7.0 Hz) ppm.

MS (CI-NH$_3$, +ions) m/e 456 (M+NH$_4$), 439 (M+H).

D. (E)-(5,9-Dimethyl-4,8-decadienyl)bisphosphonic acid, trisodium salt

To a stirred solution of 0.44 g (1.00 mmol) of Part C ester in 6.0 mL of dichloromethane at 0° C. was added 2.42 g (2.00 mmol) of 2,4,6-collidine followed by 0.76 g (5.00 mmol) of bromotrimethylsilane. The reaction was allowed to stir at room temperature for 13 hours when the solvent was evaporated and the semisolid residue pumped (~1 mm pressure) for 0.5 hours. The residue was dissolved in 4.40 mL of 1N NaOH solution (4.40 mmol), diluted with 15 mL of water and freeze dried. The crude white solids were purified by MPLC on a column of SP207SS gel (2.5 cm diam.×20 cm height) eluting with water (250 mL), followed by a gradient created by the gradual addition of 400 mL acetonitrile to a reservoir of 350 mL of water. Approximately 8 mL fractions were collected. The aqueous solution was filtered and lyophilized to provide 0.28 g (71%) of title product as a white lyophilate.

IR (KBr) 3402, 2966, 2924, 2858, 1450, 1161, 1089, 881 cm$^{-1}$.

$^1$H NMR (D$_2$O, 400 MHz): δ 5.20 (t, 1H, J=6.4 Hz), 5.15 (t, 1H, J=7.0 Hz), 2.18 (q, 2H, J=7.3 Hz), 2.10 (m, 2H), 1.98 (m, 2H), 1.80 (two m, 2H), 1.63 (s, 3H), 1.59 (s+m, 4H), 1.57 (s, 3H) ppm.

Mass Spec. (FAB, +ions) m/e 393 (M+H), 371 (M-Na+2H), 349 (M-2Na+3H).

Anal. Calc'd for C$_{12}$H$_{21}$O$_6$Na$_3$P$_2$+0.74 H$_2$O: C, 35.54; H, 5.59; P, 15.27.

Found: C, 35.54; H, 5.91; P, 15.42.

EXAMPLE 30

(E)-[4-[3-(2,6-Dimethyl-1,5-heptadienyl)phenyl]-butylidene]bisphosphonic acid, tripotassium salt

A.

(E)-3-(2,6-Dimethyl-1,5-heptadienyl)benzenemethanol (1) (E)-3-(2,6-Dimethyl-1,5-heptadienyl)benzoic acid, methyl ester To 12 mL of THF under argon at −78° C. was added 7.5 mL (12.8 mmol) of 1.7M t-butyllithium in pentane to give a yellow solution to which 1.34 g (5.35 mmol) of Example 11, Part A (2) iodide in 10 mL of THF was added dropwise over 10 minutes. After addition, the reaction was allowed to stir at −78° C. for 0.5 hours and then warm to 0° C. for 0.5 hours. Zinc chloride (873 mg, 6.41 mmol, fuse-dried under vacuum three times) in 10 mL of THF was added via cannula to give zinc intermediate as a pale yellow solution which was allowed to stir at 0° C. for 1 hour.

A 100 mL flask was charged with 308 mg (0.266 mmol, 5 mol %) of tetrakis(triphenylphosphine)palladium (0) and 1.0 g (3.82 mmol) of methyl 3-iodobenzoate in an argon filled glove bag. A volume of 7 mL of THF was added and the suspension was cooled to 0° C. when the zinc intermediate prepared above was added via cannula. The mixture was allowed to warm to room temperature and stir for 1 hour when it was diluted with ether and quenched by the addition of 1N HCl solution. The organic layer was washed with water, saturated NaHCO$_3$, brine, dried over MgSO$_4$ and evaporated to provide 1.35 g of an orange-yellow oily solid. Flash chromatography was performed on 140 g of silica gel packed with 5:1 hexane/toluene and eluted with 3:1 hexane/toluene collecting 50 mL fractions. Fractions 58 to 87 were combined and evaporated to provide 715 mg (72%) of title ester as a clear, colorless oil.

TLC Silica gel (9:1 hexane/EtOAc) $R_f=0.38$.

IR (CCl$_4$) 2969, 2914, 2855, 1726, 1437, 1290, 1209, 1107, 1084, 731 cm$^{-1}$.

$^1$H NMR (270 MHz, CDCl$_3$): δ 7.91 (s, 1H), 7.85 (td, 1H, J=7 Hz and 2 Hz), 7.38 (m, 2H), 6.28 (s, 1H), 5.16 (m, 1H), 3.91 (s, 3H), 2.21 (m, 4H), 1.86 (s, 3H), 1.71 (s, 3H), 1.64 (s, 3H) ppm.

MS (CI-NH$_3$, +ions) m/e 276 (M+NH$_4$), 259 (M+H).

Anal. Calc'd for C$_{17}$H$_{22}$O$_2$: C, 79.03; H, 8.58.

Found: C, 79.23; H, 8.56.

(2) (E)-3-(2,6-Dimethyl-1,5-heptadienyl)benzenemethanol

To a 154 mg (4.06 mmol) of lithium aluminum hydride under argon at 0° C. was added 10 mL of dry ether, and 700 mg (2.71 mmol) of Part (1) ester in 15 mL of dry ether was added dropwise over 5 minutes. The reaction was allowed to stir at 0° C. for 0.5 hours when it was quenched by the addition of 0.16 mL of H$_2$O, 0.16 mL of 15% NaOH and then with 0.49 mL of H$_2$O. After stirring for 0.5 hours, Na$_2$SO$_4$ was added and the slurry was allowed to stir for 1 hour before filtering through a pad of celite washing copiously with ether. Evaporation provided 612 mg of a crude oil. Flash chromatography was performed on 70 g of silica gel packed with 15:1 hexane/ethyl acetate and eluted with 9:1 hexane/ethyl acetate collecting 50 mL fractions. Fractions 28 to 41 were combined and evaporated to provide 568 mg (91%) of Part (2) alcohol as a clear, colorless oil.

TLC Silica gel (9:1 dichloromethane/ethyl acetate) $R_f=0.56$.

IR (CCl$_4$) 3615, 2969, 2914, 2878, 2857, 1603, 1483, 1443, 1377, 1167, 1018, 731 cm$^{-1}$.

$^1$H NMR (270 MHz, CDCl$_3$): δ 7.28 (t, 1H, J=7 Hz), 7.18 (m, 3H), 6.26 (s, 1H), 5.17 (m, 1H), 4.64 (d, 2H, J=5 Hz), 2.19 (m, 4H), 1.85 (s, 3H), 1.70 (s, 3H), 1.64 (s, 3H) ppm.

MS (CI-NH$_3$, +ions) m/e 248 (M+NH$_4$), 231 (M+H).

B.

(E)-1-(Bromomethyl)-3-(2,6-dimethyl-1,5-heptadienyl)-benzene

To a stirred solution of 997 mg (4.33 mmol) of Part A alcohol in 35 mL of CH$_2$Cl$_2$ at −30° C. was added 1.36 g (5.19 mmol) of triphenylphosphine followed by 847 mg (4.76 mmol) of N-bromosuccinimide and the reaction was allowed to stir for 1 hour. The solution was concentrated to about 5 mL and was loaded onto a column of 125 g of silica gel which was eluted with hexane to provide 1.07 g (86%) of a clear colorless oil.

TLC Silica gel (9:1 hexane/EtOAc) $R_f=0.6$.

$^1$H NMR (270 MHz, CDCl$_3$): δ 7.24 (m, 4H), 6.24 (s, 1H), 5.16 (m, 1H), 4.47 (s, 2H), 2.18 (m, 4H), 1.85 (s, 3H), 1.71 (s, 3H), 1.64 (s, 3H) ppm.

C.

(E)-3-(2,6-Dimethyl-1,5-heptadienyl)benzenepropanoic acid, 1,1-dimethylethyl ester To a stirred solution of 0.44 mL (3.12 mmol) of diisopropylamine in 4 mL of THF was added 1.3 mL (2.08 mmol) of 1.6M butyllithium in hexanes to give a pale yellow solution. The solution was warmed to 0° C. for 15 minutes and then cooled to −78° C. when 0.28 mL (2.08 mmol) of t-butyl acetate was added neat over 10 minutes. After 15 minutes, 0.74 mL (4.26 mmol) of HMPA was added and then 600 mg (2.08 mmol) of Part B bromide was added in 5 mL of THF over 5 minutes. After 1 hour at −78° C., the reaction was diluted with ether and quenched with saturated $NH_4Cl$. The organic layer was washed with water and brine, dried ($MgSO_4$) and evaporated to provide 658 mg of a clear oil. The crude product was purified on 55 g of silica gel eluted with 1:99 EtOAc/hexane to give 478 mg (70%) of title compound as a colorless oil.

TLC Silica gel (9:1 hexane/EtOAc) $R_f=0.47$.

$^1$H NMR (270 MHz, $CDCl_3$): δ 6 7.22 (t, 1H, J=7 Hz), 7.06 (m, 3H), 6.24 (s, 1H), 5.15 (m, 1H), 2.86 (t, 2H, J=7 Hz), 2.53 (t, 2H, J=7 Hz), 2.18 (m, 4H), 1.85 (s, 3H), 1.71 (s, 3H), 1.64 (s, 3H), 1.42 (t, 9H) ppm.

D.

(E)-3-(2,6-Dimethyl-1,5-heptadienyl)benzenepropanol

To a suspension of 83 mg (2.18 mmol) of LAH in 10 mL of ether at 0° C. under argon was added 478 mg (1.45 mmol) of Part C ester in 25 mL of ether over 5 minutes. After 0.5 hours at 0° C., the reaction was carefully quenched by the sequential addition of 0.1 mL of water, 0.1 mL of 15% NaOH, and 0.26 mL of water. The mixture was stirred for 0.5 hours, $Na_2SO_4$ was added and after an additional 1 hour of stirring, the solids were removed by filtration through Celite. The solids were washed with ether, the filtrate was evaporated and the residue was purified by flash chromatography on 40 g of silica gel eluted with $CH_2Cl_2$ to provide 321 mg (86%) of title alcohol as a white solid.

$^1$H NMR (270 MHz, $CDCl_3$): δ 7.23 (t, 1H, J=8 Hz), 7.06 (m, 3H), 6.25 (s, 1H), 5.17 (m, 1H), 3.67 (t, 2H, J=6.5 Hz), 2.69 (t, 2H, J=7.5 Hz), 2.18 (m, 4H), 1.87 (m, 2H), 1.85 (d, 3H, J=1.8 Hz), 1.71 (s, 3H), 1.58 (s, 3H) ppm.

E.

(E)-1-(2,6-Dimethyl-1,5-heptadienyl)-3-(3-iodopropyl)benzene

To a stirred solution of 321 mg (1.24 mmol) of Part D alcohol, 359 mg (1.37 mmol) of triphenylphosphine and 177 mg (2.60 mmol) of imidazole in 30 mL of dry THF under argon at room temperature was added 346 mg (1.37 mmol) of iodine in 10 mL of THF dropwise over 40 minutes. After 1 hour, the reaction was diluted with ether and washed with water, saturated $Na_2S_2O_3$ and brine, dried ($MgSO_4$) and evaporated to provide an oily, white solid. Flash chromatography on 60 g of silica gel eluted with $CH_2Cl_2$ provided 402 mg (88%) of title iodide as a white solid.

$^1$H NMR (270 MHz, $CDCl_3$): δ 7.23 (t, 1H, J=8 Hz), 7.06 (m, 3H), 6.25 (s, 1H), 5.17 (m, 1H), 3.15 (t, 2H, J=7 Hz), 2.71 (t, 2H, J=7 Hz), 2.19 (m, 4H), 2.12 (quint, 2H, J=7 Hz), 1.87 (d, 3H, J=1.2 Hz), 1.71 (s, 3H), 1.64 (s, 3H) ppm.

F.

(E)-[4-[3-(2,6-Dimethyl-1,5-heptadienyl)phenyl]-butylidene]bisphosphonic acid, tetraethyl ester To a suspension of 131 mg (3.27 mmol) of 60% NaH in mineral oil in 3 mL of DMF was added 0.84 mL (3.37 mmol) of tetraethyl methylenediphosphonate neat over 10 minutes with much gas evolution. After 30 minutes at room temperature, the mixture was cooled to 0° C. and 402 mg (1.09 mmol) of Part E iodide in 5 mL of DMF was added. The reaction was allowed to warm to room temperature and stir for 24 hours. THe mixture was diluted with ether, quenched with saturated $NH_4Cl$, and the organic layer was washed with water and brine, dried ($MgSO_4$) and evaporated to provide 628 mg of a yellow oil. Flash chromatography on 65 g of silica gel eluted with 2:98 $CH_3OH/CH_2Cl_2$ provided 422 mg (73%) of title ester as a colorless oil.

TLC Silica gel (5:95 $CH_3OH/CH_2Cl_2$) $R_f=0.35$.

$^1$H NMR (270 MHz, $CDCl_3$): δ 7.22 (t, 1H, J=7.5 Hz), 7.04 (m, 3H), 6.24 (s, 1H), 5.16 (m, 1H), 4.16 (m, 8H), 2.62 (t, 2H, J=7 Hz), 2.29 (tt, 1H, J=6 and 24 Hz), 2.18 (m, 4H), 1.94 (m, 4H), 1.86 (d, 3H, J=1.2 Hz), 1.71 (s, 3H), 1.64 (s, 3H), 1.32 (t, 12H, J=7 Hz) ppm.

G.

(E)-[4-[3-(2,6-Dimethyl-1,5-heptadienyl)phenyl]-butylidene]bisphosphonic acid, tripotassium salt To a stirred, solution of 422 mg (0.798 mmol) of Part F ester in 6 mL of $CH_2Cl_2$ under argon at room temperature was added 0.32 mL (2.39 mmol) of 2,4,6-collidine followed by 0.63 mL (4.75 mmol) of TMSBr. The reaction was allowed to stir at room temperature for 24 hours. The solvent was evaporated and traces of volatiles were pumped off at high vacuum for 1 hour. The remainder was dissolved in 4.7 mL of 1M KOH, stirred for 1 hour, further diluted with water and lyophilized. The crude material was purified by MPLC on a column of CHP20P (2.5 cm diameter×21 cm height) eluted with water (fraction 1–15) followed by a gradient created by the gradual addition of 500 mL of 70:30 acetonitrile/water to a reservoir of 450 mL of water. Fractions 41–44 were combined, the $CH_3CN$ was evaporated at reduced pressure and the aqueous solution was lyophilized to provide 230 mg (54%) of title salt as a dense white lyophilate.

IR (KBr) 3090, 2965, 2924, 2854, 1599, 1447, 1375, 1111 cm$^{-1}$.

$^1$H NMR (400 MHz, $D_2O$): δ 7.28 (t, 1H, J=7.7 Hz), 7.18 (s, 1H), 7.11 and 7.15 (two d, 1H each, J=7.7 Hz), 6.27 (s, 1H), 5.21 (m, 1H), 2.62 (t, 2H, J=7 Hz), 2.18 (m, 4H), 1.82 (s, 3H), 1.65 (s, 3H), 1.59 (s, 3H), 1.50–1.90 (m, 5H) ppm.

MS (FAB, +ions) m/z 569 (M+K), 531 (M+H), 493 (M+2H-K).

Anal. Calc'd for 2.56 equiv $H_2O$: C, 50.92; H, 5.54; P, 16.41.

Found: C, 50.92; H, 5.50; P, 16.50.

EXAMPLE 31

(E)-(7,11-Dimethyl-6,10-dodecadienylidene)bisphosphonic acid, tetrasodium salt To a stirred solution of 4.50 g (9.65 mmol) of Example 13, Part B tetraethyl ester in 30 mL of dichloromethane at 0° C. was added 2.33 g (19.30 mmol) of 2,4,6-collidine followed by 8.85 g (57.90 mmol) of bromotrimethylsilane. The reaction was allowed to stir at room temperature for 14 hours when the solvent was evaporated and the semisolid residue pumped (~1 mm pressure) for 0.5 hours. The residue was dissolved by adding 49.0 mL of 1M NaOH solution (49.0 mmol) then diluting with 15 mL of water. The solution was freeze dried to provide an off white solid. The solid was purified by precipitation as follows.

(1) The solid was dissolved in 28 mL of water, warmed to 60° C., then precipitated out of the alkaline solution by adding 10 mL of acetone and cooling to 0° C. for 30 minutes.

(2) The mother liquor was decanted away from the gelatinous solid, the solids were washed with 25 mL of 3:1 acetone/water and the mixture stirred for 10 minutes. This washing procedure was performed three times. In each of the washings the gelatinous solid was broken up and "mashed" with a glass rod in order to aid the washing.

(3) The solids were washed with 30 mL of 5:1 acetone/water and finally acetone. At this point, the white solids were filtered and pumped for 18 hours to provide 4.0 g (90%) of title salt as a fine powder.

IR (KBr) 3433, 2966, 2926, 2856, 1635, 1450, 1095, 950 cm$^{-1}$.

$^1$H NMR (D$_2$O, 400 MHz): δ 5.16 (t, 1H, J=6.2 Hz), 5.06 (t, 1H, J=7.0 Hz), 2.00 (m, 2H), 1.95 (m, 4H), 1.60 (m, 3H), 1.53 (s, 3H), 1.48 (s, 6H), 1.40 (m, 2H), 1.28 (m, 2H) ppm.

Mass. Spec. (FAB, +ions) m/e 465 (M+Na), 443 (M+H), 421 (M-Na+2H), 403 (M-Na-H$_2$O+2H).

Anal. Calc'd for C$_{14}$H$_{24}$O$_6$Na$_4$P$_2$+1.85 H$_2$O: C, 35.36; H, 5.87; P, 13.03.

Found: C, 35.23; H, 5.78; P, 13.30.

EXAMPLE 32

(R)-(6,10-Dimethyl-9-undecenylidene)bisphosphonic acid, tetrasodium salt

A. (S)-8-Iodo-2,6-dimethyl-2-octene

A solution of 3.12 g (20.0 mmol) of (S)-(−)-β-citronellol (purchased from Aldrich Chem. Co.) and 2.72 g (40.0 mmol) of imidazole in 50 mL of THF at 0° C. was treated with 5.0 g (19.5 mmol) of triphenylphosphine followed by 4.83 g (19.0 mmol) of I$_2$ in 25 mL of THF dropwise over 20 minutes. The reaction mixture was stirred for 1.0 hour and was diluted with hexane. The organic mixture was washed with aqueous Na$_2$SO$_3$, brine, dried (Na$_2$SO$_4$) and evaporated to provide a crude white slurry. The slurry was purified by flash chromatography (300 g of silica gel) eluting with hexane to provide 4.00 g (79%) of title iodide as a colorless oil.

TLC Silica gel (hexane) R$_f$=0.66.

IR (neat) 2964, 2924, 2870, 1450, 1377, 1219, 1178 cm$^{-1}$.

$^1$H NMR (CDCl$_3$, 270 MHz): δ 5.10 (t, 1H, J=6.9 Hz), 3.20 (m, 2H), 1.90 (m, 3H), 1.65 (s+m, 4H), 1.60 (s, 3H), 1.55 (m, 1H), 1.35 (m, 1H), 1.20 (m, 1H), 0.90 (d, 3H, J=6.0 Hz) ppm.

Mass Spec (CI-NH$_3$, +ions) m/e 284 (M+NH$_4$), 267 (M+H).

B. (R)-5,9-Dimethyl-8-decen-1-ol

A 0.50M solution of lithium diisopropylamide in 30 mL THF (15.0 mmol) at −78° C. was treated with 2.00 mL of HMPA followed by 1.56 g (13.45 mmol) of t-butyl acetate. The mixture was stirred at −78° C. for 0.5 hours when 3.00 g (11.27 mmol) of Part A iodide was added in one portion. The reaction mixture was stirred for 1.0 hour at −78° C. when it was quenched with saturated aqueous NH$_4$Cl solution and diluted with ether. The organic fraction was washed with brine, dried (MgSO$_4$) and evaporated to provide a crude colorless oil. The oil was filtered through 80 g of silica gel eluting with 5:95 ethyl acetate/hexane to provide crude ester as a colorless oil.

TLC Silica gel (hexane) R$_f$=0.16.

To a suspension of 700 mg (18.4 mmol) of LAH in 100 mL of ether at −20° C. under argon was added 2.70 g (~10.6 mmol) of the crude ester to give a light yellow suspension. The reaction was allowed to warm to room temperature and stir for 1 hour when it was quenched by the sequential addition of: 1) 0.70 mL of water in 10 mL of THF 2) 2.1 mL of 15% NaOH and 3) 0.7 mL of water. The mixture was diluted with ether and stirred for 1 hour with 10 g of Na$_2$SO$_4$. The resulting granular suspension was filtered through a cake of celite and the filtrate evaporated to provide a colorless oil. The residue was purified by flash chromatography performed on 100 g of silica gel eluted with 1:4 ethyl acetate/hexane collecting in 20 mL fractions to provide 1.35 g (66%) of title compound as a colorless oil.

TLC Silica gel (3:7 ethyl acetate/hexane) R$_f$=0.57.

IR (film) 3348, 2974, 2930, 2860, 1635, 1456, 1377, 1072, 1055 cm$^{-1}$.

$^1$H NMR (CDCl$_3$, 270 MHz): δ 5.10 (t, 1H, J=7.0 Hz), 3.65 (q, 2H, J=4.1 Hz), 1.98 (m, 2H), 1.68 (s, 3H), 1.60 (s, 3H), 1.45, 1.35, 1.10 (3 m, 9H), 0.90 (d, 3H, J=6.5 Hz) ppm.

Mass Spec (CI-NH$_3$, +ions) m/e 202 (M+NH$_4$).

C. (R)-10-Iodo-2,6-dimethyl-2-decene

A solution of 1.00 g (5.43 mmol) of Part B alcohol and 0.74 g (10.86 mmol) of imidazole in 10 mL of THF at 0° C. was treated with 1.38 g (5.30 mmol) of triphenylphosphine followed by 1.40 g (5.50 mmol) of I$_2$ in 8 mL of THF dropwise over 20 minutes. The reaction mixture was stirred for 1.0 hour and was diluted with ether and aqueous Na$_2$SO$_3$ solution. The organic fraction was washed with brine, dried (Na$_2$SO$_4$) and evaporated to provide a crude white slurry. The slurry was purified by flash chromatography (100 g of silica gel) eluting with hexane to provide 0.90 g (56%) of title iodide as a colorless oil.

TLC Silica gel (hexane) R$_f$=0.75.

IR (film) 2958, 2926, 2854, 1640, 1454, 1377, 1217, 1170 cm$^{-1}$.

$^1$H NMR (CDCl$_3$, 270 MHz): δ 5.10 (t, 1H, J=7.5 Hz), 3.30 (t, 2H, J=7.5 Hz), 2.10 (m, 2H), 1.90 (quint., 2H, J=7.2 Hz), 1.80 (s, 3H), 1.70 (s, 3H), 1.45 (m, 5H), 1.35 (m, 2H), 0.95 (d, 3H, J=6.5 Hz) ppm.

Mass Spec (CI-NH$_3$, +ions) m/e 312 (M+NH$_4$), 294 (M).

D.

(R)-(6,10-Dimethyl-9-undecenylidene)bisphosphonic acid, tetraethyl ester

To a suspension of 195 mg (8.16 mmol) of NaH in 8 mL of dry DMF at 0° C. under argon was added 2.35 g (8.16 mmol) of tetraethyl methylenediphosphonate over 15 minutes to give a yellow solution. The reaction was allowed to warm to room temperature and stir for 0.5 hours when 0.80 g (2.70 mmol) of Part C iodide was added in one portion. The reaction mixture was stirred for 18 hours when it was quenched with saturated aqueous NH$_4$Cl solution and diluted with ethyl acetate. The organic fraction was washed with water, brine, dried (Na₂SO₄) and evaporated to provide a crude yellow oil. Flash chromatography was performed on 100 g of silica gel eluted with 1:9 ethanol/ethyl acetate collecting in 20 mL fractions to provide 1.00 g (81%) of title ester as a pale yellow oil.

TLC Silica gel (1:9 ethanol/ethyl acetate) $R_f=0.33$.

IR (film) 2978, 2928, 2866, 1645, 1250, 1163, 1026, 968 cm$^{-1}$.

$^1$H NMR (CDCl₃,270 MHz): δ 5.30 (t, 1H, J=6.9 Hz), 4.15 (m, 8H), 2.27 (tt, 1H, J=24.0, 5.9 Hz), 1.90 (m, 4H), 1.67 (s, 3H), 1.60 (s, 3H), 1.55 (m, 2H), 1.32 (t, 12H, J=7.0 Hz), 1.30 (m, 5H), 1.10 (m, 2H), 0.85 (d, 2H, J=6.0 Hz) ppm.

Mass Spec (CI-NH₃, +ions) m/e 472 (M+NH₄), 455 (M+H).

E. (R)-(6,10-Dimethyl-9-undecenylidene)bisphosphonic acid, tetrasodium salt

To a stirred solution of 1.00 g (2.20 mmol) of Part D ester in 10 mL of dichloromethane at room temperature was added 0.53 g (4.40 mmol) of 2,4,6-collidine followed by 2.02 g (13.20 mmol) of bromotrimethylsilane. The reaction was allowed to stir at room temperature for 14 hours when the solvent was evaporated and the semisolid residue pumped (~1 mm pressure) for 0.5 hours. The residue was dissolved by adding 10 mL of 1N NaOH solution (10 mmol) then diluting with 15 mL of water. The solution was freeze dried to provide an off white solid. The solid was purified by precipitation as follows.

(1) The solid was dissolved in 7 mL of water, warmed to 60° C., then precipitated out of the alkaline solution by adding 7 mL of acetone and cooling to 0° C. for 30 minutes.

(2) The mother liquor was decanted away from the gelatinous solid, the solid was washed with 7 mL of 3:1 acetone/water and the mixture stirred for 10 minutes. This washing procedure was performed three times. In each of the washings the gelatinous solid was broken up and "mashed" with a glass rod in order to aid the washing.

(3) The solid was washed with 10 mL of 5:1 acetone/water and finally 10 mL of acetone. At this point, the white solids were filtered and pumped for 18 hours to provide 0.90 g (95%) of title compound as a fine powder.

$[\alpha]_D^{20}$ +2.4° (c=1, H₂O).

IR (KBr) 3439, 2924, 2856, 1635, 1456, 1093, 949 cm$^{-1}$.

$^1$H NMR (D₂O, 400 MHz): δ 5.17 (t, 1H, J=7.0 Hz), 1.95 (m, 2H), 1.65 (m, 3H), 1.62 (s, 3H), 1.56 (s, 3H), 1.45-1.20 (m, 7H), 1.10 (m, 2H), 0.80 (d, 3H, J=6.20 Hz) ppm.

Mass Spec (FAB, +ions) m/e 453 (M+Na), 431 (M+H), 409 (M-Na+2H), 391 (M-Na+2H-H₂O).

Anal. Calc'd for C₁₃H₂₄O₆Na₄P₂+1.90 H₂O: C, 33.62; H, 6.03; P, 13.34.

Found: C, 33.99; H, 6.43; P, 13.25.

EXAMPLE 33

(S)-(6,10-Dimethyl-9-undecenylidene)bisphosphonic acid, tripotassium salt

A. (S)-(6,10-Dimethyl-9-undecenylidene)bisphosphonic acid, tetraethyl ester

Following procedure of Example 32 Parts A to D except substituting (R)-(+)-β-citronellol in Part A, the title tetraethyl ester is obtained.

TLC Silica gel (1:9 ethanol/ethyl acetate) $R_f=0.40$.

IR (film) 2978, 2915, 2868, 1646, 1243, 1026, 968 cm$^{-1}$.

$^1$H NMR (CDCl₃,270 MHz): δ 5.10 (t, 1H, J=6.9 Hz), 4.15 (m, 8H), 2.27 (tt, 1H, J=24.0, 5.9 Hz), 1.90 (m, 4H), 1.67 (s, 3H), 1.60 (s, 3H), 1.55 (m, 2H), 1.32 (t, 12H, J=7.0 Hz), 1.30 (m, 5H), 1.10 (m, 2H), 0.85 (d, 2H, J=6.0 Hz) ppm.

Mass Spec (CI-NH₃, +ions) m/e 472 (M+NH₄), 455 (M+H).

B. (S)-(6,10-Dimethyl-9-undecenylidene)bisphosphonic acid, tripotassium salt

To a stirred solution of 0.90 g (1.98 mmol) of Part A ester in 9 mL of dichloromethane at room temperature was added 0.24 g (2.00 mmol) of 2,4,6-collidine followed by 1.53 g (10.00 mmol) of bromotrimethylsilane. The reaction was allowed to stir at room temperature for 14 hours when the solvent was evaporated and the semisolid residue pumped (~1 mm presure) for 0.5 hours. The residue was dissolved by adding 8.78 mL of 1N KOH solution (8.78 mmol) then diluting with 15 mL of water. The solution was freeze dried to provide off white solids. The solids were purified by MPLC on a column of SP207SS gel (2.5 cm diam.×15 cm height) eluting with water (150 mL) followed by a gradient created by the gradual addition of 400 mL of acetonitrile to a reservoir of 350 mL of water. Approximately 10 mL fractions were collected. The acetonitrile was removed under reduced pressure and the aqueous solution was lyophilized to provide 0.55 g (60%) of title salt as a white lyophilate.

$[\alpha]_D^{20}$-2.1° (c=1, H₂O).

IR (KBr) 3418, 2924, 2857, 1632, 1456, 1111, 872 cm$^{-1}$.

$^1$H NMR (D₂O, 400 MHz): δ 5.18 (t, 1H, J=7.5 Hz), 1.95 (m, 2H), 1.65 (m, 3H), 1.63 (s, 3H), 1.57 (s, 3H), 1.45-1.20 (m, 7H), 1.10 (m, 2H), 0.80 (d, 3H, J=6.6 Hz) ppm.

Mass Spec (FAB, +ions) m/e 533 (M+2K-H), 495 (M+K), 457 (M+H), 439 (M+H-H₂O).

Anal. Calc'd for C₁₃H₂₅O₆K₃P₂+0.94 H₂O: C, 32.97; H, 5.72; P, 13.08

Found: C, 32.97; H, 6.07; P, 13.27.

EXAMPLE 34

(E)-[4-(2'-Methyl[1,1'-biphenyl]-4-yl)-3-butenylidene]-bisphosphonic acid, tetrapotassium salt A. 4-Bromo-2'-methyl-1,1'-biphenyl A stirred solution of 21.0 mL of (2-methylphenyl)-magnesium bromide (42.0 mmol, 2.0M in diethyl ether) was evaporated in situ at room temperature. The syrupy residue was redissolved in 50 mL of THF and cooled to −20° C. under argon. To this solution was added a solution of 6.84 g (50.0 mmol) of thricefused zinc chloride. The resulting thick white slurry was warmed to room temperature and stirred for 1 hour. After cooling to −78° C., a solution of 11.32 g (40.0 mmol) of 1-bromo-4-iodobenzene and 500 mg (0.4 mmol) of tetrakis(triphenylphosphine)palladium in 50 mL of THF was added over the course of thirty minutes. After an additional 20 minutes, the cooling bath was removed, the reaction stirred at room temperature for 2 hours and then quenched with 100 mL of 1M hydrochloric acid. The mixture was extracted twice with hexanes, the extracts combined, washed once with saturated sodium bicarbonate solution and once with 10% sodium thiosulfate. The organic extract was dried (MgSO$_4$) and evaporated. The crude product (11.3 g) was purified by distillation (bp 93°–95° C. at 0.5 Torr) to give 8.06 g (82%) of title compound as a colorless oil.

TLC Silica gel (hexanes) $R_f$=0.4.

IR (film) 3160, 3120, 2950, 2920, 2860, 1465, 1380, 1065, 995, 825, 755, 720 cm$^{-1}$.

$^1$H NMR (CDCl$_3$, 270 MHz): δ 7.51 (d, 2H, J=8.2 Hz), 7.20 (m, 6H), 2.24 (s, 3H) ppm.

MS (CI-NH$_3$, +ions) m/e 246, 248 (M).

B. (E)-3-(2'-Methyl[1,1'-biphenyl]-4-yl)-2-propenoic acid, butyl ester

A stirred solution of 6.00 g (24.3 mmol) of Part A compound, 106 mg (0.35 mmol) of tri-p-tolylphosphine, 4.4 mL (30.7 mmol) of n-butyl acrylate, 12 mL (50.0 mmol) of tributylamine and 10 mg (0.1 mmol) of hydroquinone was purged with a stream of nitrogen gas for 20 minutes at room temperature. To this mixture was added 4 mg (0.018 mmol) of palladium acetate. The reaction was heated to 150° C. for 18 hours under argon and then cooled to room temperature. The resulting slurry was diluted with ether, extracted twice with 50 mL of 1M hydrochloric acid, once with brine and once with saturated sodium bicarbonate solution. The organic phase was dried (MgSO$_4$) and evaporated. The crude product (7.5 g) was purified by flash chromatography on silica gel (5×25 cm column) eluted with 1 L of hexanes and then 1:1 dichloromethane/hexanes to give 5.68 g (79%) of title compound as a colorless oil.

TLC Silica gel (1:1 dichloromethane/hexanes) $R_f$=0.2.

IR (film) 3060, 3020, 2950, 2920, 2860, 1695, 1625, 1595, 1470, 1440, 1300, 1255, 1195, 1160, 825, 760 cm$^{-1}$.

$^1$H NMR (CDCl$_3$, 270 MHz): δ 7.73 (d, 1H, J=15.9 Hz), 7.56 (d, 2H, J=8.2 Hz), 7.30 (d, 2H, J=8.2 Hz), 7.20 (m, 4H), 6.47 (d, 1H, J=15.8 Hz), 4.23 (q, 2H, J=7.0 Hz), 2.27 (s, 3H), 1.70 (quintet, 2H, J=6.4 Hz), 1.43 (sextet, 2H, J=7.0 Hz), 0.97 (t, 3H, J=7.6 Hz) ppm.

MS (CI-NH$_3$, +ions) m/e 295 (M+H).

C. (E)-1-Acetyloxy-3-[(2'-methyl[1,1'-biphenyl]−4-yl)]-2-propene

To a stirred solution of 4.47 g (15.2 mmol) of Part B compound in 50 mL of dichloromethane at 0° C. under nitrogen was added a solution of 32 mL (32 mmol, 1M in hexanes) of diisobutylaluminum hydride over 5 minutes. The resulting pale yellow solution was stirred for 2 hours and then quenched with 2 mL of methanol. The solution was then treated with 150 mL of 1M potassium sodium tartrate. A gel formed which dissolved within 5 minutes. The reaction mixture was extracted twice with ether. The extracts were combined, dried (Na$_2$SO$_4$) and evaporated. The resulting oil (3.6 g) was dissolved in 25 mL of THF, cooled to 0° C. under nitrogen and 4.6 mL (25 mmol) of diisopropylethylamine and 2.4 mL (25 mmol) of acetic anhydride were added. After 1 hour, the reaction mixture was diluted with ether, washed twice with 1M hydrochloric acid, once with brine and once with saturated sodium bicarbonate. The organic phase was dried (MgSO$_4$) and evaporated onto 10 g of silica gel. Purification by flash chromatography on silica gel (5×20 cm column) eluted with 3:2 dichloromethane:hexane gave title compound as a white solid, m.p. 54°–56° C., 3.55 g, 88% from Part B compound.

TLC Silica gel (3:2 dichloromethane/hexanes) $R_f$=0.2.

$^1$H NMR (CDCl$_3$, 270 MHz): δ 7.43 (d, 2H, J=8.2 Hz), 7.20 (m, 6H), 6.70 (d, 1H, J=15.8 Hz), 6.32 (dt, 1H, J=15.8, 6.4 Hz), 4.74 (dd, 2H, J=1.1, 6.4 Hz), 2.27 (s, 3H), 2.11 (s, 3H) ppm.

MS (CI-NH$_3$, +ions) m/e 267 (M+H).

Anal. Calc'd for C$_{18}$H$_{18}$O$_2$: C, 81.17; H, 6.81.
Found: C, 80.87; H, 6.82.

D. (E)-[4-(2'-Methyl[1,1'-biphenyl]-4-yl)-3-butenylidene]-bisphosphonic acid, tetraethyl ester To a stirred solution of 2.036 g (7.64 mmol), of Part C compound, 3.81 mL (15.4 mmol, 2.0 equivalents) of bis(trimethylsilyl)acetamide, 4.39 g (15.2 mmol, 2.0 equivalents) of tetraethyl methylenediphosphonate and 110 mg (0.42 mmol) of triphenylphosphine in 25 mL of THF under argon was added 250 mg (0.22 mmol) of tetrakis(triphenylphosphine)palladium. The resulting mixture was heated to reflux for 24 hours. The reaction was cooled and evaporated and pumped at room temperature at 0.2 Torr for 24 hours. The residue was diluted with dichloromethane and evaporated onto 15 g of silica gel. Purification by flash chromatography on silica gel (5×20 cm column) eluted with 1:4 isopropanol/hexanes gave title compound as a colorless oil, 3.31 g, 87% yield.

TLC (silica gel 60): $R_f$=0.2, (1:4 isopropanol/hexane).

IR (thin film) 2980, 2840, 2820, 1470, 1430, 1380, 1240, 1155, 1090, 1020, 960, 850, 780, 760 cm$^{-1}$.

1H NMR (CDCl$_3$, 270 MHz): δ 7.40 (d, 2H, J=8.2 Hz), 7.20 (m, 6H), 6.53 (d, 1H, J=15.8 Hz), 6.42 (dt, 1H, J=15.8, 5.8 Hz), 4.20 (m, 8H), 2.89 (tt, 2H, J=6.4, 16.8 Hz), 2.49 (tt, 1H, J=6.4, 23.6 Hz), 2.27 (s, 3H), 1.35 (dt, 12H, J=1.8, 5.8 Hz) ppm.

MS (CI-NH$_3$, +ions) m/e 495 (M+H).

E. (E)-[4-(2'-Methyl[1,1'-biphenyl]-4-yl)-3-butenylidene]-bisphosphonic acid, tetrapotassium salt To a stirred solution of 1.45 g (2.94 mmol) of Part D compound in 15 mL of dichloromethane at room temperature under nitrogen was added 1.24 mL (9.0 mmol, 3.0 equivalents) of 2,4,6-collidine and then 2.46 mL (18.0 mmol, 6.0 equivalents) of bromotrimethylsilane. The clear, colorless solution was stirred for 24 hours and then evaporated at room temperature. The residue was treated with 18 mL (18.0 mmol, 6.0 equivalents) 1.0M potassium hydroxide solution, diluted with water and lyophilized. The lyophilate was purified by MPLC (2.5×15 cm column, SP207SS Sepabeads, water as elutent). The chromatography afforded pure fractions which were pooled, filtered and precipitated with acetone to give the title compound 575 mg (33%) of a white solid. Slightly impure fractions were lyophilized to give an additional 630 mg (35%) of title compound.

IR (KBr pellet) 3427, 3021, 2953, 2922, 1633, 1157, 1128, 1107, 1088, 1005, 970, 758 cm$^{-1}$.

$^1$H NMR (D$_2$O, 270 MHz): δ 7.53 (d, 2H, J=8.2 Hz), 7.30 (m, 6H), 6.59 (m, 2H), 2.72 (tt, 2H, J=5.8, 7.0 Hz), 2.23 (s, 3H), 1.93 (tt, 1H, J=7.0, 21.1 Hz) ppm.

MS (FAB, +ions) m/e 535 (M+H), 497 (M-K+2H), 479 (M-K+2H-H$_2$O), 459 (M-2K+3H).

Anal. Calc'd for C$_{17}$H$_{16}$K$_4$P$_2$O$_6$·1.85H$_2$O: C, 35.95; H, 3.50; P, 10.91.

Found: C, 36.26; H, 3.89; P, 11.27.

With respect to Example 36, it will be appreciated that the procedure in Part D describing the Pd-catalyzed allylic alkylation of the methylene bisphosphonate tetraester is a preferred procedure generally applicable to preparing compounds of the invention containing an alkene moiety located γ, δ to the phosphonates, according to the following reaction:

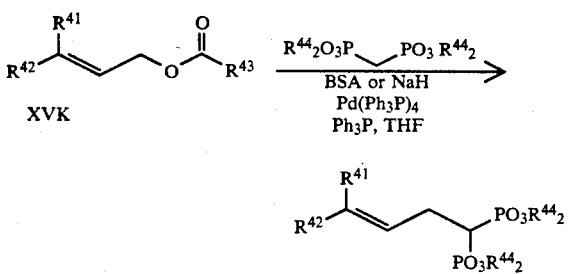

R$^{44}$ is alkyl; R$^{41}$, R$^{42}$ are independently selected from H, alkyl, aryl or vinyl; R$^{43}$ is alkyl, aryl, O-alkyl or O-aryl; BSA is bis(trimethylsilyl)acetamide.

In addition, an allylic ester of the structure

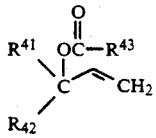 XVL may be employed as the starting material in place of XVK.

Compounds XVK and XVL may be prepared employing conventional procedures.

It will also be appreciated that the alkene moiety (such as in the Part D compound of Example 36) may be hydrogenated to form the corresponding saturated compound employing conventional hydrogenation procedures.

The following additional compounds of the invention were prepared according to the procedures set out hereinbefore.

(1) (E)-(9,13-dimethyl-8,12-tetradecadienylidene)bisphosphonic acid, trisodium salt;
(2) (E,E)-(6,10,14-trimethyl-5,9-pentadecadienylidene)-bisphosphonic acid, trisodium salt;
(3) [4-(4-butylphenyl)butylidene]bisphosphonic acid, tripotassium salt;
(4) [3-(4-heptylphenyl)butylidene]bisphosphonic acid;
(5) (E)-[4-([1,1'-biphenyl]-3-yl)-3-butenylidene]bisphosphonic acid, tripotassium salt;
(6) [4-([1,1'-biphenyl]-3-yl)butylidene]bisphosphonic acid, tripotassium salt;
(7) [2-[4-(2-methyl-1-propenyl)phenyl]ethylidene]bisphosphonic acid, tetrasodium salt;
(8) [4-([1,1'-biphenyl]-2-yl)butylidene]bisphosphonic acid;
(9) (E)-[4-([1,1'-biphenyl]-2-yl)-3-butenylidene]bisphosphonic acid, tripotassium salt;
(10) (E)-[4-[4-(2,6-dimethyl-1,5-heptadienyl)-2-methylphenyl]butylidene]bisphosphonic acid, tripotassium salt;
(11) [4-(4'-propyl[1,1'-biphenyl]-4-yl)butylidene]bisphosphonic acid;
(12) (E)-[4-([1,1'-biphenyl]-4-yl)-3-butenylidene]bisphosphonic acid, trisodium salt;
(13) [4-([1,1'-biphenyl]-4-yl)-3-butynylidene]bisphosphonic acid, trisodium salt;
(14) (E,E)-[4-[4-(2,6-dimethyl-1,5-heptadienyl)-2-methylphenyl]-3-butenylidene]bisphosphonic acid, tripotassium salt;
(15) (E)-[4-(3-methyl[1,1'-biphenyl]-4-yl)-3-butenylidene]bisphosphonic acid, trisodium salt;
(16) (E)-[4-(4'-fluoro[1,1'-biphenyl]-4-yl)-3-butenylidene]bisphosphonic acid, tripotassium salt;
(17) (E)-[4-[4'-(2-methyl-1-propenyl)[1,1'-biphenyl]-4-yl]-3-butenylidene]bisphosphonic acid, tripotassium salt;
(18) (Z)-[4-([1,1'-biphenyl]-4-yl)-3-butenylidene]bisphosphonic acid, tripotassium salt;
(19) [4-(3-methyl[1,1'-biphenyl]-4-yl)butylidene]bisphosphonic acid, tripotassium salt;
(20) [4-(4'-fluoro[1,1'-biphenyl]-4-yl)butylidene]bisphosphonic acid, tripotassium salt;
(21) [4-[4'-(2-methyl-1-propenyl)1,1'-biphenyl]-4-yl]butylidene]bisphosphonic acid, trisodium salt;
(22) [4-(4-(phenylmethyl)phenyl-4-yl)butylidene]bisphosphonic acid, tetrapotassium salt;
(23) [4-[[1,1'-biphenyl]-4-yl]-4-hydroxybutylidene]bisphosphonic acid, tripotassium salt;
(24) [4-(2'-methyl[1,1'-biphenyl]-4-yl)butylidene]bisphosphonic acid, tetrapotassium salt.

What is claimed is:

1. A compound having the structure

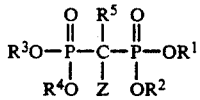

wherein R$^1$, R$^2$, R$^3$ and R$^4$ are the same or different and are H, lower alkyl, a metal ion or a prodrug ester;

R$^5$ is H, halogen or lower alkyl;

Z is alkenyl group contains at least 7 carbon atoms in the chain and from 1 to 4 double bonds; aklynyl containing 1 to 4 triple bonds; mixed alkenyl-alkynyl containing 1 to 3 double bonds and 1 to 3 triple bonds, and wherien alkenyl and/or alkynyl may be substituted or unsubstituted; and wherein alkenyl and/or alkynyl may optionally include a (CH$_2$)$_x$ group, wherein x is 1 to 15, which is linked to the carbon joining the two phosphorus moieties; and wherein stubsituted alkenyl and substituted alkynyl refer to such groups substituted with alkyl, alkenyl, alkynyl, halogen, hydroxy, alkoxy, alkenyloxy, alkynyloxy, aryl and/or cycloalkyl, provided that if Z is an alkenyl group and contains only one carbon-carbon double bond, then it must be substituted with at least one group other than an alkyl group; or a group of the structure

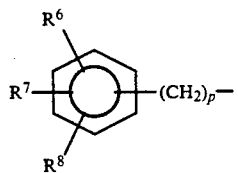

wherein (CH$_2$)$_p$ contains from 1 to 15 carbons in the chain and may include 0, 1, 2 or 3 triple bonds in the normal chain and/or may include 0, 1, 2 or 3 substituents which are alkyl, alkenyl, alkoxy, alkynyl, hydroxy and/or halogen; and R$^6$, R$^7$ and R$^8$ are the same or different and are H, alkyl containing 1 to 40 carbons, alkoxy containing 1 to 40 carbons, alkenyl containing 2 to 40 carbons, alkenyloxy containg 2 to 40 carbons, alkynyl containing 2 to 40 carbons, alkynyloxy, aryloxy, hydroxy, halogen, nitro, amino, thiol, alkylthio, arylthio, arylsulfinyl, alkylsulfinyl, arylsulfonyl, alkylsulfonyl, carboxy, alkoxycarbonyl, alkylcarbonyloxy, arylcarbonyloxy, aminocarbonyl, arylcarbonylamino or alkylcarbonylamino, at least one or R$^6$, R$^7$ and R$^8$ being alkenyl, alkenyloxy, alkynyl or alkynyloxy, and wherein the total number of carbons in

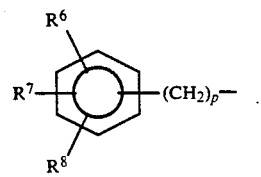

exceeds 10 carbons, wherein the prodrug ester is (1-alkanoyloxy)-alkyl,

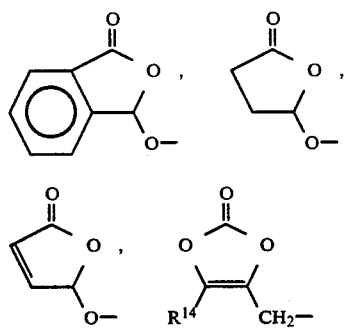

wherein R$^{14}$ is H, CH$_3$, C$_6$H$_5$; or R$^1$ and R$^2$, and/or R$^3$ and R$^4$ can be taken together as in

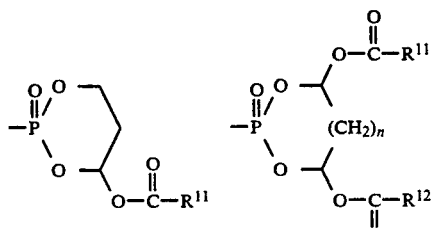

wherein R$^{11}$ and R$^{12}$ are H, alkyl, aryl, or arylalkyl and n is 0 to 3.

2. The compound as defined in claim 1 wherin Z is substituted alkenyl or substituted alkynyl.

3. The compound as defined in claim 1 wherein the substituted alkenyl or substituted alkynyl group is substituted with from 1 to 4 substituents.

4. The compound as defined in claim 1 wherein the substituted alkenyl or substituted alkynyl is substituted with 1 to 4 substituents selected from alkyl, alkenyl, alkynyl, halogen, hydroxy, alkoxy, alkenyloxy, alkynyryloxy, aryl and cycloalkyl.

5. The compound as defined in claim 1 wherein substituted alkenyl contains from 1 to 3 double bonds and includes from 1 to 3 alkyl substituents.

6. The compound as defined in claim 1 wherein substituted alkenyl is substituted with from 1 to 3 methyl groups.

7. The compound as defined in claim 1 wherein Z includes a (CH$_2$)$_x$ linking group wherein x is 1 to 15.

8. The compound as defined in claim 1 wherein Z is

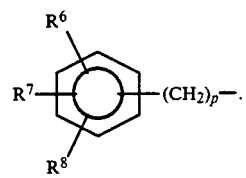

9. The compound as defined in claim 1 wherein Z is substituted alkynyl.

10. The compound as defined in claim 1 wherein Z is mixed alkenyl-alkynyl.

11. The compound as defined in claim 1 wherein R$^5$ is H.

12. The compound as defined in claim 1 wherein R$^1$, R$^2$, R$^3$ and R$^4$ are independently H, alkyl or Na or K.

13. The compound as defined in claim 1 wherein Z is

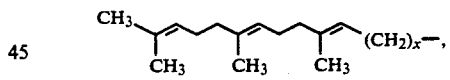

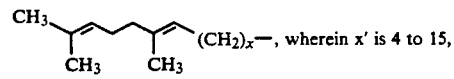

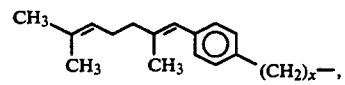

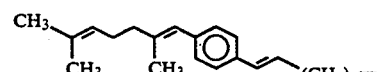

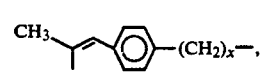

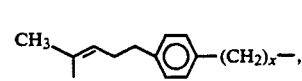

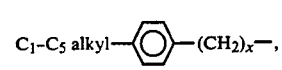

-continued

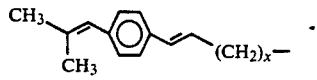

14. The compound as defined in claim 1 having the name (E,E)-(6,10,14-trimethyl-5,9,13-pentadecatrienylidene)bisphosphonic acid, or ester thereof, or salt thereof, or mixed ester-salt thereof, or trisodium salt or tripotassium salt; (E)-(10,14-dimethyl-9,13-pentadecadienylidene)bisphosphonic acid, or ester thereof, or salt thereof, or mixed ester-salt thereof, or trisodium salt; (E,E)-(7,11,15-trimethyl-6,10,14-hexadecatrienylidene)bisphosphonic acid, or ester thereof, or salt thereof, or mixed ester-salt thereof, or trisodium salt; (E)-(6,10-dimethyl-5,9-undecadienylidene)bisphosphonic acid, or ester thereof, or salt thereof, or mixed ester-salt thereof, or tetrasodium salt; (E,E)-(5,9,13-trimethyl-4,8,12-tetradecatrienylidene)bisphosphonic acid, or ester thereof, or salt thereof, or mixed ester-salt thereof, or trisodium salt; (E,E)-(9,13,17-trimethyl-8,12,16-octadecatrienylidene)bisphosphonic acid, or ester thereof, or salt thereof, or mixed ester-salt thereof, or trisodium salt; (E,E)-(4,8,12-trimethyl-3,7,11-tridecatrienylidene)bisphosphonic acid, or ester thereof, salt thereof, or mixed ester-salt thereof, or trisodium salt; (E)-(4,8-dimethyl-3,7-nonadienylidene)bisphosphonic acid, or ester thereof, salt thereof, or mixed ester-salt thereof, or trisodium salt; (E)-(7,11-dimethyl-6,10-dodecadienylidene)bisphosphonic acid, or ester thereof, salt thereof, mixed ester-salt thereof, tripotassium salt or tetrasodium salt thereof; (Z)-(6,10-dimethyl-5,9-undecadienylidene)bisphosphonic acid, or ester thereof, salt thereof, or mixed ester-salt thereof, or tetrasodium salt; (E)-(8,12-dimethyl-7,11-tridecadienylidene)bisphosphonic acid, or ester thereof, or salt thereof, or mixed ester-salt thereof or tetrasodium salt thereof.

15. The compound as defined in claim 1 having the name (E)-[4-[4-(2,6-dimethyl-1,5-heptadienyl)phenyl]-butylidene]bisphosphonic acid, or ester thereof, salt thereof or mixed ester-salt thereof, or tripotassium salt; [4-[4-(2-methyl-1-propenyl)phenyl]butylidene]bisphosphonic acid, or ester thereof, salt thereof or mixed ester-salt thereof, or trisodium salt; [4-[4-(4-methyl-3-pentenyl)phenyl]butylidene]bisphosphonic acid, or ester thereof, salt thereof or mixed ester-salt thereof, or tripotassium salt; [4-[3-(2-methyl-1-propenyl)phenyl]butylidene]bisphosphonic acid, or ester thereof, salt thereof or mixed ester-salt thereof, or trisodium salt; (E)-[4-[4-(2-methyl-1-propenyl)phenyl]-3-butenylidene]bisphosphonic acid, or ester thereof, salt thereof or mixed ester-salt thereof, or trisodium salt; [6-[4-(2-methyl-1-propenyl)phenyl]hexylidene]bisphosphonic acid, or ester thereof, salt thereof or mixed ester-salt thereof, or trisodium salt; [2-[4-(4-methyl-3-pentenyl)phenyl]ethylidene]bisphosphonic acid, or ester thereof, salt thereof or mixed ester-salt thereof, or tripotassium salt; (E)-[2-[4-(2,6-dimethyl-1,5-heptadienyl)-phenyl]ethylidene]bisphosphonic acid, or ester thereof, salt thereof or mixed ester-salt thereof, or tripotassium salt; (E)-[5-[4-(2,6-dimethyl-1,5-heptadienyl)phenyl]-pentylidene]bisphosphonic acid, or ester thereof, salt thereof or mixed ester-salt thereof, or tripotassium salt; (E,E)-[4-[4-(2,6-dimethyl-1,5-heptadienyl)phenyl]-3-butenylidene]bisphosphonic acid, or ester thereof, salt thereof or mixed ester-salt thereof, or tripotassium salt; (E)-(5,9-dimethyl-4,8-decadienyl)bisphosphonic acid, or ester thereof, salt thereof or mixed ester-salt thereof, or trisodium salt; (E)-[4-[3-(2,6-dimethyl-1,5-heptadienyl)phenyl]butylidene]bisphosphonic acid, or ester thereof, salt thereof or mixed ester-salt thereof, or tripotassium salt; (E)-(9,13-dimethyl-8,12-tetradecadienylidene)bisphosphonic acid, or ester thereof, salt thereof or mixed ester-salt thereof or trisodium salt; (E,E)-(6,10,14-trimethyl-5,9-pentadecadienylidene)bisphosphonic acid, or ester thereof, salt thereof or mixed ester-salt thereof or trisodium salt; [2-[4-(2-methyl-1-propenyl)phenylethylidene]bisphosphonic acid, or ester thereof, salt thereof or mixed ester-salt thereof or tetrasodium salt; (E)-[4-[4-(2,6-dimethyl-1,5-heptadienyl)-2-methylphenyl]butylidene]bisphosphonic acid, or ester thereof, salt thereof or mixed ester-salt thereof or tripotassium salt; (E,E)-[4-[4-(2,6-dimethyl-1,5-heptadienyl)-2-methylphenyl]-3-butenylidene]bisphosphonic acid, or ester thereof, salt thereof or mixed ester-salt thereof or tripotassium salt.

16. A compound having the structure

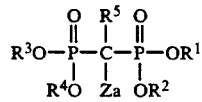

wherein $R^1$, $R^2$, $R^3$ and $R^4$ are the same or different and are H, alkyl, a metal ion or a prodrug ester as defined in claim 1; $R^5$ is H, halogen or alkyl, and Za is substituted alkenyl wherein the alkenyl group contains at least 7 carbon atoms in the chain and which includes 1 to 4 double bonds and is substituted with from 1 to 4 lower alkyl groups; and alkenyl may optionally include a $(CH_2)_x$ group, wherein x is 1 to 15, which is linked to the C joining the two phosphorus moieties.

17. The compound as defined in claim 16 wherein Za is substituted alkenyl containing 1 to 3 double bonds and is substituted with from 1 to 3 alkyl groups.

18. The compound as defined in claim 16 wherein the alkyl groups are each methyl.

19. The compound as defined in claim 16 wherein the Za groupd includes a $(CH_2)_x$ linking group wherein x is 1 to 15.

20. A hypocholesterolemic or hypolipemic composition comprising a compound as defined in claim 1 and a pharmaceutically acceptable carrier therefor.

21. The composition as defined in claim 20 further including a pharmaceutically acceptable detergent.

22. A method of inhibiting or treating hypercholesterolemia, which comprises administering to a patient in need of such treatment a therapeutically effective amount of a compound as defined in claim 1.

23. A method of inhibiting or treating atherosclerosis which comprises administering to a patient in need of such treatment a therapeutically effective amount of a compound as defined in claim 1.

24. A method of inhibiting cholesterol biosynthesis, which comprises administering to a patient in need of such treatment a therapeutically effective cholesterol biosynthesis inhibiting amount of a compound as defined in claim 1.

* * * * *